Figure 1:
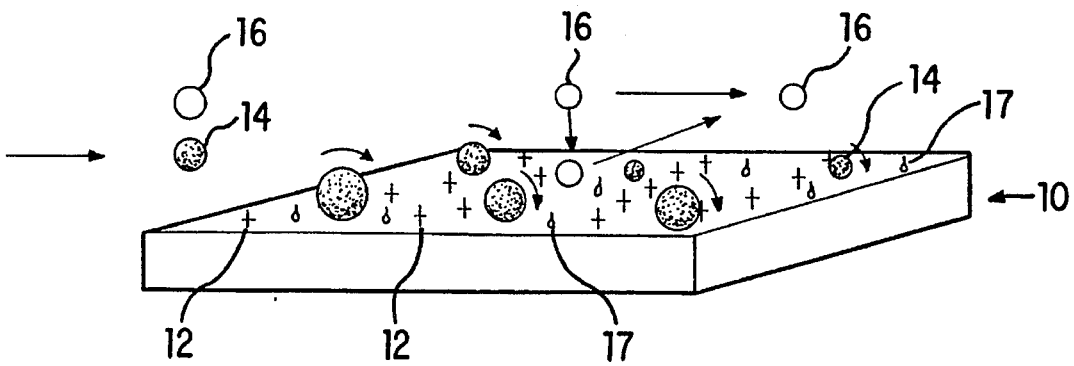

USO05460945A

United States Patent [19]

Springer et al.

[11] Patent Number: 5,460,945
[45] Date of Patent: Oct. 24, 1995

[54] DEVICE AND METHOD FOR ANALYSIS OF BLOOD COMPONENTS AND IDENTIFYING INHIBITORS AND PROMOTERS OF THE INFLAMMATORY RESPONSE

[75] Inventors: Timothy A. Springer, Chestnut Hill; Michael Lawrence, Brookline, both of Mass.

[73] Assignee: Center for Blood Research, Inc., Boston, Mass.

[21] Appl. No.: 887,444

[22] Filed: May 20, 1992

Related U.S. Application Data

[63] Continuation-in-part of Ser. No. 707,841, May 30, 1991, abandoned.

[51] Int. Cl.[6] .................. C12N 5/00; C12Q 1/02; G01N 33/566
[52] U.S. Cl. .................. 435/7.24; 422/58; 422/69; 427/2.11; 427/2.13; 435/2; 435/4.23; 435/7.8; 435/29; 435/30; 435/174; 435/176; 435/177; 435/240.2; 435/287.1; 435/287.2; 435/287.9; 435/288.3; 435/288.5
[58] Field of Search .................. 422/69, 58; 427/2; 435/2, 7.23, 7.24, 7.8, 29, 30, 174, 176, 177, 287, 240.2; 436/503

[56] References Cited

U.S. PATENT DOCUMENTS

| | | | |
|---|---|---|---|
| 4,925,572 | 5/1990 | Pall | 210/767 |
| 4,953,147 | 6/1990 | Ullman et al. | 210/695 |
| 4,963,260 | 10/1990 | Naoi | 210/446 |
| 4,981,596 | 1/1991 | Shiimo et al. | 210/658 |
| 4,983,359 | 1/1991 | Tomioka et al. | 422/81 |
| 5,081,034 | 1/1992 | Bevilacqua et al. | 435/252.33 |
| 5,089,479 | 2/1992 | Krivan et al. | 514/25 |
| 5,188,959 | 2/1993 | Haberman | 435/240.243 |
| 5,198,424 | 3/1993 | McEver | 514/13 |
| 5,217,870 | 6/1993 | Hession et al. | 435/7.24 |
| 5,225,330 | 7/1993 | Ginsburg et al. | 435/7.32 |
| 5,318,890 | 6/1994 | Rosen et al. | 435/7.24 |

FOREIGN PATENT DOCUMENTS 387668  9/1990  European Pat. Off. .

OTHER PUBLICATIONS

L. A. Lasky, Science, 258, 964–969, 1992.

Lobb et al., 1991, "Expression and functional characterization of a soluble form of endothelialleukocyte adhesion molecule 1," J. Immunol. 147:124–129.

Berg et al., 1991, "The human peripheral lymph node vascular addressin is a ligand for LECAM–1, the peripheral lymph node homing receptor," J. Cell Biol. 114:343–349.

Kishimoto et al., 1990, "Identification of a human peripheral lymph node homing receptor: a rapidly down–regulated adhesion molecule," Proc. Natl. Acad. Sci. USA 87:2244–2248.

Staunton et al., 1988, "Primary structure of ICAM–1 demonstrates interaction between members of the immunoglobulin and integrin supergene families," Cell 52:925–933.

Polte et al., 1990, "Full length vascular cell adhesion molecule 1 (VCAM–1)," Nucl. Acids Res. 18(19):5901.

Lawrence and Springer, 1991, Leukocytes roll on a selectin at physiologic flow rates: distinction from and prerequisite for adhesion through integrins, Cell 65:859–73.

Smith et al., 1989, Cooperative interactions of LFA–1 and Mac–1 with intercellular adhesion molecule–1 in facilitating adherence and transendothelial migration of human neutrophils in vitro, J. Clin. Invest. 83:2008–17.

Polley et al., 1991, CD62 and endothelial cell–leukocyte adhesion molecule 1 (ELAM–1) recognize the same carbohydrate ligand, sialyl–Lewis x, Proc. Natl. Acad. Sci. USA 88:6224–28.

Lawrence et al., 1990, Effect of venous shear stress on CD18-mediated neutrophil adhesion to cultured endothelium, Blood 75:227–37.

Chan et al., 1991, Influence of receptor lateral mobility on adhesion strengthening between membranes containing LFA–3 and CD2, J. Cell Biol. 115:245–55.

Shimizu et al., 1991, Activation–independent binding of human memory T cells to adhesion molecule ELAM–1, Nature 349:799–802.

Walz et al., 1990, Recognition by ELAM–1 of the Sialyl–Le$^x$ determinant on myeloid and tumor cells, Science 250:1132–35.

Butcher, 1991, Leukocyte–endothelial cell recognition: three(or more) steps to specificity and diversity, Cell

67:1033–36.

Huber et al., 1991, Regulation of transendothelial neutrophil migration by endogenous interleukin-8, Science 254:99–102.

Diamond et al., 1990, ICAM-1 (CD54): A counter-receptor for Mac-1 (CD11b/CD18), J. Cell Biol. 111:3129–39.

Jalkanen et al., 1987, Human lymphocyte and lymphoma homing receptors, Ann. Rev. Med. 38:467–76.

Fiebig et al., 1991, Rapid leukocyte accumulation by "spontaneous" rolling and adhesion in the exteriorized rabbit mesentery, Int. J. Microcirc: Clin. Exp. 10:127–44.

Cohnheim, 1889, Lectures on General Pathology: A Handbook for Practitioners and Students (London: The New Sydenham Society): 248–51.

Atherton and Born, 1973, Relationship between the velocity of rolling granulocytes and that of the blood flow in venules, J. Physiol. 233:157–65.

Marchesi, 1961, The site of leucocyte emigration during inflammation, O. J. Physiol. 46:115–18.

Segré and Silberberg, 1962, Behavior of macroscopic rigid spheres in Pioseuille flow. Part 2. Experimental Results and Interpretation, J. Fluid Mech. 14:136–157.

Goldsmith and Spain, 1984, Margination of leukocytes in blood flow through small tubes, Microvascular Res. 27:204–22.

Nobis et al., 1985, Radial distribution of white cells during blood flow in small tubes, Microvascular Res. 29:295–304.

Chien, 1982, Rheology in the microcirculation in normal and low flow states, Adv. in Shock Res. 8:71–80.

Springer, 1990, Adhesion receptors of the immune system, Nature 346:425–33.

Smith et al., 1988, Recognition of an endothelial determinant for CD18-dependent human neutrophil adherence and transendothelial migration, J. Clin. Invest. 82:1746–56.

deFougerolles et al., 1991, Characterization of ICAM-2 and evidence for a third counter-receptor for LFA-1, J. Exp. Med. 174:253–67.

Staunton et al., 1989, Functional cloning of ICAM-2, a cell adhesion ligand for LFA-1 homologous to ICAM-1, Nature 339:61–64.Buyon et al., 1988. Dissociation between increased surface expression of Gpl65/95 and homotypic neutrophil aggregation, J. Immunol. 140:3156–60.

Philips et al., 1988, Up-regulation of the iC3b receptor (CR3) is neither necessary nor sufficient to promote neutrophil aggregation, J. Clin Invest. 82:495–501.

Vedder and Harlan, 1988, Increased surface expressin of CD11b/CD18 (Mac-1) is not required for stimulated neutrophil adherence to cultured endothelium, J. Clin. Invest. 81:676–82.

Lo et al., 1989, Transient adhesion of neutrophils to endothelium, J. Exp. Med. 169:1779–93.

Dustin and Springer, 1988, Lymphocyte function-associated antigen-1 (LFA-1) interaction with intercellular adhesion molecule-1 (ICAM-1) is one of at least three mechanisms for lymphocyte adhesion to cultured endothelia cells, J. Cell Biol. 107:321–31.

Larson and Springer, 1990, Structure and function to leukocyte integrins, Immunol. Rev. 114:181–217.

Anderson and Springer, 1987, Leukocyte adhesion deficiency: an inherited defect in the Mac-1, LFA-1, and p. 150,95 glycoproteins, Ann. Rev. Med. 38:175–94.

Buchanan et al., 1982, Studies on the interactin between GP-180-deficient neutrophils and vascular endothelium, Blood 60:160–65.

Harlan et al., 1985, The role of neutrophil membrane glycoprotein GP- 150 in neutrophil adherence to endothelium in vitro, Blood 66:167–78.

Dlices et al., 1990, VACM-1 on activated endothelium interacts with the leukocyte integrin VLA-4 at a site distinct from the VLA-4/fibronectin binding site, Cell 60:577–84.

Osborn et al., 1989, Direct expressin cloning of vascular cell adhesion molecule 1, a cytokine-induced endothelial protein that binds to lymphocytes, Cell 59:1203–11.

Rice et al., 1990, Inducible cell adhesion molecule 110 (INCAM-110) is an endothelial receptor for lymphocytes, J. Exp. Med. 171:1369–74.

Wellicome et al., 1990, A monoclonal antibody that detects a novel antigen on endothelial cells that is induced by tumor necrosis factor, IL-1, or lipopolysaccharide, J. Immunol. 144:2558–65.

Carlos et al., 1990, Vascular cell adhesion molecule–1 mediates lymphocyte adherence to cytokine-activated cultured human endothelial cells, Blood 76:965–70.

Guan and Hynes, 1990, Lymphoid cells recognize alternatively spliced segment of fibronectin via the integrin receptor $\alpha_4\beta_1$, Cell 60:53–61.

Wayner et al., 1989, Identification and characterization of the T lymphocyte adhesin receptor for an alternative cell attachment domain (CS-1) in plasma fibronectin, J. Cell Biol. 109:1321–30.

Hemler, 1990, VLA proteins in the integrin family: structures, functions, and their role on leukocytes, Ann. Rev. Immunol. 8:365–400.

Polte et al., 1990, Full length vascular cell adhesion molecule 1 (VCAM-1), Nucl. Acids Res. 18:5901.

Cybulsky et al., 1991, Alternative splicing of human VCAM-1 in activated vascular endothelium, Amer. J. of Path. 138:815–20.

Hession et al., 1991, Cloning of an alternate form of vascular cell adhesion molecule-1 (VCAM1), J. Biol. Chem. 266:6682–85.

Larsen et al., 1989, PADGEM protein: a receptor that mediates the interaction of activated platelets with neutrophils and monocytes, Cell 59:305–12.

*Primary Examiner*—David Saunders
*Attorney, Agent, or Firm*—Pennie & Edmonds

[57] ABSTRACT

The present invention provides in vitro models of the in vivo rolling and arrest of leukocytes along the endothelial cell wall, which are important steps in the migration of leukocytes out of the blood stream and into tissue, as part of the inflammatory response. The in vitro models of the invention are functional under physiologic flow conditions resulting in physiologic shear stresses. In a specific embodiment, for modelling leukocyte rolling, the apparatus of the invention comprises a solid phase surface with rolling mediator molecules present thereon. Such rolling mediators are, for example, selectins and selectin ligands which have binding partners expressed on leukocytes. In another specific embodiment, for modelling leukocyte rolling followed by adhesion/arrest, the apparatus of the invention comprises a solid phase surface with both rolling mediators and integrin binding partners present thereon. The apparatuses of the invention can be used for collecting, concentrating, purifying, and analyzing blood and blood components, in particular, leukocytes and subsets thereof. The invention further relates to methods for identifying inhibitors or, alternatively, promoters (agonists, functional components) of the inflammatory response. Therapeutic and diagnostic methods, pharmaceutical compositions and kits are also provided.

101 Claims, 18 Drawing Sheets

DEVICE AND METHOD FOR ANALYSIS OF BLOOD COMPONENTS AND IDENTIFYING INHIBITORS AND PROMOTERS OF THE INFLAMMATORY RESPONSE

This invention was made with government support under grant number CA 31799 from the National Institutes of Health. The government has certain rights in the invention. This application is a continuation-in-part of application Ser. No. 07/707,841, filed May 30, 1991 and abandoned, which is incorporated by reference herein in its entirety.

TABLE OF CONTENTS

1. INTRODUCTION
2. BACKGROUND OF THE INVENTION
   2.2. SEPARATION OF BLOOD AND BLOOD COMPONENTS
3. SUMMARY OF THE INVENTION
4. DESCRIPTION OF THE FIGURES
5. DETAILED DESCRIPTION OF THE INVENTION
   5.1. THE IN VITRO MODELS OF THE INVENTION
   5.2. ROLLING MEDIATOR COMPONENTS OF THE APPARATUSES OF THE INVENTION
   5.3. CHEMOATTRACTANTS FOR USE WITH THE ARREST MODEL APPARATUSES OF THE INVENTION
   5.4. INTEGRIN BINDING PARTNERS IN THE ARREST MODEL APPARATUSES OF THE INVENTION
   5.5. SOLID PHASES OF THE APPARATUSES OF THE INVENTION
   5.6. THE APPARATUSES OF THE INVENTION
   5.7. METHODS OF BLOOD COLLECTION, PURIFICATION AND ANALYSIS
      5.7.1. ANALYSIS AND QUANTITATION
   5.8. KITS
   5.9. DIAGNOSTIC AND THERAPEUTIC UTILITIES OF THE METHODS OF COLLECTION, PURIFICATION, AND ANALYSIS OF BLOOD AND BLOOD COMPONENTS
   5.10. IDENTIFICATION OF INHIBITORS OR PROMOTERS OF THE INFLAMMATORY RESPONSE
      5.10.1. IDENTIFICATION OF INHIBITORS
      5.10.2. IDENTIFICATION OF PROMOTERS
   5.11. THERAPEUTIC AND DIAGNOSTIC UTILITIES OF THE INHIBITORS AND PROMOTERS OF THE INFLAMMATORY RESPONSE
6. LEUKOCYTES ROLL ON A SELECTIN AT PHYSIOLOGIC FLOW RATES: DISTINCTION FROM AND PREREQUISITE FOR ADHESION THROUGH INTEGRINS
   6.1. RESULTS
      6.1.1. RECONSTITUTION OF CD62 AND ICAM-1 IN LIPID BILAYERS
      6.1.2. THE SELECTIN CD62 IS DISTINCTIVE IN SUPPORT OF ADHESION AT VENULAR LEVELS OF SHEAR STRESS
      6.1.3. NEUTROPHILS ROLL ON CD62
      6.1.4. ADHESION UNDER STATIC CONDITIONS
      6.1.5. COOPERATION BETWEEN SELECTIN AND INTEGRIN ADHESION MECHANISMS
   6.2. DISCUSSION
   6.3. EXPERIMENTAL PROCEDURES
      6.3.1. MONOCLONAL ANTIBODIES
      6.3.2. PURIFICATION OF ICAM-1 AND CD62
      6.3.3. PREPARATION OF LIPOSOMES
      6.3.4. PREPARATION OF PLANAR BILAYERS
      6.3.5. DETERMINATION OF SITE DENSITIES
      6.3.6. ISOLATION OF POLYMORPHONUCLEAR LEUKOCYTES
      6.3.7. LAMINAR FLOW ASSAYS
      6.3.8. DETACHMENT ASSAYS
      6.3.9. ANALYSIS OF NEUTROPHIL ROLLING

1. INTRODUCTION

The present invention related to in vitro models of the in vivo rolling and arrest of leukocytes along the endothelial cell wall, an important part of the inflammatory response. The invention also relates to apparatuses and methods for collecting, purifying, and analyzing blood and blood components, and methods for identifying inhibitors or promoters of components of the inflammatory response.

2. BACKGROUND OF THE INVENTION

2.1 Leukocyte Extravasation

The migration of leukocytes (white blood cells) out of the blood and into tissues (extravasation) is the central event in the inflammatory response. Leukocyte emigration is responsible for the successful host response to tissue injury and infection, but is also potentially harmful and contributes to the pathology of many diseases and inflammatory disorders.

Lymphocytes exit from the blood by selective interaction with high endothelial venule (HEV) cells. In autoimmune disease and inflammation, most lymphocyte extravasation occurs through nonspecialized endothelium rather than HEV. Recirculating lymphocytes express homing receptors which interact in an organ-specific manner with HEV in peripheral lymph nodes, mucosa-associated lymphoid tissues, and in inflamed joint tissue (Jalkanen et al., 1987, Ann. Rev. Med. 38: 467–476). Related receptors are expressed on other leukocyte subsets (id.). The first step in leukocyte migration into tissues is margination, when leukocytes leave the central stream of flowing blood cells in a postcapillary venule and roll along the endothelial lining of the vessel (Cohnheim, 1889, Lectures on General Pathology: A Handbook for Practitioners and Students (London: The New Sydenham Society)). Leukocytic margination in postcapillary venules should be distinguished from the "marginating pool" of about 50% of leukocytes that may be in capillary beds in the lung or tissues and enter the circulation in response to exercise or epinephrine. Postcapillary venules are major sites of leukocyte emigration in inflammation, and there are few or no marginating leukocytes in these venules in the healthy state (Fiebig et al., 1991, Int. J. Microcirc. Clin. Exp. 10: 127–144).

As observed more than 100 years ago using intravital microscopy (Cohnheim, 1889, Lectures on General Pathology: A Handbook for Practitioners and Students (London: The New Sydenham Society)), leukocytes begin to interact with the vessel wall by rolling along the endothelium within minutes after injury to adjacent tissue. The rolling response is seen throughout Vertebrata, in cold-blooded animals such as amphibians as well as in mammals (Cohnheim, 1889, Lectures on General Pathology: A Handbook for Practitioners and Students (London: The New Sydenham Society)). The number of rolling cells increases dramatically during the course of an inflammatory reaction (Atherton and Born, 1972, J. Physiol. 233: 157–165) and is important in the accumulation of cells at the site (Fiebig et al., 1991, Int. J.

Microcirc. Clin. Exp. 10: 127–144). As the inflammatory reaction progresses, the endothelium becomes paved with leukocytes, and their rolling decreases in velocity and is interrupted by halts until they come to a firm stop (Cohnheim, 1889, Lectures on General Pathology: A Handbook for Practitioners and Students (London: The New Sydenham Society)). Throughout this process the cells remain round, but undergo a dramatic change in shape immediately upon initiation of emigration. A pseudopod is extended through the vessel at a junction between endothelial cells, and this often is accompanied by a flattening of the leukocyte against the vessel wall (Marchesi, 1961, Q. J. Exp. Physiol. 46: 115–133). Transmigration continues as the pseudopod grows in ramifications and size until the entire cell body has emerged through a narrow gap between endothelial cells (Cohnheim, 1889, Lectures on General Pathology: A Handbook for Practitioners and Students (London: The New Sydenham Society)). Cells appear to reach the point at which they emigrate by rolling; no active migration along the vessel wall is evident by intravital microscopy.

Both the rheology of blood and specific adhesive interactions may regulate the rolling response. Hydrodynamic studies of particles in suspension show that in Poiseuille flow, the larger particles are forced to the center of the stream, and this effect is more pronounced as shear forces increase (Segre and Silberberg, 1962, J. Fluid Mech. 14: 136–157). This effect has been confirmed for blood cells both in vivo and in vitro; the larger leukocytes are forced to the center of the stream in normal flow (Goldsmith and Spain, 1984, Microvasc. Res. 27: 204–222; Nobis et al., 1985, Microvasc. Res. 29: 295–304). In inflammation, vessels dilate and flow is slowed. Vascular permeability is increased, leading to plasma leakage and an increased hematocrit, and together with slower flow, leads to erythrocyte rouleaux formation. A combination of these factors causes leukocytes to be displaced to the marginal region of flow near the vessel wall (Chien, 1982, Adv. Shock Res. 8: 71–80). This makes contact of a circulating leukocyte with the vessel wall more probable, but shear forces acting on the leukocyte at the vessel wall oppose adhesion to the endothelium. The velocity profile of a vessel shows no flow at the vessel wall and a parabolic increase toward the centerline. Because fluid velocity increases with distance from the wall, cells near the wall have torque exerted on them and will tumble even if not in contact with the wall. However, the velocity at which cells tumble in a shear flow near to the vessel wall is much faster than observed for rolling cells in inflammatory reactions, suggesting that adhesive interactions occur between the leukocyte and vessel endothelium (Atherton and Born, 1973, J. Physiol. 233: 157–165).

More than 100 years after Cohnheim (1889, Lectures on General Pathology: A Handbook for Practitioners and Students (London: The New Sydenham Society)) postulated molecular changes in vessel endothelium in inflammation, the molecular basis of leukocyte rolling remains unknown. However, three families of adhesion receptors that participate in leukocyte interactions with endothelium have been defined: the integrin, immunoglobulin-related, and selectin molecules (reviewed in Springer, 1990, Nature 346: 425–433)).

The integrins LFA (lymphocyte function-associated antigen)-1 and Mac-1 on the neutrophil bind to the Ig family member ICAM (intercellular adhesion molecule)-1 on endothelium (Smith et al., 1988, J. Clin. Invest. 82: 1746–1756; Smith et al., 1989, J. Clin. Invest. 83: 2008–2017; Diamond et al., 1990, J. Cell Biol. 111: 3129–3139). LFA-1 and not Mac-1 binds to ICAM-2 (de Fougerolles et al., 1991 J. Exp. Med. 174: 253–267; Diamond et al., 1990, J. Cell Biol. 111: 3129–3139), an endothelial cell molecule that is more closely related to ICAM-1 than these molecules are to other Ig superfamily members (Staunton et al., 1989, Nature 339: 61–64). Stimulation of neutrophils with chemoattractants is required to activate binding of these integrins to ICAM-1 (Smith et al., 1989, J. Clin. Invest. 83: 2008–2017; Diamond et al., 1990, J. Cell Biol. 111: 3129–3139). Stimulation of neutrophil integrin avidity is a rapid response occurring in minutes, does not require increased integrin surface expression (Buyon et al., 1988, J. Immunol. 140: 3156–3160; Philips et al., 1988, J. Clin. Invest. 82: 495–501; Vedder and Harlan, 1988, J. Clin. Invest. 81: 676–682; Lo et al., 1989, J. Exp. Med. 169: 1779–1793), and appears analogous to an increase in avidity described for LFA-1 on T lymphocytes in response to antigen receptor crosslinking (Dustin and Springer, 1989, J. Cell Biol. 107: 321–331).

ICAM-1 induction is a second mechanism for regulating inflammatory cell interactions that occurs on a time scale of hours and requires mRNA and protein synthesis (reviewed in Springer, 1990, Nature 346: 425–433). ICAM-1 is expressed basally on endothelial cells but is greatly increased at inflammatory sites and by stimulation with lipopolysaccharide and cytokines such as IL-1 and TNF. By contrast to ICAM-1, ICAM-2 is expressed at higher surface density on resting endothelium but is not inducible (de Fougerolles et al., 1991, J. Exp. Med. 174: 253–267).

LFA-1 and Mac-1 together with p150,95 comprise the leukocyte integrins, a subfamily of integrins that share a common β subunit (CD18) and have distinct αL, αM and αX (CD11a, b and c) α subunits (reviewed in Larson and Springer, 1990, Immunol. Rev. 114: 181–217; Springer, 1990, Nature 346: 425–433). They are required for leukocyte emigration as demonstrated by an absence of neutrophil extravasation 1) in patients with mutations in the common β subunit (leukocyte adhesion deficiency), and 2) after treatment of healthy neutrophils with a monoclonal antibody (mAb) to the common β subunit in vivo or in vitro (reviewed in (Anderson and Springer, 1987, Ann. Rev. Med. 38: 175–194; Larson and Springer, 1990, Immunol. Rev. 114: 181–217). Patient neutrophils, and healthy neutrophils treated with mAb to the common β subunit or a combination of mAb to LFA-1 and Mac-1 α subunits, are deficient in binding to endothelial cells in static adhesion assays (Buchanan et al., 1982, Blood 60: 160–165; Harlan et al., 1985, Blood 66: 167–178). However, when binding of neutrophils in shear flow is measured, the leukocyte integrin-dependent component of binding is lost at a shear stress below the physiologic range (Lawrence et al., 1990, Blood 75: 227–237). Nonetheless, patient and CD18-treated cells that bind to the endothelium through other adhesion mechanisms fail to undergo transendothelial migration, in agreement with the lack of neutrophil diapedesis in leukocyte adhesion deficiency (Smith et al., 1988, J. Clin. Invest. 82: 1746–1756).

The integrin VLA-4, that contains the α4 (CD49d) subunit noncovalently associated with the β1 (CD29) subunit, is expressed by lymphocytes, monocytes, and neural crest-derived cells, and can interact with vascular cell adhesion molecule-1 (VCAM-1) (Elices et al., 1990, Cell 60: 577). Like ICAM-1 and ICAM-2, VCAM-1 is a member of the immunoglobulin (Ig) superfamily (Osborn et al., 1989, Cell 59: 1203), but unlike the ICAMs, VCAM-1 is not expressed by lymphocytes (Wellicome et al., 1990, J. Immunol. 144: 2558; Rice et al., 1990, J. Exp. Med. 171: 1369). VCAM-1 expression is very low or absent on resting endothelial cells in culture but can be induced by cytokines such as TNF or IL-1 with kinetics of induction similar but not identical to that of ICAM-1 (Wellicome et al., 1990, J. Immunol. 144: 2558; Carlos et al., 1990, Blood 76: 965). Peak expression of VCAM-1 after continuous treatment of endothelial cells with TNF in culture occurs somewhat earlier than the peak expression of ICAM-1, but both persist at levels substantially higher than basal expression for at least 48 hr (Carlos et al., 1990, Blood 76: 965). Unlike LFA-1, however, VLA-4 can also interact with fibronectin, binding to the alternatively spliced CS-1 region located C-terminal to the RGD site of fibronectin recognized by the integrin VLA-5 (Guan and Hynes, 1990, Cell 60: 53; Wayner et al., 1989, J. Cell Biol. 109: 1321; Hemler, 1990, Annu. Rev. Immunol. 8: 365). Two forms of VCAM-1 cDNA clones, which most likely represent alternatively spliced products, have been reported (Osborn et al., 1989, Cell 59: 1203; Polte et al., 1990, Nucl. Acids Res. 18: 5901; Cybulsky et al., 1991, Am. J. Pathol. 138: 815; Hession et al., 1991, J. Biol. Chem. 266: 6682).

The selectins are the most recently recognized class of leukocyte adhesion molecules (reviewed in Springer, 1990, Nature 346: 425–433). They have an N-terminal lectin domain, one epidermal growth factor-like module, and from two to nine short consensus repeats. By contrast to integrins and immunoglobulin (Ig) family members, selectins have been found to date only on circulating cells and the endothelium, suggesting that they may be specialized for interactions within the vasculature. CD62 (PADGEM or GMP-140) is expressed in α granules of platelets and Weibel-Palade bodies of endothelial cells, and is mobilized to the plasma membranes of these cells after activation by mediators of inflammation and hemostasis, allowing these cells to bind neutrophils and monocytes at the site of tissue injury (Larsen et al., 1989, Cell 59: 305–312; Geng et al., 1990, Nature 343: 757–760). CD62 is rapidly unregulated on the endothelial cell surface, suggesting that it may be important early in inflammation (Hattori et al., 1989, J. Biol. Chem. 264: 7768–7771; Geng et al., 1990, Nature 343: 757–760). ELAM-1 is synthesized by endothelial cells in response to inflammatory agents and promotes adhesion of neutrophils, monocytes, and a subpopulation of lymphocytes (Bevilacqua et al., 1989, Science 243: 1160–1165; Picker et al., 1991, Nature 349: 796–798; Shimizu et al., 1991, Nature 349: 799–802). The LAM-1 or LECAM-1 molecule is expressed on leukocytes and facilitates their binding to endothelium during lymphocyte recirculation through peripheral lymph nodes and neutrophil emigration at inflammatory sites (Jutila et al., 1989, J. Immunol. 143: 3318–3324; Spertini et al., 1991, Nature 349:691–694; Watson et al., 1991, Nature 349: 164–167). Carbohydrate ligands for selectins have recently been defined (reviewed in Springer and Lasky, 1991, Nature 349: 196–197); that for CD62 has Lewis x as an important component (Larsen et al., 1990, Cell 63: 467–474) and also appears to be sialylated (Moore et al., 1991, J. Cell Biol. 112: 491–499). Neutrophils bear Lewis x both on glycolipids and at the termini of N- and O-linked oligosaccharides (Symington et al., 1985, J. Immunol. 134: 2498–2506; Fukuda et al., 1984, J. Biol. Chem. 259: 10925–10935). Antibodies to selectins and integrins additively inhibit neutrophil adhesion to endothelium, suggesting that they mediate distinct adhesion mechanisms (Luscinskas et al., 1989, J. Immunol. 142: 2257–2263; Dobrina et al., 1989, Immunology 67: 502–508; Smith et al., 1991, J. Clin. Invest. 87: 608–618; Hallmann et al., 1991, Biochem. Biophys. Res. Commun. 174: 236–243). The molecular basis of rolling does not appear to involve the leukocyte integrins, based on the inability of Mab to the leukocyte integrin common CD18 β subunit to inhibit rolling in vivo (Arfors et al., 1987, Blood 69: 338–340).

Chemoattractants bind to serpentine family receptors on the surface of a leukocyte. A highly selective class of chemoattractants described in the last few years are small proteins of 70 to 80 amino acids that belong to a recently described protein family called the intercrines (Oppenheim et al., 1991, Ann. Rev. Immunol. 9: 617–648). The chemoattractant receptors mediate pro-inflammatory and chemotactic actions, and transduce ligand-mediated signals through interactions with G proteins (GTP-binding proteins). Actions mediated by chemoattractant receptors include stimulation of granule-enzyme release and superoxide anion production, upregulation of expression and activity of the cell adhesion molecule Mac-1 (CDIIb, CD18), increased expression of CR1, a decrease in cell surface glycoprotein 100MEL-14 on neutrophils (Gerard and Gerard, 1991, Nature 349: 6–14), and stimulation of neutrophil adherence to and emigration through activated endothelial cells (Huber et al., 1991, Science 254: 99). Interleukin (IL-8) can also act as an adhesion or migration inhibitor when added on the same side of activated endothelium as neutrophils (Huber et al., 1991, Science 254: 99; Gimbrone et al., 1989, Science 246: 1601). In vivo, these receptors may participate in anaphylactoid and septic shock (Gerard and Gerard, supra).

The best characterized chemoattractant receptor is the one which binds formylpeptides. cDNAs encoding receptors for four chemoattractants, formylpeptide [e.g. fMet-Leu-Phe (fMLP)] (Boulay et al., 1990, Biochem. Biophys. Res. Commun. 168:1103–1109; Boulay et al., 1990, Biochemistry 29:11123–11133), C5a (Gerard and Gerard, 1991, Nature 349: 614–617) platelet activating factor (PAF; Honda et al., 1991, Nature 349: 342–346), and IL-8 (Holmes et al., 1991, Science 253: 1278–1280) have been cloned.

Citation of a reference herein shall not be construed as an admission that such reference is prior art to the present invention.

2.2. Separation of Blood and Blood Components

Various practices have been developed for separating whole blood and blood components. Generally, whole blood comprises red blood cells (RBC), platelets, and white blood cells of various types known collectively as leukocytes. Red blood cells and platelets can be separated from whole blood by centrifugation, leaving the blood product plasma.

Removal of leukocytes to low levels in a blood sample is desirable to prevent diseases caused by transfusion of blood that contains donor leukocytes. These diseases include viral infections transmitted by leukocytes harboring viruses and infections in which the transfused leukocytes elicit alloantibodies that cause transfusion reactions. Moreover, enrichment of leukocytes is also desirable when different types of leukocytes are needed for a variety of clinical and research purposes.

Nevertheless, currently used methods are problematic for depleting, extracting and identifying leukocyte populations in blood. Centrifugal methods for separating blood do not entirely separate out the leukocytes; they may be present in substantial quantities in both the packed red blood cells and the platelet-concentrate fractions. Centrifugal methods are somewhat costly and the sterility of the product is such that it must be used within a short period of time. A number of other devices have been proposed in which fibers are packed into housings and whole blood allowed to pass through them in order to remove a portion of the white cell content. Typically, these devices are based on size separation but the various types of leukocytes are not widely divergent in size and most of these cells can deform so as to pass through much smaller openings than their normal size. Accordingly, removal of leukocytes can be accomplished by absorption in conjunction with filtration. Attempts have been made to reduce leukocyte concentration in blood by exposure to a variety of surfaces, including polyamide, polyester, acrylics, cellulosics, cellulose acetate and siliconized glass wool. Devices of this type have been only partially successful, primarily because many leukocytes become activated by the act of absorbing or binding to the fibrous material. Even when activated, many of the leukocytes will not adhere to the fibrous material at physiologic flow rates.

A need exists to develop a quick and effective method for concentrating and purifying leukocytes that can be used in research and clinical settings for identification, differentiation, and analysis of leukocyte populations.

3. SUMMARY OF THE INVENTION

The present invention provides in vitro models of the in vivo rolling and arrest of leukocytes along the endothelial cell wall, which are important steps in the migration of leukocytes out of the blood stream and into tissue, as part of the inflammatory response. The in vitro models of the invention provide a physiologically relevant model of such interactions, since the apparatuses of the invention can reproduce in vitro the sequential molecular interactions that are steps in leukocyte accumulation at an inflammatory site in vitro; and, furthermore, function under physiologic flow conditions resulting in physiologic shear stresses similar to those present in vivo at the sites of leukocyte transendothelial migration (extravasation).

Apparatuses embodying and methods relating to the in vitro models of the invention are also provided. Apparatuses embodying the models of the invention provide quick and effective methods for collecting, purifying, and analyzing leukocyte populations and subpopulations. In a specific embodiment, for modelling leukocyte rolling, the apparatus of the invention comprises a solid phase surface with rolling mediator molecules present thereon. Such rolling mediators are, for example, selectins and selectin ligands which have binding partners expressed on leukocytes. In another specific embodiment, for modelling leukocyte rolling followed by adhesion/arrest, the apparatus of the invention comprises a solid phase surface with both rolling mediators and integrin binding partners present thereon. The apparatuses of the invention can be used for collecting, concentrating, purifying, and analyzing blood and blood components, in particular, leukocytes and subsets thereof. Therapeutic and diagnostic methods based on the foregoing are also provided.

The invention further relates to methods for identifying inhibitors or, alternatively, promoters (agonists, functional components) of the processes of leukocyte rolling and adhesion, important components of the inflammatory response. Pharmaceutical compositions and kits are also provided.

4. DESCRIPTION OF THE FIGURES

FIG. 1. A Schematic Illustration of Leukocyte Rolling on a Substrate Containing a Selectin.

Figure 2:
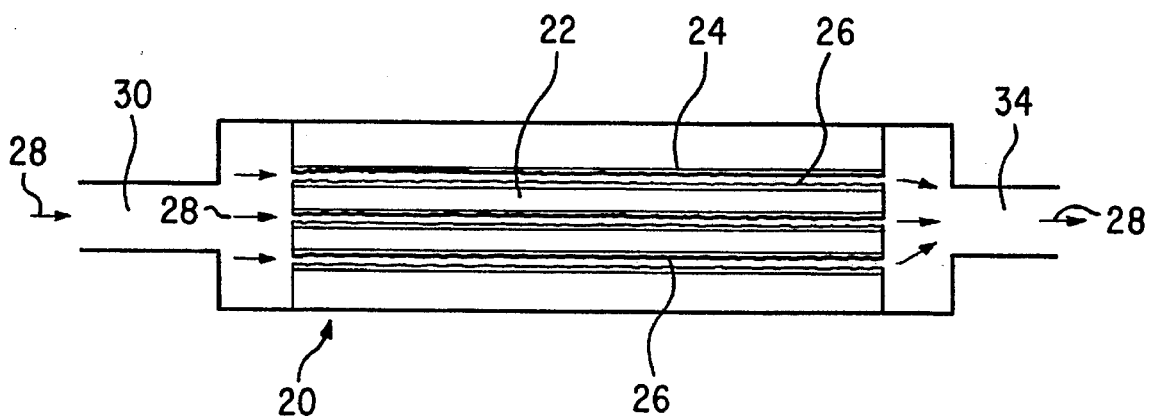

FIG. 2. A Schematic Cross-Section of an Apparatus of the Invention.

Figure 3:
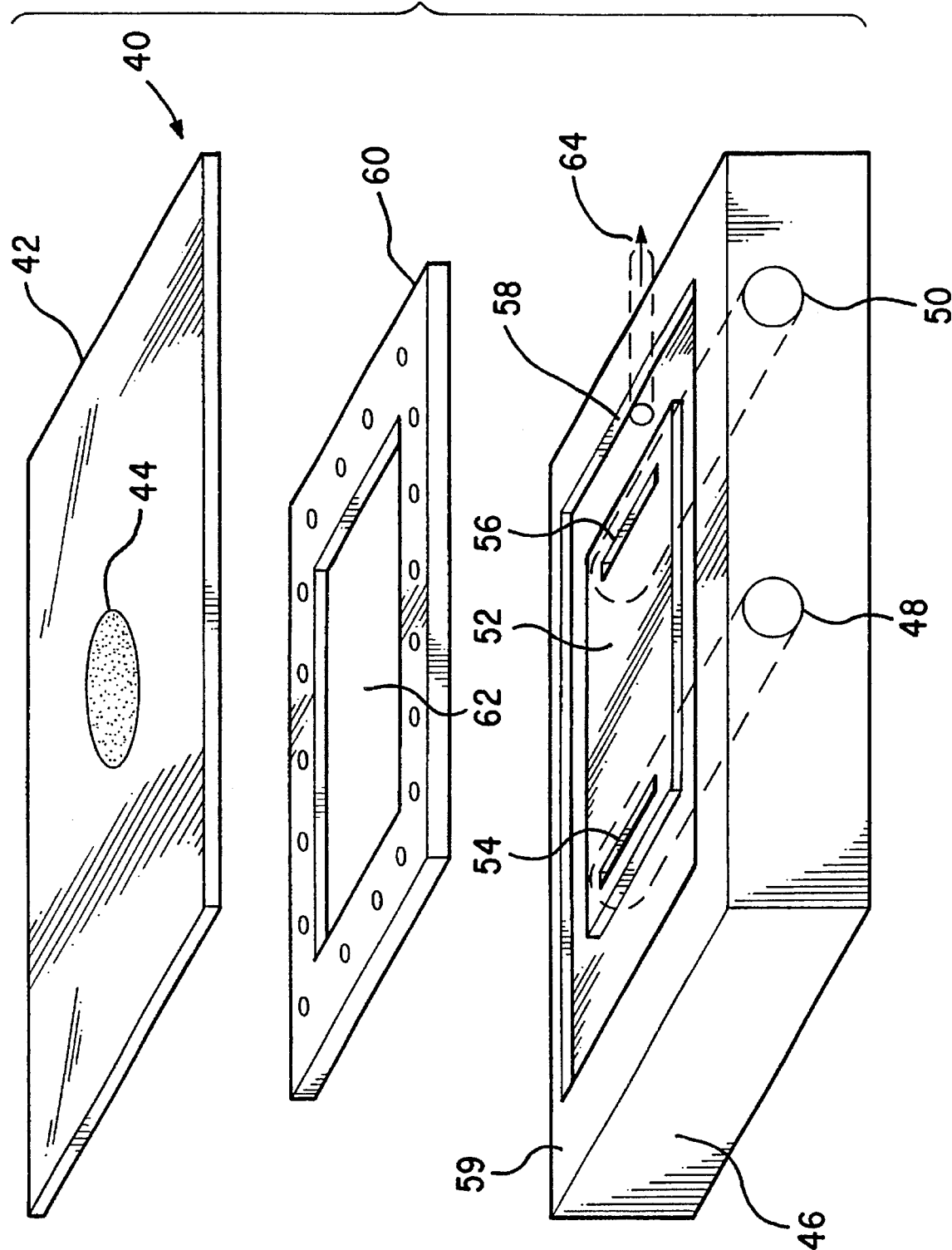

FIG. 3. A Schematic Perspective Illustration of an Embodiment of an Apparatus of the Invention. The apparatus shown is a parallel plate flow chamber, after Lawrence et al. (1987, Blood 70: 1284–1290), for measuring attachment of neutrophils under flow conditions. The chamber is shown upside down for illustration purposes; the glass slide with the artificial bilayer formed the lower parallel plate. It was mounted on the stage of an inverted microscope equipped with a video camera. The cell suspension was connected to the inlet manifold and a syringe pump to the outlet manifold.

Figure 4:
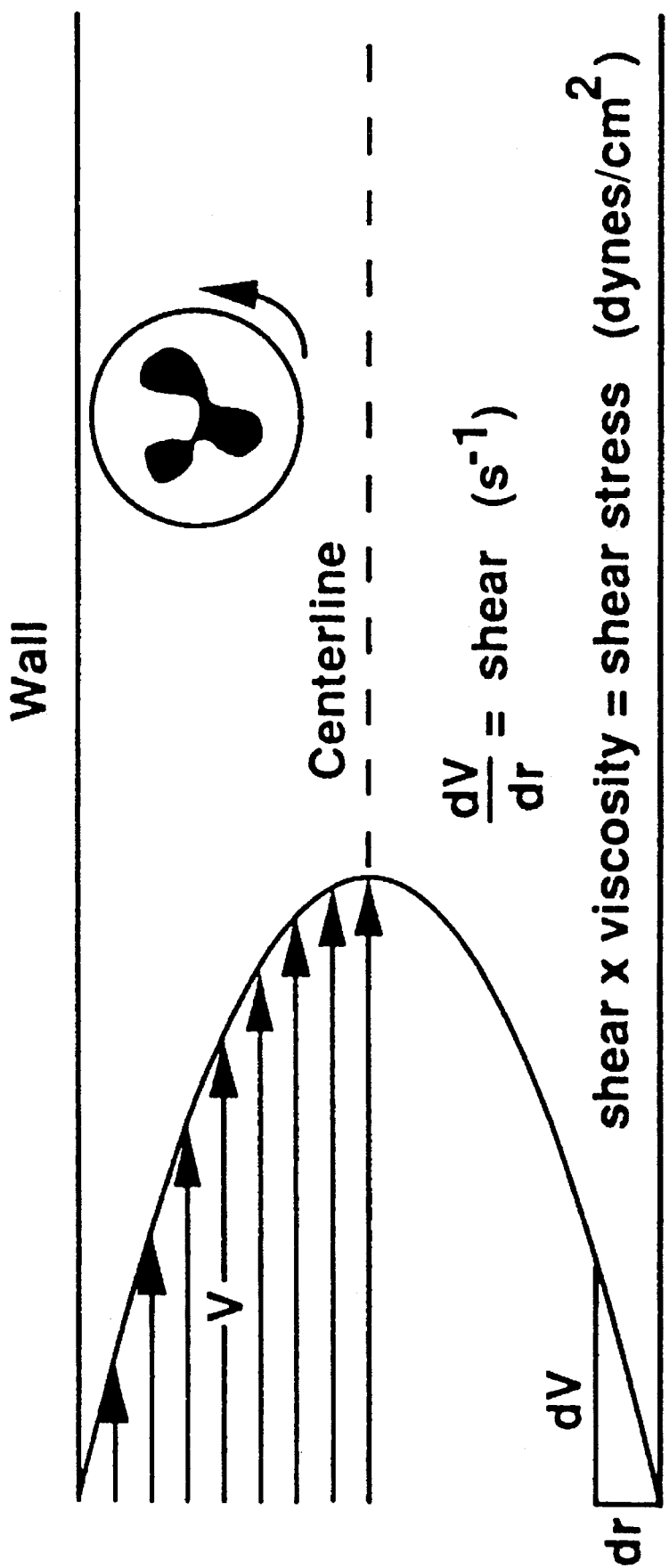

FIG. 4. Schematic of parabolic flow profile in a blood vessel or parallel plate flow chamber.

FIG. 5. Attachment of Neutrophils to Artificial Planar Bilayers during Flow. Resting or PMA-stimulated neutrophils were infused at varying wall shear stresses through the parallel-plate flow chamber. A planar membrane containing CD62, ICAM-1, or both at the density indicated below was formed on one side of the chamber. After 3 minutes of continuous flow to equilibrate adherence and deadherence to the bilayer, adherent neutrophils were quantitated. (A) and (B) represent two different sets of experiments: day-to-day variation throughout this work was slight as exemplified by binding of unactivated neutrophils to CD62 at 200 sites per $\mu m^2$ in both panels. Data are averaged from four to six (A) and two (B) experiments. Bars show the standard error of the mean (SEM) of the experiments. At the next higher experimental point, at 7.3 $dyn/cm^2$, binding was zero in all cases. (A) open circles: CD62 at 400 sites per $\mu m^2$; closed circles: CD62 at 200 sites per $\mu m^2$; closed triangles: CD62 at 50 sites per $\mu m^2$; closed squares: CD62 at 25 sites per $\mu m^2$; open squares: ICAM-1 at 1000 sites per $\mu m^2$. Cells were either unstimulated (solid line) or PMA-stimulated (broken line). (B) closed circles: CDE62 at 200 sites per $\mu m^2$; closed squares: ICAM-1 at 250 sites per $\mu m^2$; closed triangles: CD62 at 200 sites per $\mu m^2$ plus ICAM-1 at 250 sites per $\mu m^2$. Cells were either unstimulated (solid line) or PMA-stimulated (broken line).

FIG. 6. Accumulation and Rolling of Neutrophils on Artificial Bilayers Containing CD62 Compared with Lack of Interaction with Bilayers Containing ICAM-1. (A) Neutrophils infused at a shear stress of 1.8 $dyn/cm^2$ accumulated and rolled on a bilayer containing 200 sites/$\mu m^2$ of CD62 (20×objective). Rolling neutrophils are visualized as round distinct cells by the video camera because their rolling velocity (5.2 $\mu m/s$ here) is slow compared to the exposure time (30 frames per s). By comparison, nonadherent neutrophils tumbling in the shear flow appear as blurred streaks. The streaks of cells closest to the bilayer are short because laminar flow is slowest here. (B) Same as (A), except on a bilayer containing 1,000 sites per $\mu m^2$ of ICAM-1. No rolling cells have accumulated. Nonadherent cells appear as streaks, and those closest to the bilayer have a velocity of about 500 $\mu m/s$. (C-F) Video images at 2 s intervals of neutrophils rolling on a bilayer containing 400 sites per $\mu m^2$ of CD62 at a shear stress of 7.3 $dyn/cm^2$ (40×objective). Nuclei are resolved at this magnification, showing that the cells are rolling rather than sliding. Cells rolled at an average velocity of 8.2 $\mu m/s$; nonadherent cells tumbled too fast (>1700 $\mu m/s$) to be visualized at this flow rate and magnification.

Figure 7:
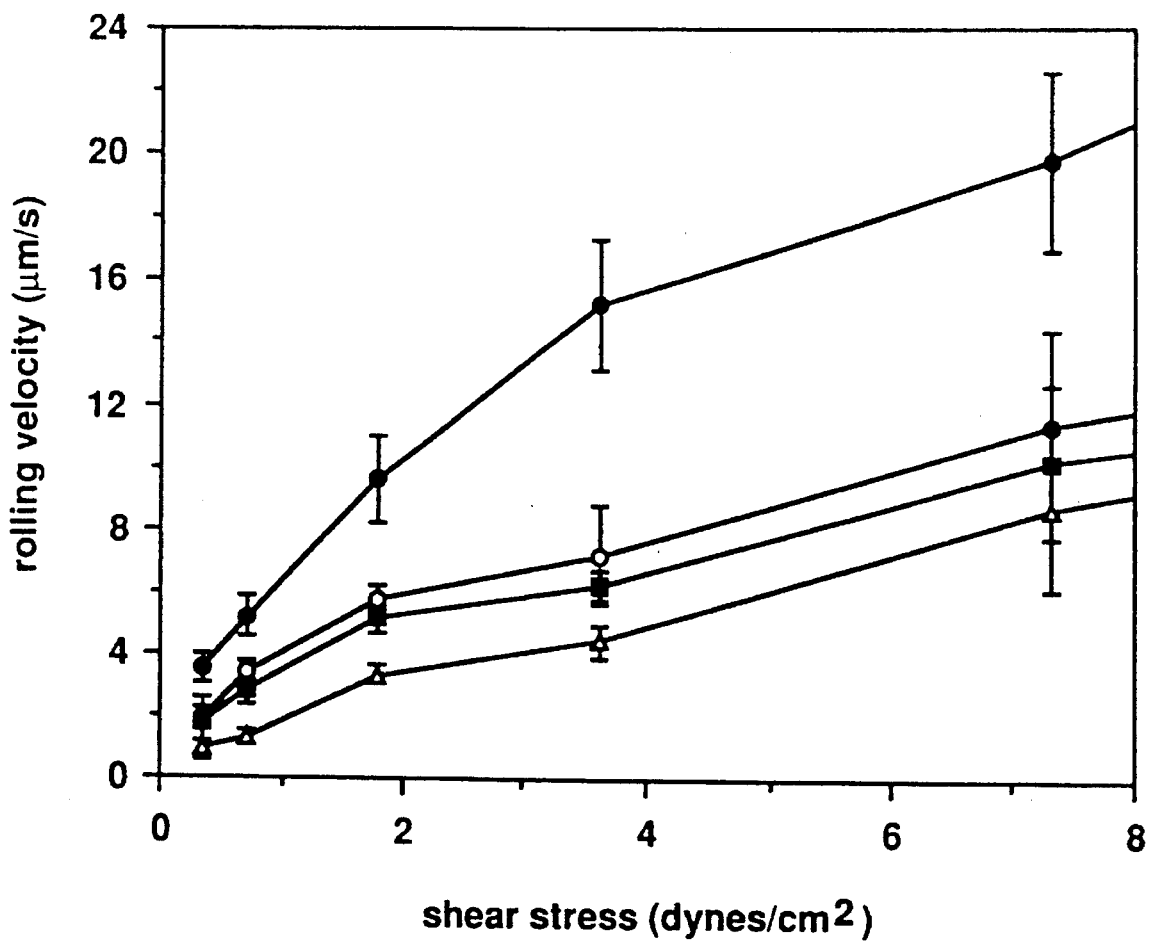

FIG. 7. Rolling Velocity as a Function of CD62 Density and Shear Stress. CD62 and ICAM-1 were used at the density indicated below. Error bars represent the SEM based on measurements from independent experiments. Experimental points at 14.6 $dyn/cm^2$ are not shown, but indicated by connecting lines. Closed circles: CD62 at 50 sites per μm²; open circles: CD62 at 200 sites per μm²; closed squares: CD62 at 200 sites per μm² plus ICAM-1 at 250 sites per μm²; open triangles: CD62 at 400 sites per μm².

FIG. 8. Neutrophils in Contact with Artificial Membranes under Static Conditions. In (A)–(H) neutrophilis, with or without stimulation with PMA, were allowed to adhere in the absence of flow to artificial bilayers containing 250 sites per μm² of ICAM-1 or 200 sites per μm² of CD62 for varying time periods, as indicated. (B)–(F) represent the same field of cells at one minute intervals. Time points prior to 3 min are not shown because it takes 2 min for all cells to settle onto the bilayer.

FIG. 9. Detachment Assay following Static Incubation of Neutrophils on Artificial Membranes Containing either CD62, ICAM-1, or a mixture of CD62 and ICAM-1. Neutrophils were injected through a port in the side of the flow chamber and allowed to settle onto artificial bilayers containing 200 sites per μm² of CD62, 250 sites per μm² of ICAM-1, or both. For some experiments, PMA was added to the neutrophil suspension before it was injected into the flow chamber (broken line). After 6 minutes of contact, shear stress was applied in staged increments. Neutrophils bound after 20 s at each shear stress point are expressed as the percentage of neutrophils that settled onto the bilayer in the initial contact period. Solid lines represent binding of unstimulated neutrophils to the membrane. Broken lines represent binding of PMA-stimulated neutrophils to the membrane. Error bars represent the SEM of three to five independent experiments (A) and two experiments (B). Experimental points at 36 dyn/cm² are not shown but are indicated by connecting lines. (A) closed circles: CD62 at 200 sites per μm²; closed squares: ICAM-1 at 250 sites per μm². (B) closed circles: CD62 at 200 sites per μm²; closed squares: ICAM-1 at 250 sites per μm²; closed triangles: CD62 at 200 sites per μm² plus ICAM-1 at 250 sites per μm².

FIG. 10. Stimulation with FMLP Arrests Neutrophil Rolling on Artificial Membranes Containing both CD62 and ICAM-1. Neutrophils were allowed to adhere to artificial bilayers containing CD62 (200 sites per μm²) and ICAM-1 (250 sites per μm²) during flow at a wall shear stress of 1.8 dyn/cm² (closed circles in (A)) or 0.73 dyn/cm² (open squares in (A)). Rolling velocity was constant for at least 5 min under these conditions. During the experiment, $10^{-9}$M FMLP was added to the medium being infused into the chamber and reached the cells rolling in the field of view 30 or 12 s later (marked 0 time) as verified in another experiment with a dye solution. (A) Mean rolling velocity as a function of time after FMLP addition. Bars show the SEM for two experiments. (B and C) Distribution of rolling velocities of adherent neutrophils with time after FMLP exposure at 0.73 and 1.8 dyn/cm², respectively. (D) Photomicrographs of neutrophils before the infusion of FMLP (0 time) and after exposure to $10^{-9}$M fMLP (5 min) on the same area of the planar membrane. fMLP addition induced arrest and spreading of the neutrophils. Flow was stopped for approximately 30 s to take the photographs in a separate experiment from the two experiments averaged for data in (A)–(C). (E) Shear resistance of neutrophil binding. Neutrophils were allowed to attach at 0.73 dyn/cm² and shear resistance was determined 5 min after fMLP exposure.

5. DETAILED DESCRIPTION OF THE INVENTION

The present invention provides in vitro models of leukocyte rolling and adhesion, which are functional at physiologic shear stresses. The present invention is based in part on the discovery that under physiologic flow conditions, leukocyte rolling mediated by interactions between selectins and their leukocyte binding partners is a prerequisite for chemoattractant-stimulated interaction of integrins on leukocytes with integrin binding partners, that results in arrest of the leukocytes. Thus, leukocyte extravasation appears to involve the following sequential steps: (1) reversible adhesion of flowing leukocytes to the blood vessel wall and subsequent rolling, mediated by interactions between selectins and their carbohydrate ligands; (2) leukocyte activation mediated by binding of chemoattractants, presumably diffusing out of the inflammatory site or expressed on the surface of the endothelium, to their receptors on the leukocyte cell surface; and (3) arrest and stable attachment of the rolling leukocyte mediated by binding of leukocyte integrins to immunoglobulin (Ig) family member molecules on the endothelium.

Apparatuses embodying and methods relating to the in vitro models of the invention are also provided. In a specific embodiment, for modelling leukocyte rolling, the apparatus of the invention comprises a solid phase surface with rolling mediator molecules present thereon. Such rolling mediators include but are not limited to selectins and selectin ligands, expressed on endothelium in vivo, which have binding partners expressed on leukocytes. In another specific embodiment, for modelling leukocyte rolling followed by adhesion/arrest, the apparatus of the invention comprises a solid phase surface with both rolling mediators and integrin binding partners present thereon. The apparatuses of the invention can be used for collecting, concentrating, purifying, and analyzing blood and blood components, in particular, leukocytes and subsets thereof. Therapeutic and diagnostic methods based on the foregoing are also provided. The invention further relates to methods for identifying inhibitors or, alternatively, promoters (agonists, functional components) of the processes of leukocyte rolling and adhesion, important components of the inflammatory response. Pharmaceutical compositions and kits are also provided.

In a specific embodiment of the present invention detailed in the examples sections infra, we show that a selectin is a rolling receptor. We demonstrate that at physiologic shear stress, neutrophils bind to and roll on CD62 in artificial bilayers. We also demonstrate qualitative differences between selectin and integrin adhesion mechanisms, and cooperation between them. On bilayers containing both CD62 and ICAM-1, the rolling interaction through CD62 is a prerequisite for chemoattractant-stimulated interaction of integrins on neutrophils with ICAM-1 that arrests rolling and dramatically strengthens adhesion. This essentially reproduces in vitro the steps of leukocyte accumulation at an inflammatory site in vivo.

5.1. The in vitro Models of the Invention

The present invention provides two general types of apparatuses: one which provides an in vitro model of leukocyte reversible adhesion and subsequent rolling along an endothelial vessel wall in vivo (hereinafter "the rolling model"); and one which provides an in vitro model of leukocyte arrest and stable attachment to the endothelium subsequent to rolling and activation by chemoattractant binding (hereinafter "the arrest model"); both of which models are functional at physiologic shear stresses.

The rolling model comprises a solid phase surface with a rolling mediator present thereon. Interaction of the rolling mediator (preferably, a selectin or selectin ligand) with its binding partner on a leukocyte cell surface, at physiologic shear stresses, mediates reversible attachment and rolling of the leukocyte on the solid phase surface of the rolling model. In a preferred aspect, the rolling model apparatus comprises, on a solid phase, planar lipid bilayers containing the selectin CD62.

The term "rolling" as used herein with reference to a leukocyte, refers to the literal rolling of leukocytes along a surface containing a rolling mediator, which rolling is induced by the interaction of the rolling mediator with the leukocyte in the presence of fluid drag forces arising from relative movement between the surface containing the rolling mediator and a medium containing the leukocytes. This rolling by leukocytes is seen throughout the Vertebrata, in cold blooded animals such as amphibians as well as in mammals. The number of rolling cells in vivo increases dramatically during the course of an inflammatory reaction and is important in the accumulation of cells at the site of injury.

The arrest model comprises a solid phase surface with both a rolling mediator and an integrin binding partner present thereon, both with the same specificity for the leukocyte cell subset of interest (see infra). In the presence of a chemoattractant with matching cellular specificity, and under approximate physiologic shear conditions, interaction of the rolling mediator with its binding partner on the leukocyte leads to rolling of the leukocyte along the solid phase surface, followed by activation due to chemoattractant binding, and stable attachment and arrest of the leukocyte upon interaction of the leukocyte integrin with its binding partner on the solid phase surface. In a preferred aspect, the arrest model apparatus comprises, on a solid phase surface, planar lipid bilayers containing the selectin CD62 and the integrin binding partner ICAM-1; and is preferably used with a formyl peptide such as N-formyl-methionyl leucyl phenylalanine (fMLP) as the activating chemoattractant. In the use of the arrest model, following arrest of the leukocytes on the solid phase surface, the solid phase surface can be removed, and, e.g., the cells present thereon can be released or counted, and new solid phase surfaces inserted within the housing of the apparatus subsequent to use. Alternatively, attached cells can be dissociated from the solid phase surface within the apparatus by exposing them to divalent cation chelating agents such as citrate, EDTA, EGTA, etc., and washed away from the solid phase surface; the surface can then be re-used.

The apparatus of the arrest model can also be used as in vitro model of leukocyte rolling without subsequent arrest, by use of such device in the absence of the activating chemoattractant required for subsequent arrest.

In order to obtain arrest of the desired leukocyte cell subset, a rolling mediator and an integrin binding partner must be present on the surface of the solid phase of the arrest model, and a chemoattractant must be used, that have respective cognate binding partners present on such leukocyte cell subset. Similarly, in order to obtain rolling of a desired leukocyte cell subset in either the apparatus of the rolling model or arrest model, the binding partner for the rolling mediator on the surface of the solid phase of the apparatus must be present on such leukocyte cell subset. Leukocyte cell subsets include but are not limited to neutrophils, eosinophils, basophils, mast cells (collectively known as granulocytes or polymorphonuclear leukocytes), monocytes, macrophages, and lymphocytes (both T lymphocytes and B lymphocytes). For purposes herein, platelets shall also be deemed included within leukocytes, unless clearly excluded by context or otherwise. Exemplary leukocyte cell subset specificities of interactions with various rolling mediators, chemoattractants, and integrin binding partners are described infra. One or more types of rolling mediator molecules may be present on the solid phase surface(s) of the apparatuses of the invention. One or more types of integrin binding partners may be present on the solid phase surface(s) of the arrest model apparatuses of the invention. One or more chemoattractants may be provided in the use of the arrest model to promote leukocyte arrest after rolling.

"Binding partner" of a molecule as used herein refers to a receptor or ligand interacting with such molecule, e.g., by binding or other type of noncovalent association.

Rolling of leukocytes on a solid surface which contains one or more affixed rolling mediators, and arrest of leukocytes on such a surface which also contains one or more integrin binding partners, can occur at physiologic flow rates, and the methods of the invention are designed to produce physiologic flow rates and induce physiologic shear stresses. It is well known that in Newtonian fluids at Reynolds numbers less than 2000, flow is laminar. Furthermore, fluid velocity is zero at the vessel wall and increases parabolically toward the center of the vessel. The change in velocity per change in radial displacement away from the vessel wall is called the shear rate and is highest at the wall. Shear stress scales linearly with the fluid forces acting on a cell under laminar flow conditions and is the product of shear rate and the fluid viscosity.

Preferred shear stresses induced by methods of the invention bracket the range estimated to exist in vivo in post-capillary venules, namely, 0.5–30 dyn/cm$^2$. Wall shear rates and stresses in the apparatus of the invention can be calculated from chamber geometry, volumetric flow rate and viscosity (see, for example, Lawrence et al., 1990, Blood 75: 227–237). Specifically, wall shear stress (T) can be calculated as follows:

$$T=3\mu Q/2ba^2$$

where T=wall shear stress, $\mu$=coefficient of viscosity (cP), Q=volumetric flow rate (cm$^3$/s), a=half channel height, and b= channel width.

The viscosity of water at 37° C. (0.007 poise) can often be used as an approximation of the viscosity of the flow medium. The wall shear rate is given by T/$\mu$. Shear stresses in vivo can be calculated from centerline velocity and vessel diameter using well known equations (see, e.g., Atherton and Born, 1972, J. Physiol. 222: 447–474; Atherton and Born, 1973, J. Physiol. 233: 157–165). Shear is defined according to the following: t,280 shear x viscosity=shear stress (dynes/cm$^2$)

V=velocity; r=radius

Physiologic flow rates are those flow rates sufficient to induce shear stresses in the apparatus of the invention of between about 0.5 to about 30 dynes per square centimeter. Particularly preferred flow rates are sufficient to induce shear stresses of between about 0.5 and about 4.0 dynes per square centimeter, with those in the range of about 0.5–2.0 dyn/cm$^2$ most preferred.

The apparatuses of the invention and components thereof are described in more detail in the subsections below.

5.2. Rolling Mediator Components of the Apparatuses of the Invention

Any rolling mediator known in the art, with a binding partner present on a leukocyte, can be used in the practice of the invention, by providing it on the solid phases of the apparatuses of the invention. As used herein, "rolling mediator" shall mean any molecule capable of interacting with a leukocyte so as to mediate rolling of the leukocyte on the surface containing the rolling mediator. In a preferred aspect, the rolling mediator is a selectin or a binding partner (ligand) of a selectin. Such rolling mediators include but are not limited to those described in Table 1, which also discloses the presently known cell subset specificity of binding partners for such rolling mediators (see also Springer, 1990, Nature 346: 425–433; Springer and Lasky, 1991, Nature 329: 196–197; Butcher, 1991, Cell 67: 1033–1036): t,290

Functional derivatives of the foregoing rolling mediators can also be used.

The binding partner for MECA-79 antigen (lymph node addressin) (Berg et al., 1991, J. Cell Biol. 114: 343) is the homing receptor selectin, also called LAM-1, LECAM-1, or L-selectin, which is expressed on all leukocytes and facilitates lymphocyte binding to endothelium during blood circulation through peripheral lymph nodes and lymphocyte and neutrophil binding to endothelium at inflammatory sites. The ELAM-1 glycoprotein is synthesized by endothelial cells in response to inflammatory agents and promotes adhesion of a variety of leukocytes. The granule membrane protein (CD62), also called PADGEM and GMP-40, is a granule-associated glycoprotein of platelets and endothelial cells that is brought to the cell surface after stimulation by thrombogenic agents, allowing platelets and endothelial cells to bind neutrophils and monocytes at the site of tissue injury.

All known selectins have an N-terminal domain that is homologous to a variety of $Ca^{+2}$-dependent animal lectins (thus the name selectin), one epidermal growth factor (EGF)-like module, and from two to nine short consensus repeats. Molecules composed of short consensus repeats of the type found in selectins have random configurations as revealed by electron microscopy, suggesting a high degree of segmental flexibility. Location of the ligand for selectin is at the termini of long carbohydrate structures on the leukocyte that also may confer flexibility. Thus, the high association and high dissociation rate constants of the selectin-ligand complex required for rolling may be facilitated by the flexible nature of the selectin and its ligand.

The term "rolling mediators" includes molecules that competitively block binding of neutrophils or other leukocytes to rolling mediators such as selectins. Selectin counter-structure ligands have been identified (see Springer and Lasky, 1991, Nature 349: 196–197) and certain molecules are now known to compete with selectins, especially the LAM-1 glycoprotein, for binding sites and thus inhibit binding of selectins to neutrophils. These molecules may thus contain binding sites that are identical, or closely related to, the neutrophil (or other leukocyte) binding site(s) on the selectin glycoprotein. These molecules include fucoidin, sulfatides, polyphosphomannose-ester (PPME) and sulfated glucans and sulfated polysaccharides (e.g. dextran sulfate, xylan sulfate) (see Skinner et al., 1991, J. Biol. Chem. 206: 5371–74).

Rolling mediators can be obtained from any source known in the art, and are preferably purified for use in the apparatuses of the invention. Purification can be carried out by standard methods commonly known in the art, including but not limited to chromatography (e.g., ion exchange, affinity, and sizing column chromatography), centrifugation, differential solubility, or by any other standard technique for the purification of proteins.

For example, blood components containing selectins can be isolated from fresh blood using gel filtration (Larsen et al., 1989, Cell 59: 305–312) or dextran-sedimentation and density separation over Ficoll-Hypaque (Miller et al., 1987, J. Clin. Invest. 80: 535–544). Selectins can be purified from blood components by immunoaffinity chromatography, e.g., by binding to its binding partner or antibody). Briefly, selectins are extracted from cell materials by addition of detergent and, after centrifugation to remove organelles, the crude preparation can be applied to a chromatographic column containing anti-selectin antibody (see Larsen et al., supra). In a particular embodiment relating to CD62 purification, CD62 expression on platelets provides a convenient source for biochemical isolation (id.). ELAM-1 can be purified as described (Lobb et al., 1991, J. Immunol. 147: 124). MECA-79 antigen can be purified as described (Berg et al., 1991, J. Cell Biol. 114: 343).

Recombinant DNA methods using well-known techniques can also be used to prepare purified selectins. Selectins on endothelium have been cloned and sequenced (see Springer, 1990, Nature 346: 425). Chemical synthesis may also be used, which can be automated, e.g., by use of peptide synthesizers.

5.3. Chemoattractants for Use with the Arrest Model Apparatuses of the Invention Use of the arrest model apparatuses of the invention to achieve leukocyte arrest after rolling, comprises providing a chemoattractant to the rolling cell. Any chemoattractant having its receptor present on a leukocyte or leukocyte cell subset of interest, which functions in the arrest model to allow arrest of the leukocyte or the subset thereof, can be used in the present invention. Such chemoattractants can include but are not limited to those presented in Table 2: t,320

In addition to those listed above, any chemoattractants known in the art can be assayed for functional activity in and then used with the arrest model apparatuses of the invention. Such chemoattractants include but are not limited to the following: lymphokines (e.g., interleukin (IL)-i, IL2, IL-4, etc.), collagen, fibrin fragments, oxidized lipid components from cell membranes, histamine (active on eosinophils) (Clark et al., 1975, J. Exp. Med. 142: 1462–1476), eosinophilotactic peptides (ECF-A) (active on eosinophils) (Goetzl and Austen, 1976, J. Exp. Med. 144: 1424–1437), alveolar macrophage-secreted products (active on neutrophils) (Kazmierowski et al., 1977, J. Clin. Invest. 59: 273–281; Hunninghake et al., 1978, Am. Rev. Respir. Dis. 117: 15–23), monocyte chemotactic protein CAP37 (PCT Publication WO 91/00907, published Jan. 24, 1991 by Larrick et al.), other monocyte chemotactic peptides (PCT Publication WO 90/08777, published Aug. 9, 1990 by Yoshimura et al.), lymphocyte chemoattractant factor (LCF; active on $CD4^+$ lymphocytes, monocytes, and eosinophils) (Center and Cruikshank, 1982, J. Immunol. 128: 2569–2574; Rand et al., 1991, J. Exp. Med. 173: 1521–1528), casein (active on lymphocytes, monocytes, and polymorphonuclear leukocytes), cyclic GMP, 1,2-diacylglycerol (Wright et al., 1988, Proc. Natl. Acad. Sci. USA 85: 1869–1873), etc. (for lymphocyte chemoattractants, see Epps, 1982, Agents Actions 12 (Suppl.) 217–233; Berman et al., 1988, Immunol. Invest. 17 (8 & 9): 625–677). Chemoattractants for use should promote chemotaxis, rather than chemokinesis.

The chemoattractants can be obtained from any source known in the art, and are preferably purified for use with the arrest model apparatuses of the invention. Purification can be by standard methods known in the art, including but not limited to chromatography (e.g., ion exchange, affinity, and sizing column chromatography), centrifugation, differential solubility, or by any other standard technique for the purification of proteins.

Chemoattractants can also be prepared by chemical synthetic techniques (e.g., by use of a peptide synthesizer), or by recombinant DNA methods by expression of a cloned chemoattractant nucleotide sequence. For purification procedures and amino acid sequences of various intercrines, see Walz et al., 1991, J. Exp. Med. 1355–1362 (for a review, see Oppenheim et al., 1991, Ann. Rev. Immunol. 9: 617–648); regarding RANTES, see Schall, 1991, Cytokine 3: 165). Various chemoattractants are commercially available. For example, MCP-1 and RANTES can be purchased from Peprotech (Rocky Hill, N.J.); FLMP, LTB4, and PAF are also commercially available. For purification and recombinant expression of C5a, see, e.g., Mandecki et al. (1985, Proc. Natl. Acad. Sci. USA 82(11):3543–3547).

5.4. Integrin Binding Partners in the Arrest Model Apparatuses of the Invention Any molecule known in the art which is a binding partner of a molecule present on a leukocyte, and which mediates leukocyte arrest in the arrest model apparatuses of the invention when such molecule is presented on a solid phase surface of the arrest model, can be used therein. Such molecules are integrin binding partners, which include but are not limited to known Ig family members, normally present on endothelium, such as those listed in Table 3 (see Butcher, 1991, Cell 67: 1033–1036): t,350

Functional derivatives of the foregoing integrin binding partners can also be used, as well as any other integrin binding partners known in the art.

Integrin binding partners are preferably purified prior to use in the arrest model apparatuses, and can be obtained and purified by use of any method known in the art, e.g., by methods as described supra for the rolling mediators. In a particular embodiment relating to ICAM-1, ICAM-1 can be purified as described infra in Section 6.3.2 hereof. Alternatively, cloned ICAM-1 (Staunton et al., 1988, Cell 52: 925–933) can be expressed by recombinant methods known in the art. In another embodiment, a cloned nucleic acid encoding ICAM-2 or a functional derivative thereof (see European Patent Application Publication 387,688, published Sep. 19, 1990 by Springer et al.) can be expressed to obtain ICAM-2. In another embodiment, VCAM-1 cDNA clones (Osborn et al., 1989, Cell 59: 1203; Polte et al., 1990, Nucl. Acids Res. 18: 5901) are expressed.

5.5. Solid Phases of the Apparatuses of the Invention

Many types of solid phases can be employed in the methods and apparatuses of the invention. Preferred solid phases are translucent materials such as glass, plastic, quartz, etc. Well-known solid phases include beads formed from glass, polystyrene, polypropylene, dextran, and other materials, tubes formed from or coated with such materials, or a fibrous support matrix made from one or more of these materials. In preferred embodiments, the solid phase includes planar shapes (e.g., plates, sheets) such as glass or plastic slides or coverslips. In a particularly preferred embodiment, the solid phase includes one or more solid or hollow glass fibers or tubes. These solid fibers or tubes can be packed within a housing or cartridge which preferably contains an inlet and an outlet so that blood containing leukocytes can flow through the cartridge in a unidirectional manner. In another embodiment, the solid phase is plastic.

One or more surfaces of the solid phase(s) can contain the rolling mediators, or rolling mediators and integrin binding partners, as the case may be.

The rolling mediator proteins and integrin binding partner proteins can be placed on the surface of the solid phase in any manner, e.g., by affixing or adsorbing them directly thereto, coating a solution or suspension containing the proteins on the surfaces, etc., as long as the proteins are accessible to leukocytes flowing by the surfaces. In one embodiment, one or more of the desired rolling mediator and/or integrin binding proteins can be either covalently or non-covalently affixed directly to the solid phase by techniques such as covalent bonding via an amide or ester linkage or adsorption. In a particularly preferred method of binding, the rolling mediator and/or integrin binding partner is immobilized by incorporation into lipid bilayers.

Lipid bilayers can be prepared by any method known in the art, e.g., from liposomes. Preparation of liposomes can be achieved by any of several well known procedures (See, for example, Mimms et al., 1981, Biochemistry 20: 833–840). In one embodiment, one or more surfaces of the solid phase is coated with a liposome suspension. The liposome suspension is spread on glass substrates to form planar lipid bilayers containing the incorporated rolling mediators (see also Sections 6.3.3 and 6.3.4 infra), or rolling mediators and integrin binding partners. In a preferred aspect, phosphatidylcholine is used in the preparation of liposomes. Other phospholipids can also be used, including but not limited to phosphatidylserine, phosphatidylinositol, and phosphatidylethanolamine. Furthermore, the lipid vesicles can also contain other lipid-soluble molecules such as cholesterol. By way of example but not limitation, a 7:2 ratio mixture of phosphatidylcholine to cholesterol can be used to make lipid vesicles incorporating the rolling mediators and/or integrin binding partners of the invention (see e.g., Dustin and Springer, 1988, J. Cell Biol. 107: 321). Lipid vesicles incorporating a rolling mediator, alone or in combination with an integrin binding partner, can also be made as described in Smith et al. (1989, J. Clin. Invest. 83: 2008–2017).

In another specific embodiment, the rolling mediators and/or integrin binding partners are affixed to a solid phase such as glass or plastic by direct coating. For example and not by way of limitation, a rolling mediator or integrin binding partner in solution at a concentration in the range of 20–100 µg/ml in 1% octylglucoside detergent, can be diluted 1:10 in Tris-saline (pH 8.0), 2 mM $MgCl_2$ at the time of addition of the solution to a plastic or glass surface, followed by incubation for 16 h at 4° C. to allow the protein to adsorb to the surface, followed by washing of the coated surface with 1% bovine serum albumin in Tris-saline (pH 8.0), 2 mM $MgCl_2$ buffer (see, Dustin and Springer, 1989, Nature 341: 619).

In the practice of the present invention, rolling mediators and/or integrin binding partner proteins present in lipid-vesicle-coated solid phases are preferred over plastic surfaces coated directly with such proteins, which are in turn preferred over glass surfaces coated directly with such proteins, since there is a higher background binding of leukocytes to the solid phase, when the solid phase is glass with directly adsorbed proteins, relative to when the solid phase is plastic with directly absorbed proteins, relative to when the solid phase is a surface coated with lipid vesicles containing such proteins.

5.6. The Apparatuses of the Invention

One embodiment of the rolling model of the present invention is illustrated in FIG. 1 which shows a solid phase 10 upon which is affixed one or more rolling mediators 12. A sample of blood including components 14 (e.g., leukocytes or a subset thereof) which can bind with the rolling mediator and other components 16 (e.g., erythrocytes (red blood cells)) which cannot bind with the rolling mediator, are introduced under conditions providing relative movement between the solid phase 10 and the sample, so that blood components 14 and 16 come into contact with the solid phase 10. Those components 14 that bind to the selectin will contact the solid phase and reversibly adhere thereto. Significantly, these components 14 that bind with the rolling mediator will also begin to roll along solid phase 10 under physiologic flow conditions. The rate of rolling is very slow, on the order of microns per second. Components 16 that are not responsive to the rolling mediator will continue to move rapidly across the solid phase without adhering to it, or tumble along the solid phase, as illustrated by the arrows shown associated with component 16. The rolling velocity of the adhering components 14 is several orders of magnitude slower than the velocity of the freely moving components 16 and this serves as one basis for the separation and purification methods of the invention, as described infra. Components 16 that do not adhere to the solid phase 10 flow out and are removed from the system.

In an embodiment of the invention directed to the arrest model, solid phase 10 also contains an integrin binding partner 17, in addition to the rolling mediator 12. In this embodiment, in the presence of a chemoattractant, the components 14 that (i) bind (or otherwise interact) with the rolling mediator 12 and roll along solid phase 10, and (ii) express a receptor that binds the chemoattractant, and (iii) express an integrin that binds (or otherwise interacts with) the integrin binding partner 17, will become arrested on the solid phase.

In a rolling model embodiment of the invention, an apparatus of the invention comprises (a) a solid phase having a plurality of rolling mediator molecules on a surface of the solid phase; (b) inlet means for receiving a fluid sample and for permitting the sample to enter onto the surface of the solid phase; and (c) outlet means for permitting the fluid sample after it has flowed across at least a portion of the surface of the solid phase to exit said surface. In an arrest model, the solid phase further comprises a plurality of integrin binding partners on its surface. The inlet and outlet means can be entrance and exit slots or holes, channels, tubes, pipes, etc. The apparatuses can further comprise a means associated with the inlet means, for introducing the fluid sample into the inlet means, e.g., ports, injection systems, etc. The apparatuses can further comprise a means associated with the outlet means, for removing a fluid sample from the outlet means, e.g., a pump. Other examples are described infra.

FIG. 2 shows a schematic diagram of one embodiment directed to an apparatus of the rolling model of the invention. A housing 20 contains a plurality of solid glass fibers 22 having affixed on their peripheral surfaces 24 one or more rolling mediators 26. Solid glass fibers 22 can be formed by using well-known procedures. The thickness of the fibers should be as small as possible to maximize the surface in contact with the sample, although the smallest possible fibers are necessarily constrained by mechanical and manufacturing procedures. Blood 28 is introduced via inlet 30 into the housing 20 containing bundled fibers. The fibers may optionally be separated from each other by a plurality of dividers or panels (not shown). The housing can be of any inert material including glass, plastic or other polymer such as polytetrafluoroethylene (PTFE-Teflon®). Blood or other medium containing or suspected of containing blood cells (e.g., whole blood, artificial blood, plasma, heparinized blood, or combinations or components of the foregoing, or other suspending vehicles for blood cells including buffers and the like) continually sweeps over the exterior surfaces 24 of the fibers as the blood moves toward the outlet port 34. Blood can be fed under slight pressure so that the flow will exit the housing through outlet port 34. Alternatively, blood can be introduced into the housing at atmospheric or subambient pressures in which the outlet port 34 is attached to a slight vacuum, the term "vacuum" meaning a pressure lower than the atmospheric pressure. Blood components that are capable of binding to the selectin(s) affixed to the bundled fibers will reversibly adhere to them and roll. Blood components that do not adhere to rolling mediator(s) 26 on the bundled fibers are pulled across the exteriors of the fibers and exit the housing at port 34.

In another embodiment of the invention directed to the arrest model, the peripheral surfaces 24 in FIG. 2 also have affixed thereon one or more integrin binding partners, such that, in the presence of the appropriate chemoattractant, leukocytes which (i) express binding partners for the rolling mediator 26, (ii) express binding partners for the chemoattractant, and (iii) express the integrin recognizing the integrin binding partner, will stop and become arrested on the surfaces 24.

Relative movement of the solid phase and the sample containing or suspected of containing blood cells is accomplished using a variety of methods. For example, bulk flow (i.e., flow of both fluid and particles in the fluid) of a sample can be accomplished by pumping the sample across one or more surfaces of a solid phase containing rolling mediators (or both rolling mediators and integrin binding partners). A peristaltic pump or syringe pump is preferred for this purpose. Relative movement between sample and solid phase can also be provided by capillary action which will draw the sample across one or more surfaces of a solid phase.

Other physical methods that do not rely on bulk flow can include electrophoretic methods in which certain blood cell subpopulations (e.g., T and B cells, neutrophils and monocytes) which differ in their electrophoretic mobility can be exposed to an electric field. The leukocytes will be charged accordingly and will be induced to move within the fluid across an appropriate solid phase.

Other embodiments of the apparatuses of the invention are described infra, e.g., in Section 5.7.1.

5.7. Methods of Blood Collection, Purification and Analysis

The apparatuses of the invention can be used in various methods relating to the collection, purification, concentration, and analysis of blood and blood cells.

In one embodiment, the apparatuses of the invention are used to effect the collection of leukocytes or cell subset(s) thereof. In this embodiment employing a rolling model apparatus, the collection of the leukocytes is accomplished based on the cells' differential mobility (slower speed) in passage across the solid phase of the invention, due to the cells' rolling arising from interaction with the rolling mediator molecules. That is, leukocytes which express a cell-surface binding partner for a rolling mediator (e.g., selectin) present on a solid phase of a rolling model apparatus can be collected from a medium flowing at physiologic flow rates through the rolling model apparatus, by removing the solid phase while such leukocytes are still reversibly adhering and rolling thereon. Alternatively, such cells can be collected by collecting medium after passage over the solid phase at a time subsequent to passage of the non-rolling blood components; however, this method is not preferred, due to the long time period required for passage of the rolling leukocytes over the solid phase (see infra). The type(s) of leukocyte that are collected depends on the cellular specificity of the binding partners for the rolling mediator(s) present on the solid phase (see Table 1, supra).

In an embodiment for collection of leukocytes or cell subset(s) thereof employing an arrest model apparatus, a chemoattractant (or a plurality of chemoattractants) is introduced, preferably by addition to the medium flowing through the apparatus, without stopping flow. Rolling leukocytes that are activated by the chemoattractant, and that express an integrin on their cell surface which interacts with its binding partner on the solid phase of the arrest model apparatus, will become arrested on and strongly adherent to the solid phase. The solid phase can then be removed, and the bound cells eluted for subsequent use (e.g., by exposure to chelating agents such as citrate, EDTA, EGTA, etc.). The type of leukocyte that is collected depends on the cellular specificity of the binding partners for the rolling mediator(s), chemoattractant(s), and integrin binding partner(s) that are used (i.e., what type of leukocyte expresses binding partners for these molecules).

For example, in a specific embodiment directed to a collection method of the invention employing a rolling model apparatus, a blood sample containing leukocytes and a solid phase containing at least one affixed rolling mediator protein are moved relative to each other under physiologic flow conditions. Preferably, the rolling mediator is the selectin CD62. This selectin is specific for neutrophils and monocytes and will not bind to lymphocytes or red blood cells. Nevertheless, it will be understood that a different rolling mediator or more than one rolling mediator can be affixed to the solid phase in order to bind with, and cause adherence of, a different type or a plurality of leukocyte subsets, depending on the cellular specificity of the rolling mediator's binding partner (see Table 1). Moreover, as described supra, a plurality of rolling mediator analogs can also be affixed to the solid phase, such as sulfated glycans, fucoidin, or PPME (polyphosphomannose-ester).

The medium (e.g., blood sample) containing leukocytes is allowed to flow over the substrate at flow rates sufficient to induce a shear stress preferably of between about 0.5 and about 2.0 dynes per square centimeter. At these flow rates, rolling will be induced in the leukocytes that come into contact with the rolling mediator affixed to the solid phase. In vitro rolling velocities of leukocytes on CD62 are comparable to in vivo rolling velocities, as described below in the examples sections. Velocities generally range from under 2 to over 30 microns per second, depending on the site density of selectin and the shear stress. These velocities are several orders of magnitude slow than the fluid velocities necessary to induce the physiologic shear stress. Because these rolling velocities are so small, the rolling leukocytes will not traverse the solid phase of the apparatus under most conditions. For example, leukocytes rolling between 2 and 30 microns per second will traverse a 10 centimeter long substrate in about 1 to 15 hours, for longer than most convenient collection procedures.

After a sufficient number of leukocytes have been accumulated and reversibly adhered to the solid phase, the flow of blood is interrupted and the solid phase is washed to remove any non-adherent material. A particularly preferred washing solution includes saline that contains calcium ions. Calcium ions are preferred because selectins have a N-terminal domain which is homologous to a variety of $Ca^{2+}$-dependent animal lectins and, therefore, selectin binding is calcium-dependent.

After non-adherent material has been washed from the surface of the solid phase, adhering, rolling, leukocytes can be eluted from the solid phase by using a chelating agent such as citrate or ethylenediaminetetraacetic acid (EDTA) to bind calcium ions, thus enabling leukocytes to be released from the solid phase. In a preferred embodiment involving CD62 as the selectin, neutrophils and monocytes can be thus collected.

The above-described embodiment can also be adapted to collect cells using an arrest model apparatus, preferably containing CD62 as the rolling mediator and ICAM-1 as the integrin binding partner and with the use of fMLP as the chemoattractant, for the collection of neutrophils and monocytes.

The above collection methods can also result in and be used for the concentration, purification, and/or quantification of the rolling or arrested leukocytes. Quantification can be by various methods known in the art, including visualization of rolling cells, or staining methods, as described infra.

In the collection methods of the invention, it is not necessary that all the leukocytes within the flow medium that are of the cell subset(s) being collected come into contact with the solid phase, and are actually collected thereby, although the higher the percentage that are thus collected, the more efficient the procedure. In one embodiment, the collection methods of the invention can be used to extract substantially all of the leukocytes or a cell subset thereof from a given volume of medium. Preferably, the total number of leukocytes remaining in the bulk sample is less than $1\times10^6$. The procedure and apparatus of this mode are identical to that described above for collection, except that conditions are chosen so that essentially all of the leukocytes will come in contact with the solid phase. For example, in the flow apparatus of FIG. 2, the distance between the fibers 22 can be adjusted by altering the dimensions and spacing of the fibers. Blood components are then forced to pass through narrower gaps between fibers, which gaps preferably are in the range of from about 10 to about 100 μm (somewhat larger than the width of a typical leukocyte, i.e., 6–7 μm). Moreover, the flow rate can be controlled so that the shear stress is sufficient to allow all the leukocytes to come into contact with the rolling mediator on the solid phase. A preferred shear stress is in the range of from 0.5–2 dynes/$cm^2$. Furthermore, the site density or concentration of selectin on the solid phase can also be increased to accomplish the same ends. A site density of up to about 1,000 sites/$\mu m^2$ can be used, with 100 sites/$\mu m^2$ the preferred site density. These and other design manipulations are well within the knowledge of those skilled in the art.

It will be appreciated that extraction of substantially 100% of given leukocytes or a cell subset thereof in a blood sample or other medium will also serve to concentrate and purify away from such leukocytes the remaining cells (e.g., erythrocytes) and other components that exit from the flow apparatus. Thus, the procedures of the invention can be used to both collect, concentrate and/or purify leukocytes and to concentrate and separate away or purify the remaining components in the flow medium. Both the leukocytes and/or these remaining components can then be used for further testing and/or for transfusion procedures.

The collection and purification methods of the invention are useful in the clinical or laboratory setting. The volume and numbers of leukocytes per volume of blood can be determined by quantitation of the rolling or arrested leukocytes and by measuring the volume of flowing blood. Alternatively, the leukocytes can be eluted from a known blood volume using the apparatus of the invention and their total numbers separately determined using well known methods.

5.7.1. Analysis and Quantitation

In one specific embodiment of an analysis method particularly useful in clinical and diagnostic tests (see Section 5.9 infra) and employing a rolling model apparatus, glass slides containing planar bilayers having one or more rolling mediators immobilized therein are used in a parallel plate flow chamber 40, as illustrated in FIG. 3. The chamber is shown upside down for illustration purposes; under normal conditions the chamber is placed on the stage of an inverted microscope. Glass slide 42 with an artificial lipid layer 44 containing one or more immobilized rolling mediators forms the lower parallel plate. A base 46, typically formed of polycarbonate, contains both inlet manifold 48 and outlet manifold 50. These manifolds are in communication with a deck 52 consisting of an inert material such as glass or polycarbonate. The inlet and outlet manifolds 48, 50 are also in communication with respective entrance and exit slots 54, 56 in the deck. Base 46 contains a recessed lip 58 on an upper surface 59 of the base into which is placed a compressible gasket 60 having an aperture 62, which aperture being sized and shaped to be congruent with the deck 52. Glass slide 42 or other similar planar surface with an artificial bilayer containing one or more rolling mediators is placed on the gasket in communication with the gasket aperture. A vacuum source 64 is connected to the base 46 and this vacuum source applies enough force compress the gasket 60 and slide 42 together and prevent their disengagement from the rest of the base assembly. A cell suspension is connected to the inlet manifold and preferably a syringe pump (not shown) is connected to the outlet manifold.

Another embodiment of an analysis method uses a solid substrate affixed with a plurality of different rolling mediators. Each rolling mediator can be confined to a distinct area or zone of the solid substrate. The rolling mediators are chosen so that each zone will allow adhesion of a different leukocyte cell subset or subsets (e.g., monocyte, neutrophil, eosinophil, basophil, and the like). A blood sample is obtained from a patient and a small amount of blood or other medium containing blood cells is allowed to contact the solid substrate. Leukocytes of various types will bind to the respective rolling mediators. Preferably, the flow can be generated by a syringe or syringe pump, as described above and allowed to flow across the parallel plate chamber of FIG. 3. Alternatively, the substrate, which can be of small size, can be moved through the blood sample to provide relative movement. This is most conveniently done by attaching the solid phase to an elongated member (e.g., a "dipstick") and moving the substrate back and forth within the sample at controlled velocities. Different leukocytes flowing across the substrate will roll and reversibly adhere to their respective rolling mediators and will be physically separated on the substrate. The substrate can be washed, as above, to remove unbound material and the adhering leukocytes stained using fluorescent or other labels well known in the art (e.g., Wright's Crimson).

A further embodiment of an analysis method that utilizes a solid substrate affixed with a plurality of different rolling mediators can include, as described above, a solid phase in which rolling mediators are confined to distinct areas or zones. In particular, the solid phase can include one or more rolling mediators chosen so that substantially all of the leukocytes are concentrated in a particular zone of the solid phase. This initial concentration of leukocytes can take place within a so-called "starting zone." After cells are concentrated onto the starting zone, they can be further separated and analyzed using, for example, subsequent electrophoresis onto a solid phase containing a plurality of different rolling mediators. The different leukocyte populations will then be separated on this so-called "separation zone." Cells can then be counted and analyzed on the separation zone using a variety of conventional methods. For example, the separation zone can be scanned and the absorbance determined, which absorbance is a function of the leukocyte population density. Further, the solid substrate can be viewed under a microscope and numbers of leukocytes, separated by leukocyte subset into distinct "zones", can be counted The slide can be preserved and cells further examined by microscopy if desired.

The foregoing methods of analysis can also be adapted for use with an arrest model apparatus, with provision of the appropriate chemoattractant(s) and integrin binding partner(s).

The apparatuses and methods of the invention can also be adapted to provide for visual analysis of leukocyte rolling velocities. In one embodiment, the parallel flow apparatus of FIG. 3 is attached to a microscope stage, and the blood components flowing across the surfaces are viewed through the microscope objective by way of a video cassette recorder (VCR). Images are recorded on a time-lapse VCR at real time and then played back at slower speed. The location of cells can be marked at any given time and the location of the individual cell is determined at some finite time afterwards.

Visualization of the rolling of different types of leukocytes is thus possible using a VCR in combination with the magnification power of the microscope. The kinds and numbers of leukocytes that rollingly adhere to a substrate can be determined and their individual velocities can be recorded. Optionally, the analysis is completed by constructing a frequency histogram of the numbers of leukocytes (or a cell subset thereof) rolling at a particular velocity. This analysis also results in a determination of the rolling rate of a particular kind (subset) of leukocyte. Rolling leukocytes are visualized as round, distinct cells by the video camera because their rolling velocity is on the order of microns per second, which rolling velocity is extremely slow compared to the exposure time of the VCR camera (typically 30 frames per second). By comparison, non-adherent blood components flowing and tumbling through the apparatus tumble in the shear flow and appear as blurred streaks. Typically, non-adherent cells and those tumbling closest to the solid phase have a velocity of about 500 microns per second. Confirmation of rolling can be determined by visualizing the nuclei of the leukocytes under magnification. Determination of the rotating position of the nuclei distinguishes between leukocytes that merely slide along the surface of the substrate and those that rollingly adhere.

Leukocytes in a given medium, e.g., blood, can optionally be differentiated from erythrocytes prior to introducing the sample into the flow chamber by labelling the leukocytes, e.g., with acridine orange or quinicrine dihydrochloride (see Nobis et al., 1985, Microvasc. Res. 29: 295–304). Alternatively, erythrocytes can be lysed prior to introduction of the labelled leukocytes into a flow chamber of the invention (e.g., by $NH_4Cl$ lysis; see e.g., 1991, *Current Protocols in Immunology*, ch. 3.1, J. E. Coligan et al., eds., John Wiley & Sons). The leukocytes are irradiated under ultraviolet (UV) light. The acridine orange or quinicrine dihydrochloride stain will absorb this radiation and emit light at visible wavelengths (510–540 nm). The positions of leukocytes on the substrate are compared under UV irradiation in successive frames of the VCR recording to determine rolling velocities, and a histogram of velocities is constructed. Each peak in the histogram is associated with a specific cell population that rolls at a particular rate. Other methods of labelling leukocytes or cell subsets thereof can also be used, e.g., by use of an antibody directed to a leukocyte cell surface antigen, which antibody is labeled with a detectable marker.

In a further embodiment of an analysis method, a quartz cell with a hollow bore having an internal diameter between about 50 and about 500 microns is provided. The hollow bore is brought into contact with rolling mediators so that one or more rolling mediators are affixed to the inner wall of the hollow bore. Leukocytes and erythrocytes can be physically separated by lysing the erythrocytes as described above, or leukocytes can be stained with a fluorescent stain, thus differentially tagging them. A blood sample containing leukocytes to be differentiated is allowed to flow through the chamber affixed with one or more rolling mediators, and light of sufficient wavelength to excite the fluorescent label of the leukocytes is directed at the chamber. Emission of light from the rolling cells is determined. The total time interval over which fluorescent energy is received from the excited label on the leukocyte will be a function of its rolling velocity. This is because the light beam width can be made constant (preferably about 50–100 $microns^2$) and the amount of time required for any individual leukocyte to traverse the beam is the beam width divided by the cell velocity. In particularly preferred embodiments of this analysis method, laser light is used. Non-coherent light is also suitable.

Accordingly, one embodiment of a laser-based method comprises providing fluorescently tagged leukocytes and flowing the leukocytes through a tube, the inner surfaces of which contain one or more rolling mediators. The sample is irradiated with laser light and the duration of fluorescent light emitted by each cell of the sample is measured as the cell flows in a direction perpendicular to the optical axis of the laser beam. Leukocytes can be discriminated on the basis of the distribution of signals that are indicative of the intensities of the sensed fluorescent light. The value of emitted light data can be stored using A/D converters in a computer system, or directly visualized with a video camera, such procedures being well known to those of ordinary skill in the art.

These cytometric methods can be calibrated by comparing the velocity of a given, but unknown type of leukocyte, to the velocity of a known type of leukocyte. The methods can also be used to produce a frequency histogram of leukocyte rolling velocities, which can be used in a diagnostic context, as described infra.

5.8. Kits

The apparatuses for carrying out the methods of the invention can be conveniently arranged into kits for use in clinical laboratories and other settings. For example, an apparatus can comprise a solid phase, optionally contained within a housing. This solid phase contains one or more rolling mediators affixed to it, as described above (and, in an arrest model, one or more integrin binding partners). The housing can include a means for withdrawing the sample from an outlet end and a means for introducing sample into an inlet end. In one embodiment of a kit, the apparatus can contain a plurality of solid fibers upon whose cylindrical surfaces are immobilized one or more rolling mediators (and, in an arrest model, one or more integrin binding partners). The fibers can be contained within a cartridge or housing with a means for introducing a fluid sample (e.g., of blood) into the housing and a means for withdrawing the sample from the housing so that the sample flows over the external surfaces of the fibers. The size of fibers, their number, and the site density of rolling mediator can be adjusted to provide for a cartridge having different capacities for accumulating leukocytes, or cell subsets thereof.

Apparatuses for use in diagnostic contexts can also be arranged into convenient kits. For example, a solid phase, such as a microscope slide or coverslip, can be provided that contains a plurality of rolling mediators arranged in spatially distinct zones. The solid phase can be attached to a dipstick or other arrangement such as the parallel flow chamber described above, to provide for relative movement between the solid phase and the sample. In a related embodiment, the solid phase can contain both rolling mediators and integrin binding partners in spatially distinct zones, for use with the addition of a chemoattractant, to promote affixing of the cells, in an arrest model.

Another embodiment of a kit of the invention includes, in one or more containers, the following components of an apparatus of the invention: (a) liposomes or other artificial lipid bilayer components or precursors (e.g., phospholipids such as phosphatidylcholine); and (b) rolling mediator molecules. In a preferred aspect, such a kit comprises, in one or more containers, liposomes and CD62. In an embodiment relating to the arrest model, a kit of the invention comprises, in one or more containers or precursors: (a) liposomes or other artificial lipid bilayer components or precursors; (b) rolling mediator molecules; and (c) integrin binding partners. Such a kit can further comprise a chemoattractant in a container. In a preferred aspect, such a kit comprises, in one or more containers: liposomes, CD62, ICAM-1, and the chemoattractant fMLP.

5.9. Diagnostic and Therapeutic Utilities of the Methods of Collection, Purification, and Analysis of Blood and Blood Components The methods of collection, purification, and analysis of blood and blood components provided by the present invention have diagnostic and therapeutic utilities.

The collection methods can be used to determine the number of leukocytes or cell subset thereof in a sample of blood or other fluid derived from a patient, or the number of leukocytes or cell subset thereof which roll at particular velocities in such a sample. Such number can be compared to the amount present in an equivalent sample from a normal or healthy subject, or a subject in remission from a disease or disorder, or the same patient at an earlier time period, whereby increases or decreases relative to such amount indicate the presence or progression of a disease or disorder, the stage of the disease or disorder, or the response to therapy in such patient, thus providing methods of detection, diagnosis, staging, and monitoring of treatment. Similarly, the methods of the invention can be used to determine a percentage, consisting of the number of leukocytes or cell subset thereof per number of one or more other cell types in the sample, or consisting of the percentage of leukocytes rolling at a particular velocity, which percentage can be similarly compared to the percentage in an equivalent sample from subjects as described above, to detect, diagnosis, stage, and monitor treatment of diseases and disorders. In one embodiment, the numbers of total leukocytes per volume of blood can be used diagnostically. The numbers of leukocytes from a patient with an unknown disease can be compared to the numbers of leukocytes in a blood sample that is characteristic of a disease. Comparison of the two samples can determine the presence or absence of the disease in the patient from whom the original sample is derived.

The diseases or disorders suitable to diagnosis, staging, and/or monitoring in the foregoing methods include those in which there is a disturbance in the normal amount of a leukocyte or cell subset thereof, so that the changed amount is characteristic of a diseased condition. Generally, the number of circulating white blood cells (leukocytes) may be markedly decreased or increased in a variety of clinical disorders.

Disorders involving an increase in leukocytes or a subset thereof include but are not limited to hematologic malignancies such as leukemias, lymphomas, e.g., acute and chronic myeloid and lymphatic leukemias, including chronic myelogenous leukemia, adult T cell leukemia, non-Hodgkins lymphoma, chronic lymphatic leukemia, plasma cell myeloma, etc. In addition, increased levels of eosinophils may occur in asthma or parasitic infections. An increase in the number of white blood cells in circulating blood is due mainly to granulocytosis. The most extreme and important increases are, however, encountered in the various leukemias.

Diseases and disorders involving a decrease in leukocytes or a subset thereof include but are not limited to leukopenias such as neutropenia, Hodgkin's disease, etc. An abnormally low white blood cell count (leukopenia) may occur because of decreased numbers of any one of the specific types of leukocytes within the circulating blood, but most often leukopenia involves the neutrophils. Low lymphocyte counts are much more common and are associated with specific clinical syndromes (e.g., Hodgkin's disease, non-lymphocidic leukemias). Other diseases or disorders involving decreased levels of T lymphocytes include the immunodeficiency disorders congenital thymic aplasia (DiGeorge syndrome) and severe combined immunodeficiency disease (in which both T and B cells may be completely absent), as well as AIDS (Acquired Immune Deficiency Syndrome; involving a decrease in $CD4^+$ T cells).

Additionally, the histograms described in Section 5.7.1, supra, can be used in a diagnostic, staging, or monitoring context. In a specific embodiment, blood samples taken from subjects known to have one or more of the foregoing diseases can be analyzed using the methods of this invention to produce a velocity histogram, and the resulting histogram provides a rolling velocity "fingerprint" that is characteristic of the disease. A blood sample from a patient having an unknown disease is then analyzed using the methods of this invention, and the velocity histogram is compared to this standard "fingerprint" to determine the presence or absence of the disease in the unknown blood sample.

Methods designed to differentiate leukocytes based on rolling induced by interactions with different types of rolling mediators (optionally, in conjunction with arrest induced by chemoattractants and integrin binding partners), also provide a convenient method of determining numbers of different leukocytes.

In addition, apparatuses and methods of the invention can be used in a therapeutic context to monitor the progression of a disease or the progression of therapy by taking frequency spectra or leukocyte rolling velocities from blood samples over a period of time.

In another embodiment, the methods of collection, purification, and analysis of the invention have utility for the diagnosis of diseases and disorders involving a defect in leukocyte rolling, chemoattractant activation, and/or arrest at the endothelial cell wall, by detecting a decrease in the percentage of leukocytes or a cell subset thereof from a patient which are able to roll, or roll and arrest, in the apparatuses of the invention, relative to such percentage of leukocytes from a healthy patient. For example, leukocyte adhesion deficiency (Anderson and Springer, 1987, Ann. Rev. Med. 38: 175–194) involves an inherited deficiency in the integrins LFA-1, Mac-1, and p150,95, resulting in deficient adherence of granulocytes, monocytes, and lymphoid cells, which can be thus detected in an arrest model apparatus (preferably using ICAM-1 as the integrin binding partner). In addition, diabetes mellitus, granulocytasthenia, and recurrent pyogenic infections have been reported to involve cell adherence defects (see Gallin et al., 1980, Ann. Int. Med. 92: 520–538). Genetic defects in leukocyte rolling mediator binding partners, chemoattractant receptors, and/or integrins that interfere with the rolling and/or arrest processes are capable of detection by the methods of the invention. For example, patients whose leukocytes or a subset thereof lack the binding partner or binding partner determinant thereof necessary for interaction with a rolling mediator can be diagnosed by the methods of the invention. In particular, patients whose leukocytes lack GDP-fucose and hence do not bear sialylated Lewis x and therefore cannot bind to E-selectin or CD62, can be diagnosed.

In another embodiment, leukocytes or a subset thereof from a subject, or blood components obtained after passage through an apparatus of the invention and thus deleted of such cells, can be analyzed in vitro by carrying out diagnostic tests known in the art, e.g., analysis for expression of certain cell-surface antigens (e.g., associated with a malignancy or with infection by a pathogenic microorganism), karotype analysis, etc.

In another embodiment, the invention can be used ex vivo in a manner similar to a blood phoresis device. Blood is taken directly from a patient's blood vessel and is allowed to flow into the inlet port of the apparatus of FIG. 2. Various valving arrangements that are well-known to those of ordinary skill in the art may be attached to one or another end of the apparatus to provide for shunting of blood flow away from the apparatus during washing and elution of leukocytes.

In a specific embodiment, citrate anticoagulated whole blood derived from a patient in a clinical setting can be introduced into the apparatuses of the invention and analyzed as described above.

The collection and purification methods of the invention also have therapeutic utility, by providing collected, purified, and/or concentrated blood components which can be administered to a patient, in a transfusion procedure. For example, leukocytes or a subset thereof isolated by the methods of the invention can be administered to a patient suffering from decreased levels of such leukocytes. Alternatively, fluid passed through an apparatus of the invention and thereby substantially deleted or decreased in leukocytes or a subset thereof can be administered to a patient in need of blood or blood components but for whom administration of such leukocytes is not desirable.

The therapeutic and diagnostic methods described herein have application to subjects that are preferably mammals, including cows, dogs, pigs, and most preferably, humans.

5.10. Identification of Inhibitors or Promoters of the Inflammatory Response The apparatuses and methods of the present invention can be used for the identification of inhibitors (e.g., antagonists) or promoters (agonists/functional components or enhancers) of the adhesion receptor-mediated migration of leukocytes through the endothelium (extravasation). Such inhibitors and promoters respectively inhibit and promote the inflammatory response, and thus have therapeutic utilities. The inhibitors and promoters are identified by detecting their abilities to respectively inhibit or promote the rolling of leukocytes or a cell subset thereof in a rolling model apparatus of the invention, or to respectively inhibit or promote the rolling and arrest of leukocytes or a cell subset thereof in an arrest model apparatus of the invention.

Since the present invention provides a simplified physiologically relevant model of the processes leading to leukocyte extravasation, the models of the invention can provide for the identification of inhibitors and promoters of the inflammatory response that are therapeutically useful in vivo.

5.10.1. Identification of Inhibitors

The methods of the invention can be used to identify an inhibitor of the inflammatory response which acts by inhibiting one or more of the steps involved in leukocyte rolling (by use of a rolling model apparatus) or leukocyte rolling and arrest (by use of an arrest model apparatus) in an apparatus of the invention. For example, inhibitors thus identified can inhibit a rolling mediator-binding partner interaction, a chemoattractant-chemoattractant receptor interaction, and/or an integrin-integrin binding partner interaction. The inhibition may be competitive or non-competitive.

An inhibitor of the inflammatory response is thus identified as follows. In a rolling apparatus, the rolling mediator(s) incorporated onto the solid phase surface(s), and the flow medium containing leukocytes, are selected so as to provide for rolling of the leukocytes or one or more cell subsets thereof on the solid phase(s). The molecule to be tested is introduced into the flow medium prior to passage though the apparatus, or preferably, during passage, when leukocytes have begun rolling. A decrease in rolling (e.g., as measured by a decrease in the percentage of leukocytes that are rolling, or a decrease in their velocity, or a decrease in the number of rolling leukocytes per volume) in the presence of the molecule, relative to that observed in the absence of the molecule, indicates that the molecule is an inhibitor of leukocyte extravasation, a component of the inflammatory response.

For identification of an inhibitor, in an arrest model apparatus, the rolling mediator(s) and integrin binding partner(s) incorporated onto the solid phase surface(s), the chemoattractant(s) introduced into the flow medium, and the flow medium containing leukocytes, are selected so as to provide for rolling and arrest of the leukocytes or one or more cell subsets thereof on the solid phase(s). The molecule to be tested is introduced into the flow medium prior to passage through the apparatus, or during passage, when leukocytes have begun rolling. A decrease in arrest of leukocytes (e.g., as measured by a decrease in the percentage of leukocytes that are arrested, or in the number of arrested leukocytes per volume) in the presence of the molecule, relative to that observed in the absence of the molecule, indicates that the molecule is an inhibitor of leukocyte rolling, chemoattractant activation, and/or arrest, and thus an inhibitor of leukocyte extravasation, a component of the inflammatory response.

Molecules to be tested for inhibitory activity can be any of interest, including but not limited to antibodies (preferably monoclonal, most preferably human or humanized monoclonal, or antigen-binding domains thereof) to any member of the following receptor-ligand pairs: rolling mediator-binding partner; chemoattractant-chemoattractant receptor; integrin-integrin binding partner, or a neutralizing epitope thereof, e.g., sialylated Lewis x or GDP-fucose; peptide antagonists and peptidomimetics, etc.

A preferred specific embodiment for testing numerous compounds for inhibitory activity is as follows: As cells are continuously rolling on E-selectin, P-selectin, or the ligand of L-selectin in a parallel plate flow chamber of a rolling model apparatus of the invention, a test compound is injected for some duration of time just upstream of the observation point. The flow brings the compound, with some dilution factor (approximately 2-fold), into the area of observation. Its effect on the percentage of rollingly adherent cells, or their number per volume flow medium, or their velocity, is then measured. Injection is stopped for a sufficient length of time to allow the compound to flow downstream, and for cells to accumulate from upstream and for rolling to reach equilibrium again, then a new compound is injected and the process is continuously repeated. With a cycle time of 2 minutes, it is possible to screen 720 compounds per flow chamber per day. Multiple ports for simultaneous injection of compounds, with injection of buffer in intervening ports to keep the compounds separate in distinctive streams, may be used to increase throughput. The ports are placed perpendicular to the direction of flow and thus the streams are parallel. Cells rolling in each stream may be visualized using multiple microscope objectives or by moving the same objective from one area to another.

5.10.2. Identification of Promoters

The promoters of the inflammatory response detected according to the present invention can act by increasing the efficiency of the adhesion process in an apparatus of the invention, or by acting as a functional component thereof (e.g., a rolling mediator, chemoattractant, or integrin binding partner). Such a functional component is detected by its ability to promote rolling or arrest in a model where this was previously lacking (e.g., due to lack of appropriate cellular specificity of a rolling mediator or integrin binding partner previously present in the apparatus, or lack of any rolling mediator or integrin binding partner). For example, an arrest model apparatus can be used to identify a compound which is a chemoattractant or to identify an integrin binding partner, functional in leukocyte extravasation. A rolling model apparatus or an arrest model apparatus can be used to identify an endothelial cell rolling mediator functional in leukocyte extravasation.

To identify a chemoattractant, an arrest model apparatus is used, in which the rolling mediator and integrin binding partner present on a solid phase thereof have binding partners situated on the leukocytes present in the flow medium to be passed through the apparatus. A sample containing the molecule to be tested for chemoattractant activity is introduced into the flow medium passing through the apparatus, and it is determined whether any leukocytes are arrested on the solid phase. Arrest of leukocytes in the presence of the molecule, but not in its absence, indicates that the tested molecule is a chemoattractant, and that the leukocytes arrested on the solid phase express cell surface receptors for the molecule (in addition to expressing receptors for the rolling mediator and integrin binding partner utilized), thereby activating integrin-mediated arrest. In a preferred aspect, CD62 and ICAM-1 are used as the rolling mediator and integrin binding partner, respectively, to assay for chemoattractants with receptors on neutrophils and/or monocytes.

It should be noted that chemoattractants can be used as either inhibitors or promoters of the inflammatory response depending on how they are administered. For example, a chemoattractant gradient directing leukocytes toward a specific tissue is expected to be pro-inflammatory at such tissue, whereas general systemic administration of a chemoattractant is expected to be inhibitory to leukocyte extravasation, since the systemically administered chemoattractant would competitively inhibit leukocyte recognition of chemoattractant gradients directing its migration toward tissues.

To identify an integrin binding partner, an arrest model apparatus is used, in which the rolling mediators on a solid phase thereof have binding partners situated on the leukocytes present in the flow medium to be passed through the apparatus. One or more chemoattractants are introduced into the flow medium. A chemoattractant is used which has a receptor on the same subset(s) of leukocytes that express the rolling mediator binding partner. A compound or molecule to be tested for integrin binding partner function is affixed onto the surface of the solid phase. After the flow medium is passed through the apparatus, it is determined whether any leukocytes have arrested on the solid phase. Arrest of leukocytes indicates that the molecule is an integrin binding partner which recognizes an integrin present on the same leukocyte subset(s) that express the rolling mediator binding partner and the chemoattractant receptor.

To identify a rolling mediator by use of a rolling model apparatus, the molecule to be tested for rolling mediator activity is incorporated onto the solid phase surface(s) of the rolling model apparatus, and flow medium containing leukocytes is passed through. Rolling of the leukocytes along the solid phase indicates that the molecule has rolling mediator activity and that the leukocytes express a binding partner for the rolling mediator.

To identify a rolling mediator by use of an arrest model apparatus, the molecule to be tested for rolling mediator activity is incorporated onto the solid phase surface(s) of the arrest model apparatus. Also incorporated onto the solid phase surface(s) is an integrin binding partner. A chemoattractant is introduced into the flow medium passing through the apparatus. The flow medium contains leukocytes which express the integrin recognizing the integrin binding partner and express a receptor for the chemoattractant. After passage of the flow medium through the apparatus, it is determined whether any leukocytes have arrested on the solid phase. Arrest of leukocytes indicates that the test molecule has rolling mediator activity and that the leukocytes which express the integrin and the chemoattractant receptor also express a binding partner for the test molecule.

A molecule can also be identified as a functional component in the processes of leukocyte rolling, or rolling and arrest, or as an enhancer thereof, by the methods described supra in which an increase in number or percentage of cells rolling or arrested, is detected relative to the number or percentage of such cells in the absence of the test molecule.

5.11. Therapeutic and Diagnostic Utilities of the Inhibitors and Promoters of the Inflammatory Response The inhibitors and promoters of the invention have use therapeutically in diseases or disorders involving inflammation, and which involve extravasation of leukocytes. The invention provides methods of reducing inflammation, and of treating or preventing disorders associated therewith, by administration to a subject of an effective amount of the inhibitory compounds of the invention. In an alternative embodiment, the invention provides methods of stimulating the inflammatory response, and treating or preventing disorders associated with a deficit in the desired inflammatory response, by administration to a subject of an effective amount of the pro-inflammatory compounds (promoters) of the invention. The subject is preferably an animal, including but not limited to animals such as cows, pigs, chickens, etc., and is preferably a mammal, and most preferably human.

Disease and disorders which can be treated by administration of a therapeutically effective amount of the inhibitory compounds of the invention include but are not limited to the following:

Inflammatory arthritis—e.g., rheumatoid arthritis, seronegative spondeloarthritites (Behcets disease, Reiter's syndrome, etc.), juvenile rheumatoid arthritis, vasculitis, psoriatic arthritis, polydermatomyositis.

Systemic lupus erythematosus (SLE).

Asthma.

Inflammatory dermatoses—e.g., psoriasis, dermatitis herpetiformis, eczema, necrotizing and cutaneous vasculitis, bullous diseases.

Reperfusion injury.

Septic shock (Sepsis).

Adult respiratory distress syndrome (ARDS).

Tissue damage relating to tissue transplantation.

Other autoimmune disorders. In addition to the autoimmune disorders SLE and rheumatoid arthritis, disorders such as glomerulonephritis, juvenile onset diabetes, multiple sclerosis, allergic conditions, autoimmune thyroiditis, allograft rejection (e.g., rejection of transplanted kidney, heart, or liver), Crohn's disease, and graft-versus-host disease can be treated.

Thermal injury (burn). The main complications due to burn are inflammatory in nature, including shock, and pulmonary edema.

Cardiopulmonary bypass. Systemic inflammation has been associated with the use of pump-oxygenator systems in cardiopulmonary bypass and hemodialysis, which can lead to organ dysfunction, termed the post-pump syndrome or post-perfusion syndrome.

In addition, other diseases and clinical correlates of undesirable inflammatory responses can be treated with the inhibitors of the invention, including but not limited to those associated with hemolytic anemia, hemodialysis, blood transfusion, certain hematologic malignancies, pneumonia, post-ischemic myocardial inflammation and necrosis, barotrauma (decompression sickness), ulcerative colitis, inflammatory bowel disease, atherosclerosis, cytokine-induced toxicity, necrotizig enterocolitis, granulocyte-transfusion-associated syndromes, Reynaud's syndrome, multiple organ injury syndromes secondary to septicemia or trauma, and acute purulent meningitis or other central nervous system inflammatory disorders. In addition, the inhibitors of the inflammatory response which bind to ICAM-1 can be used to treat or prevent viral infections such as rhinoviral infection, since the rhinovirus binds to ICAM-1 on human cells and thereby initiates infection of the cells.

Diseases or disorders that can be treated by the pro-inflammatory compounds of the invention include but are not limited to immunosuppression (e.g., due to AIDS, cancer chemotherapy, radiation therapy, corticosteroid therapy, or other therapy for autoimmune disease), and congenital immunodeficiencies.

5.11.1. Demonstration of Therapeutic Utility

Compounds demonstrated to have the desired activity in the apparatuses of the invention can then be tested in vivo for the desired anti- or pro-inflammatory activity, as the case may be. For example, such compounds can be tested in suitable animal model systems prior to testing in humans, including but not limited to rats, mice, chicken, cows, monkeys, rabbits, etc. Suitable model systems are also used to demonstrate therapeutic utility (see infra).

For in vivo testing, prior to administration to humans, any animal model system known in the art may be used. For example, several animal models are available to demonstrate the efficacy of anti-inflammatory compounds of the invention in the treatment of adult respiratory distress syndrome (ARDS). These include New Zealand white rabbits infused with activated complement (Nuytinck et al., 1986, Brit. J. Exp. Pathol. 67: 537–548); cerulean-induced acute pancreatitis in rats (Guice et al., 1988, Ann. Surg. 208: 71–77); a porcine model produced by infusion of live Pseudomonas aeruginosa (Dehring et al., 1987, J. Trauma 27: 615–625); cynomolgus monkeys (Macaca fascicularis) made acutely septic with infusions of *E. coli*, resulting in severe sepsis and ARDS (Stevens et al., 1986, J. Clin. Invest. 77:1812–1816).

Two animal models of sepsis which can be used are a rat cecal ligation and puncture model (von Allmen et al., 1990, J. Surg. Res. 48: 476–480) and a sheep common bile duct contamination model (Barke et al., 1990, Arch. Surg. 125: 437–440).

A rabbit model of barotrauma is known (Ward et al., 1990, Undersea Biomed. Res. 17: 51–66).

For animal models of thermal injury, see Bjornson et al., 1986, J. Infect. Dis. 153: 1098–1107; Oldham et al., 1988, Surgery 104: 272–279; Friedl et al., 1989, Am. J. Pathol. 135: 203–217; Demling et al., 1989, Surgery 106: 52–59.

An animal model system for rheumatoid arthritis is that consisting of animals of the autoimmune MRL/1 mouse strain (Murphy, E. D. and Roths, J. B., 1978, in *Genetic Control of Autoimmune Disease*, Rose, N. R., et al., eds., Elsevier/North-Holland, N.Y., pp. 207–219), that develop a spontaneous rheumatoid arthritis-like disease (Hang et al., 1982, J. Exp. Med. 155: 1690–1701).

5.11.2. Therapeutic Administration and Compositions

Various delivery systems are known and can be used to administer the compounds of the invention, e.g., encapsulation in liposomes, microparticles, microcapsules, expression by recombinant cells, etc. Other methods of introduction include but are not limited to intradermal, intramuscular, intraperitoneal, intravenous, subcutaneous, intranasal, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local, e.g., direct injection at the inflamed joint of someone suffering from rheumatoid arthritis.

The present invention also provides pharmaceutical compositions. Such compositions comprise a therapeutically effective amount of a compound of the invention, and a pharmaceutically acceptable carrier or excipient. Such a carrier includes but is not limited to saline, buffered saline, dextrose, water, glycerol, ethanol, and combinations thereof. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment of a particular disorder or condition will depend on the nature of the disorder or condition, and can be determined by standard clinical techniques. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

6. LEUKOCYTES ROLL ON A SELECTIN AT PHYSIOLOGIC FLOW RATES: DISTINCTION FROM AND PREREQUISITE FOR ADHESION THROUGH INTEGRINS

We show herein that rolling of leukocytes on vascular endothelial cells, an early event in inflammation, can be reproduced in vitro on artificial lipid bilayers containing purified CD62, a selectin also named PADGEM and GMP-140 that is inducible on endothelial cells. Neutrophils rolled on this selectin under flow conditions similar to those found in postcapillary venules. Adhesion of resting or activated neutrophils through the integrins LFA-1 and Mac-1 to ICAM-1 in a lipid bilayer did not occur at physiologic shear stresses; however, static incubation of activated neutrophils allowed development of adhesion that is greater than 100-fold more shear resistant than found on CD62. Addition of a chemoattractant to activate LFA-1 and Mac-1 resulted in the arrest of neutrophils rolling on bilayers containing both CD62 and ICAM-1. Thus, at physiologic shear stress, rolling on a selectin is a prerequisite for activation-induced adhesion strengthening through integrins.

6.1. Results

6.1.1. Reconstitution of CD62 and ICAM-1 in Lipid Bilayers

Immunoaffinity-purified CD62 and ICAM-1 in octyl-β-D-glucopyranoside (OG), alone or together, were mixed with phosphatidylcholine, and liposomes were prepared by dialysis. Liposome suspensions were placed on clean glass slides to form planar lipid bilayers with incorporated proteins (Watts et al., 1986, Nature 320: 179–181). The incorporation of both CD62 and ICAM-1 into the membranes was quantitated by saturation binding with $^{125}$I-mAb. Throughout the experiments described below, neutrophil binding to planar bilayers containing CD62 and ICAM-1 was found to be highly specific. Neutrophils did not bind to planar membranes containing phosphatidylcholine alone. Neutrophil binding to planar membranes containing CD62 was 98% reversible by incubation with EDTA for 10 min. Binding of N-formyl methionyl leucyl phenylalanine (fMLP)-stimulated neutrophils to planar membranes containing ICAM-1 was inhibited 97% by a combination of anti-LFA-1 (TS1/22) and anti-Mac-1 (LPM19c) α subunit antibodies, in agreement with previous reports (Smith et al., 1989, J. Clin. Invest. 83: 2008–2017; Diamond et al., 1990, J. Cell Biol. 111: 3129–3139). TS1/22 or LPM19c alone did not inhibit fMLP-stimulated neutrophil binding to ICAM-1; thus, the results reported below reflect interaction of both LFA-1 and Mac-1 on the neutrophil with ICAM-1 in the planar membrane.

6.1.2. The Selectin CD62 is Distinctive in Support of Adhesion at Venular Levels of Shear Stress To measure attachment of neutrophils under flow conditions, glass slides containing planar bilayers were incorporated into a parallel plate flow chamber (FIG. 3). Neutrophils ($10^6$/ml) were infused at flow rates that were regulated to produce wall shear stresses bracketing the range estimated to exist in post-capillary venules. Wall shear rates and stresses in the flow chamber are calculated from chamber geometry and volumetric flow rate (Lawrence et al., 1990, Blood 75: 227–237). Shear stresses in vivo can be calculated from centerline velocity and vessel diameter using the Hagen-Poiseuille equation. In both cylindrical and parallel plate geometries, the velocity profile of a Newtonian fluid is parabolic (FIG. 4). The change in velocity per change in radial displacement is called shear and is highest at the wall. Shear stress, the product of shear and viscosity, better correlates with the forces acting on a cell under flow. Shear stresses of 1–10 dyn/cm$^2$ have been measured for postcapillary venules (Heisig, 1968, Adv. Microcirc. 1: 89–94), and in the classic studies of Atherton and Born (1972, J. Physiol. 222: 447–474), leukocytic rolling was observed at shear stresses that we calculate to be 1.5–4.0 dyn/cm$^2$.

Figure 5A:
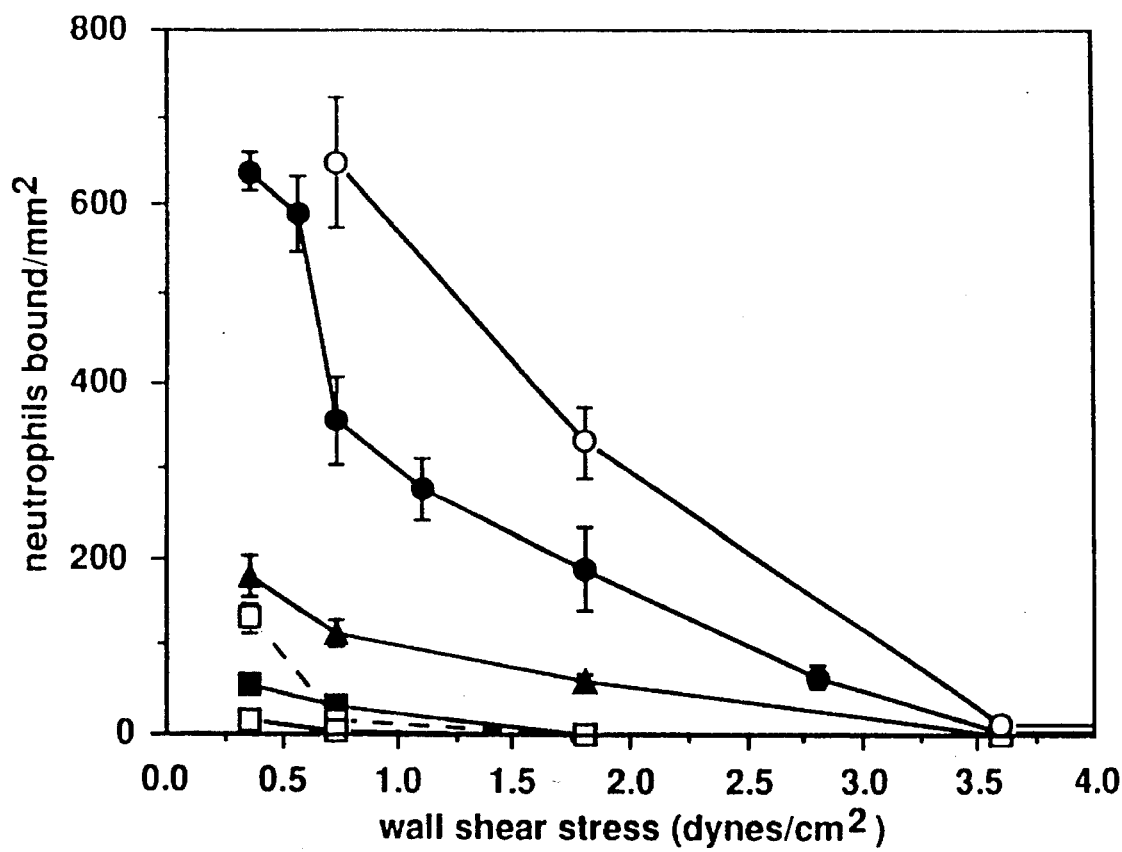

Flowing neutrophils readily bound to artificial bilayers containing CD62 at wall shear stresses within the physiologic range (FIG. 5A). Attachment was dependent on the density of CD62, with efficient attachment at 1.8 to 2.8 dyn/cm$^2$ at 400 and 200 sites per μm$^2$, and significant attachment occurring at 1.8 dyn/cm$^2$ at a density of 50 sites per μm$^2$. By contrast, neutrophils did not adhere to artificial bilayers containing ICAM-1 under flow conditions, even at high ICAM-1 densities of 1,000 sites per μm$^2$ (FIG. 5A). Lower ICAM-1 densities than this support strong static binding of activated neutrophils (see below); however, neutrophils that were stimulated with PMA did not bind at physiologic shear stresses (>1 dyn/cm$^2$), and bound only at low levels in stagnant flow at a shear stress of 0.36 dyn/cm$^2$ (FIG. 5A). Flowing lymphocytes that have been activated by cross-linking the T cell antigen receptor with mAb also fail to bind to ICAM-1 under flow conditions (not shown) but bind avidly through LFA-1 to ICAM-1 under static conditions (Dustin and Springer, 1989, Nature 341: 619–624). Lymphocytes also fail to bind through CD2 to LFA-3 (1,000 sites per μm$^2$) under flow conditions (not shown), but do so at stasis (Chan et al., 1991, J. Cell Biol. 115: 245–255). The failure of several integrin-Ig superfamily interactions and Ig-Ig superfamily (CD2-LFA-3) interactions to occur under flow conditions is distinct from the efficiency of interaction through the selectin CD62.

Figure 5B:
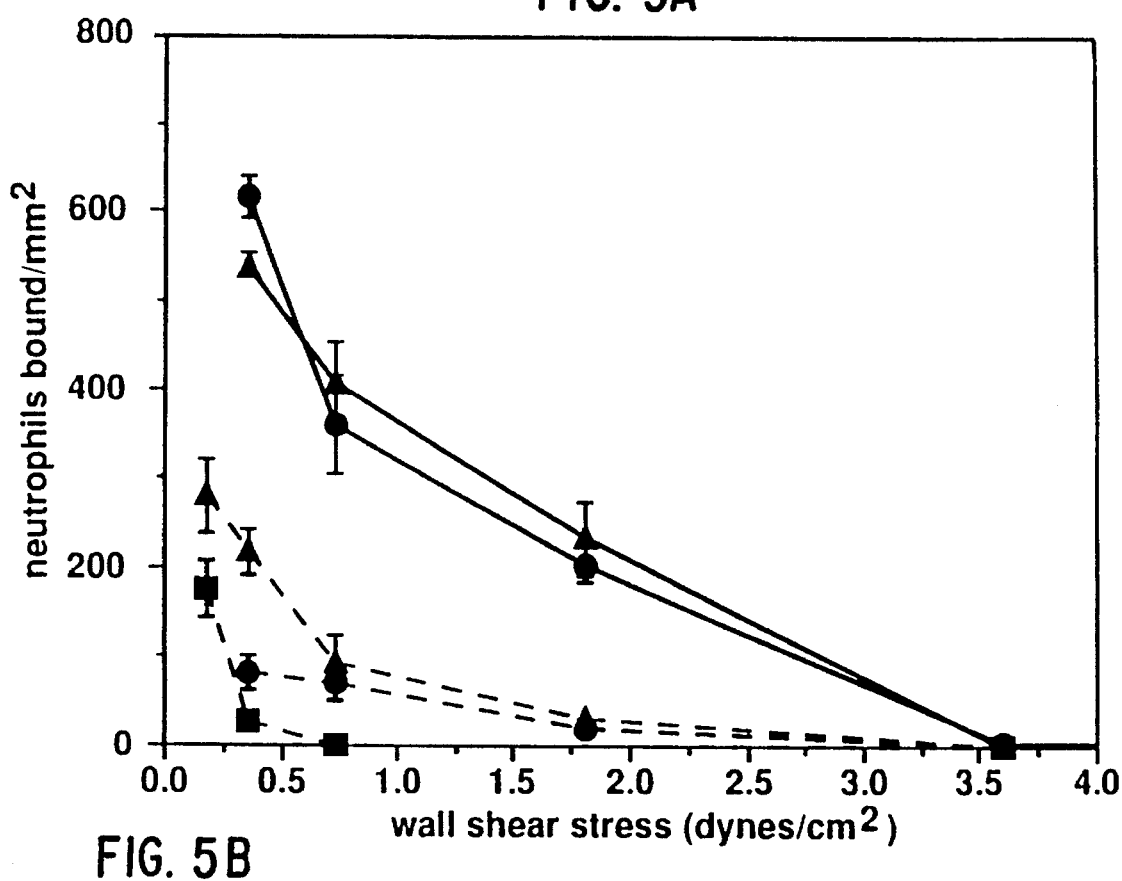

The efficiency of adhesion of unactivated neutrophils to artificial bilayers containing a mixture of CD62 and ICAM-1 was indistinguishable from adhesion to CD62 alone (FIG. 5B). Thus, no cooperative interactions between these adhesion mechanisms occur on resting neutrophils.

Activation with PMA prior to infusion greatly decreased the efficiency of adhesion to CD62 (FIG. 5B). The amount of adhesion of PMA-stimulated neutrophils to the mixture of CD62 and ICAM-1 (FIG. 5B) was additive for the adhesion to CD62 alone (FIG. 5B) and ICAM-1 alone (FIG. 5B).

6.1.3. Neutrophils Roll on CD62

Figure 6A:
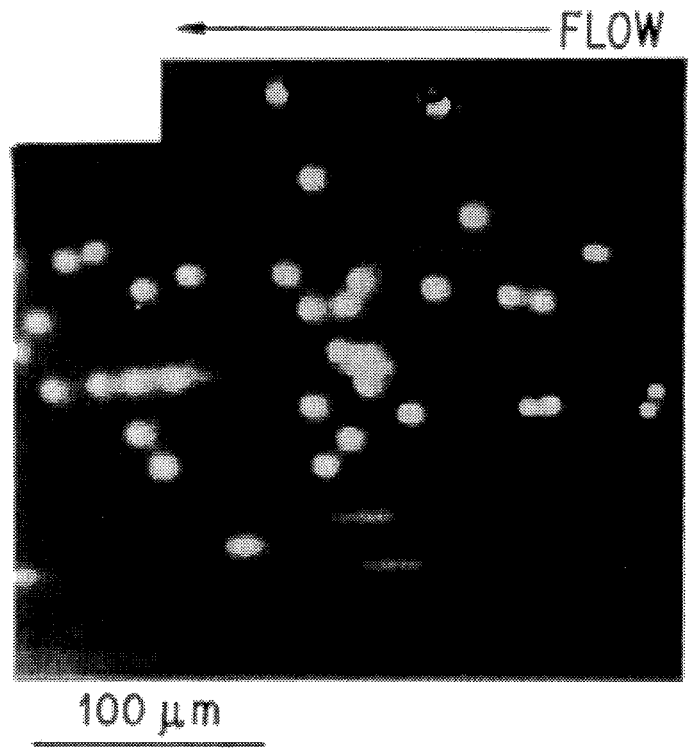
Figure 6B:
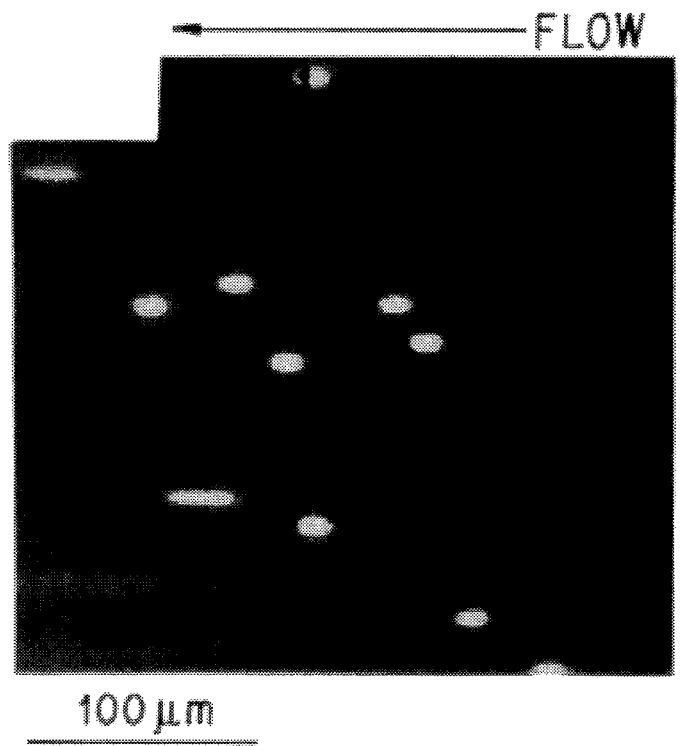

Artificial bilayers containing CD62 were remarkable not only for their ability to support adhesion under physiologic flow conditions, but also in the rolling mode of this adhesion. Neutrophils rolled on the CD62 substrate, driven by fluid drag forces, as readily recorded using a video camera (FIG. 6). Rolling neutrophils that accumulated on the CD62 substrate remained round and appeared as sharp images, whereas nonadherent cells that tumbled past in the shear flow were blurred streaks (FIG. 6A). Only nonadherent, tumbling cells were visualized on ICAM-1 substrates (FIG. 6B); the length of the blur is dependent on the distance from the wall because of the velocity profile (FIG. 4), with the slowest tumbling cells closest to the substrate.

Confirming that the cells roll rather than slide on the CD62 substrates, rotation of the polymorphic nucleus of the neutrophil was observed using a 40× objective and was clearly visible when videotapes were played back; the progress of rolling cells across a substrate at 2 s intervals is shown using a 40×objective in FIGS. 6C–6F. At lower shear stresses cells frequently wobbled as they rolled. Individual cells rolled with a relatively, but not completely, uniform velocity. Rolling was sometimes interrupted by brief pauses where the cells appeared to momentarily halt on the substrate, and also by brief increases in velocity during which the cells appeared to detach from the substrate and then reattach several cell diameters downstream. Rolling cells were in equilibrium with nonadherent cells, as reflected by detachment of some rolling cells with their loss from the field of view and attachment of other cells.

Figure 6C:
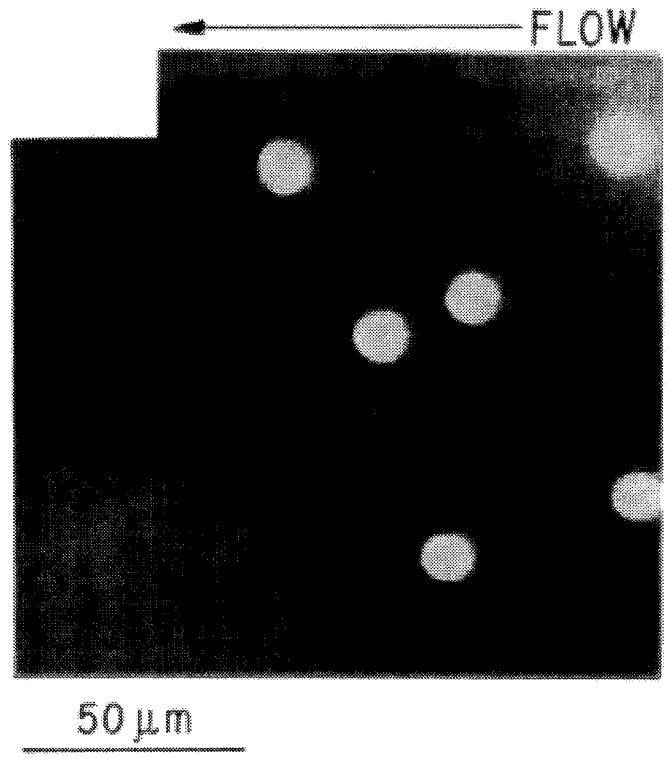
Figure 6D:
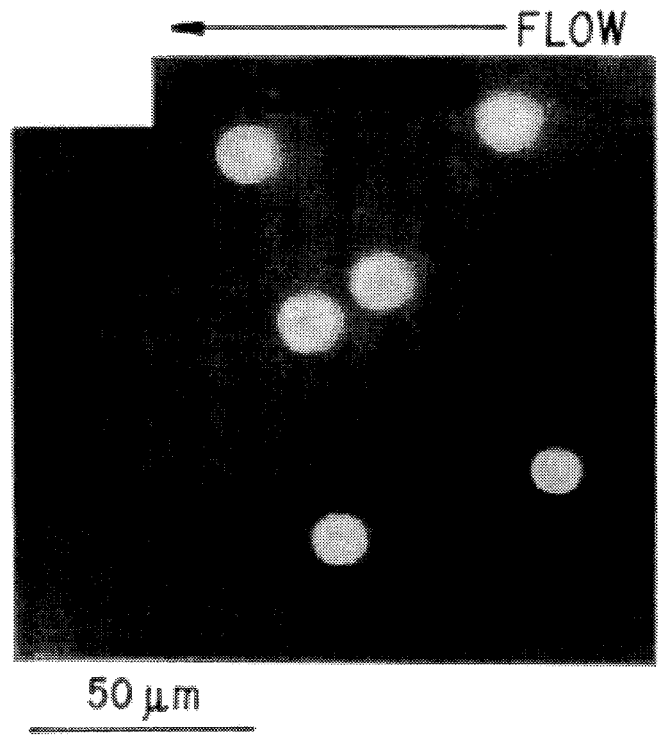
Figure 6E:
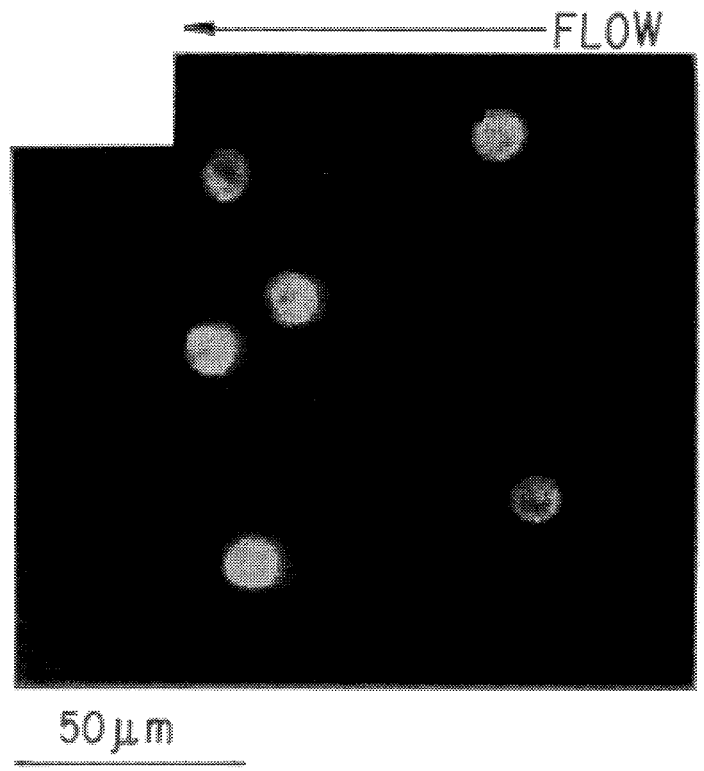
Figure 6F:
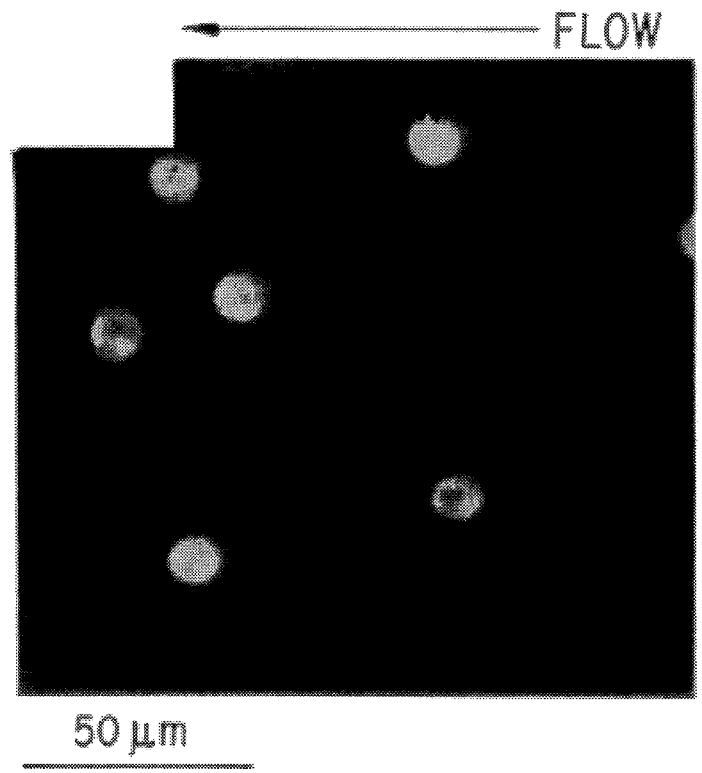

The overall similarity in rolling velocity among different cells led to the appearance that they rolled as a group over the substrate, as for the six cells in FIGS. 6C–6F, but there was some variation in velocity; comparison of FIGS. 6C and 6F shows that the cell in the upper left in FIG. 6C is the slowest of the group and the one 5 o'clock to it in FIG. 6C is the fastest and has overtaken it by FIG. 6F.

Disturbance of the laminar flow profile by attached cells was evident from observation of cells attaching to artificial bilayers of CD62 at a shear stress of 1.8 dyn/cm$^2$ and above. Single cells bound in a random distribution over the substrate. However, once one cell bound, binding of further cells immediately downstream was much more likely than in areas of the substrate with no attached cells. It appeared that the neutrophils were following locally disturbed streamlines that increased the chance of collision with and subsequent attachment to the substrate. After several minutes, the cells became more evenly distributed. At shear stress levels of 0.73 dyn/cm$^2$ and below, attachments were uniformly distributed even at the earliest times.

Rolling velocity increased with increasing shear force (FIG. 7). The rolling velocity was proportional to the shear force at low shear stresses, and then began to plateau. This may reflect the effect of torque acting on a rolling but deformable object, leading to a greater contact area and less fluid drag. Rolling velocity was dependent on the site density of CD62 (FIG. 7). The higher the CD62 density, the more slowly the neutrophils rolled at a given shear stress. This is as predicted, because a higher number of receptor-ligand interactions will lead to a greater resistance to the fluid drag force. The slower rolling velocities at higher site density correlated with the increased effectiveness of attachment. Inclusion of ICAM-1 in artificial bilayers containing CD62 did not alter rolling velocity (FIG. 7), correlating with its lack of effect on attachment.

Rolling did not appear to result in any alteration in the cells or the substrate. The rolling velocity of groups of cells followed along the substrate did not appear to change with time. The rolling velocity of cells on CD62 substrates was unaltered for at least 15 min at a single observation condition, and the same substrate could be used for observations at many different shear stresses, without any alteration in rolling velocity measurements for the same shear stress replicated at the beginning and end of the set of observations. When the direction of flow was reversed, the direction of rolling was reversed and the cells rolled back "over their tracks" with the same velocity as in the forward direction.

We compared the velocities of unstimulated neutrophils rolling over a CD62 substrate and tumbling over an ICAM-1 substrate to the predicted velocity for a sphere of the same diameter, 7 μm (Table 4). t,810
The measurements on the ICAM-1 substrate are for the cells flowing closest to the substrate, as determined by the focal plane. The unstimulated neutrophils flowing over the ICAM-1 substrate moved at a velocity 100-fold greater than the cells rolling on the CD62 substrate. Because of the torque exerted by shear flow, a spherical object will rotate at an angular velocity of one-half the shear rate, so its motion, particularly if close to the wall, is not qualitatively different from rolling along a flat surface. Predicted velocities of a sphere 7 μm in diameter having no interaction with a smooth wall (Goldman et al., 1967, Chem. Engineer Sci. 22: 653–660) at distances of 1, 10 and 500 nm are more than an order of magnitude higher than the measured velocities for rolling on CD62 (Table 4). The rolling velocities observed on CD62 thus require an adhesive interaction. By contrast, the measured velocities on the ICAM-1 substrates are in excellent agreement with the predictions for a sphere tumbling in shear flow, particularly with a separation of 500 nm. Distances on the order of 1 and 10 nm are probably difficult to obtain without contact, since surface features such as ICAM-1 are on the order of this size; ICAM-1 is 18 nm long as measured in the electron microscope (Staunton et al., 1990, Cell 61: 243–254).

6.1.4. Adhesion Under Static Conditions

Figure 8A:
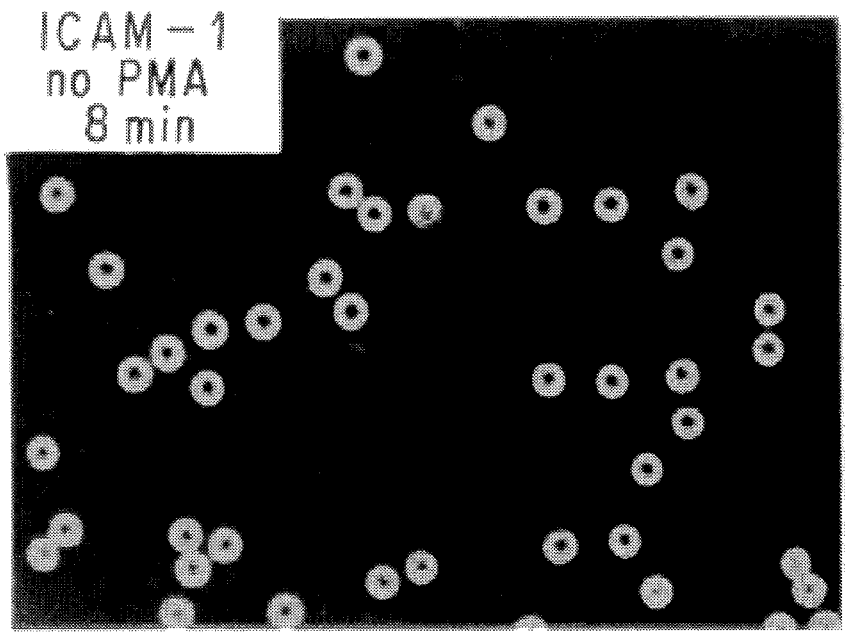
Figure 8B:
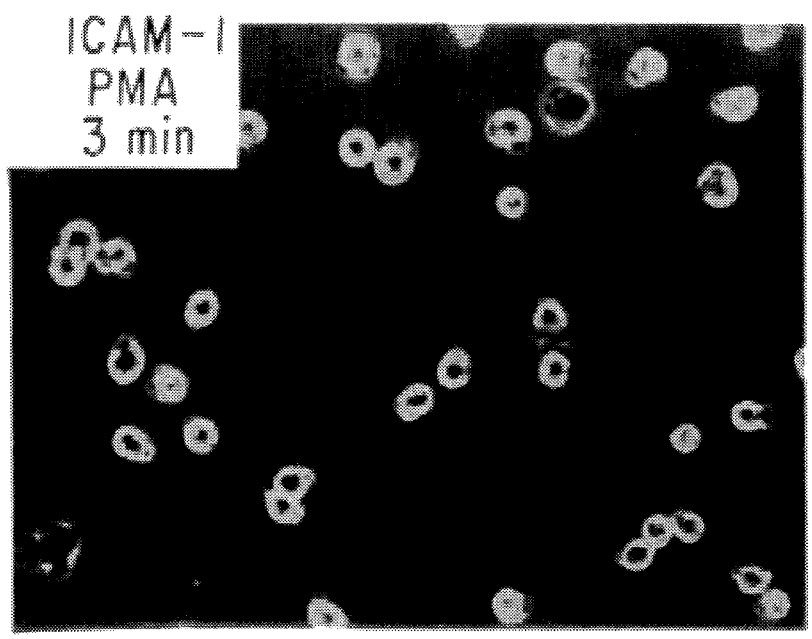
Figure 8C:
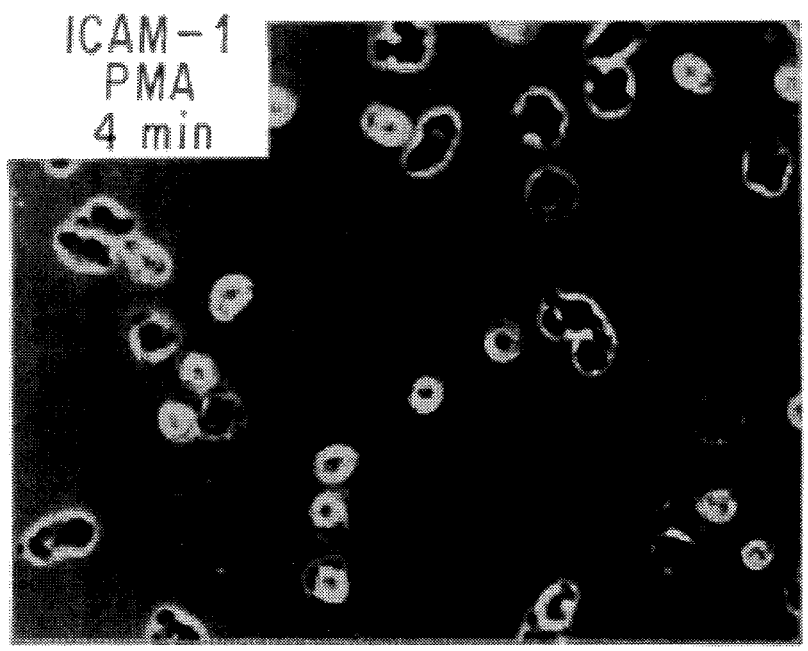
Figure 8D:
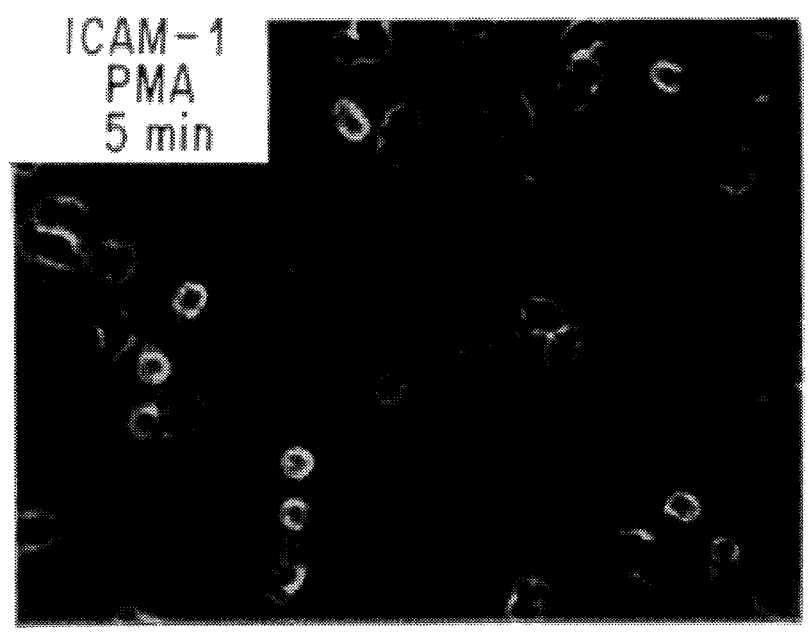
Figure 8E:
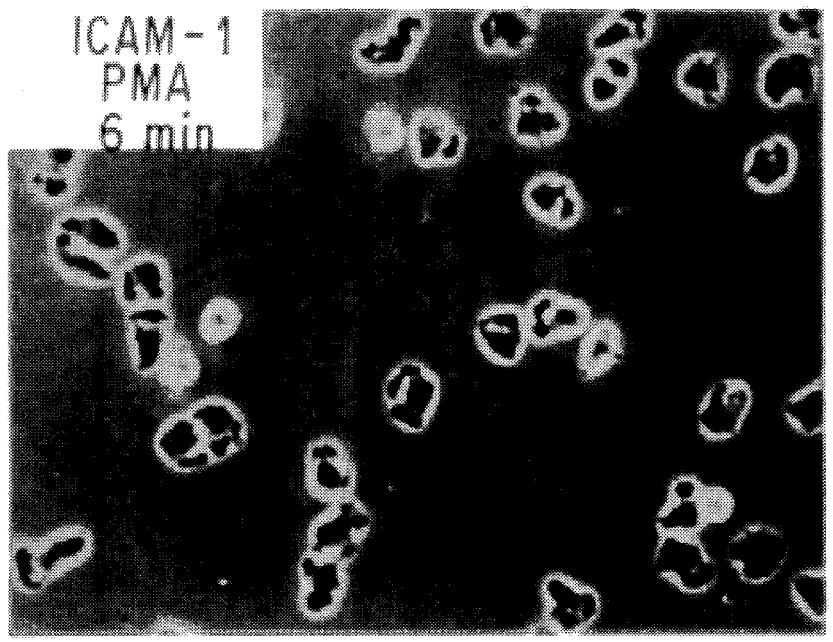
Figure 8F:
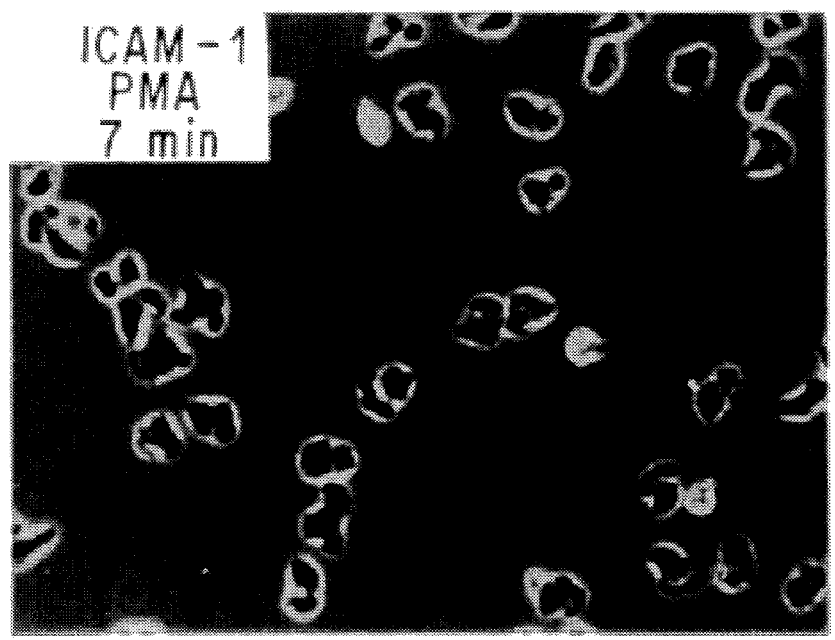
Figure 8G:
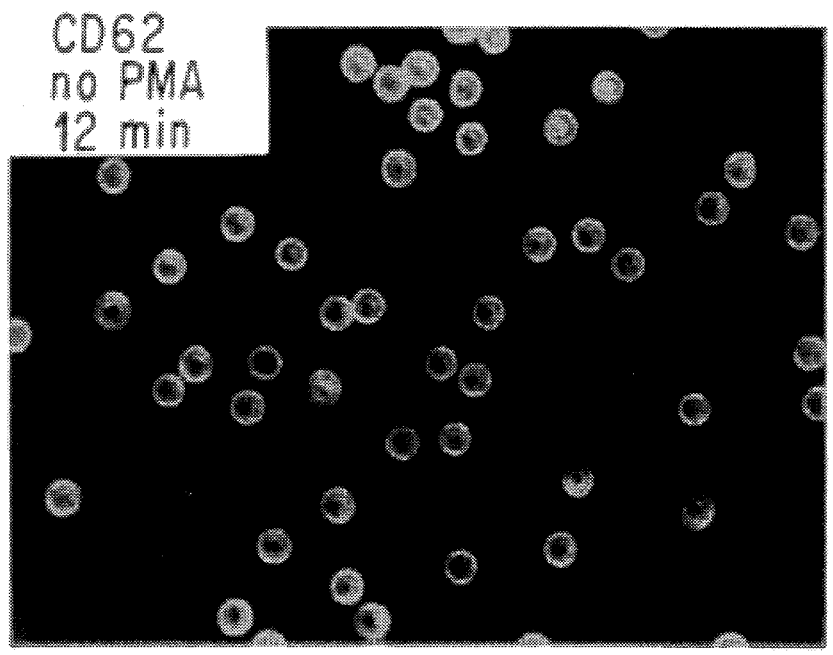

The ability of neutrophils to spread and develop adhesiveness on artificial bilayers under static conditions was examined for comparison to behavior under flow conditions. Neutrophils were injected through a port and examined at different time points; 2 min of the total time was required before all the neutrophils had settled onto the bilayer. Resting neutrophils remained round on ICAM-1 bilayers, with no spreading after prolonged incubation (FIG. 8A). However, treatment with phorbol 12-myristate-13-acetate (PMA) or fMLP resulted in spreading of almost all neutrophils on ICAM-1 bilayers (FIGS. 8B–8F).

Figure 8H:
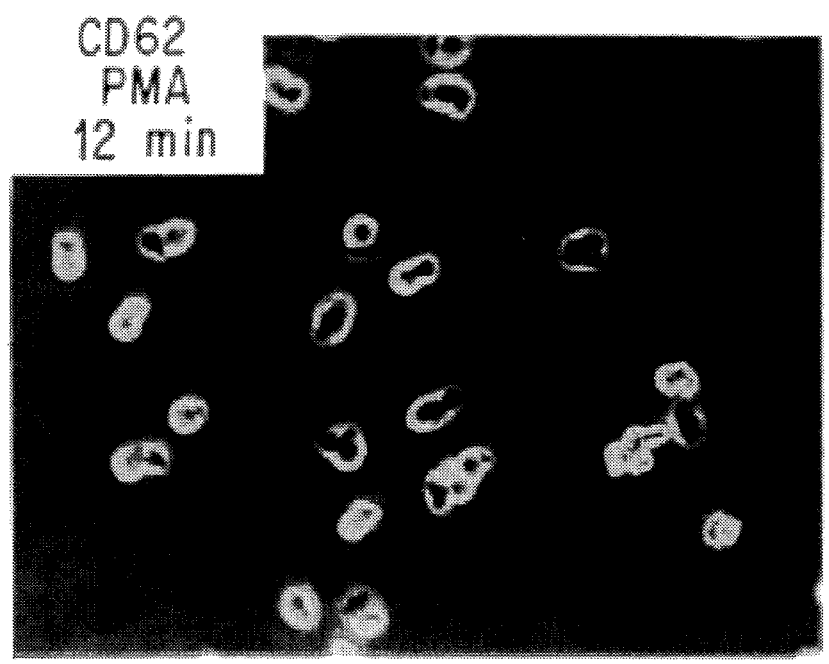

Neutrophils on CD62 bilayers remained round even after prolonged contact of up to 12 min (FIG. 8G), in agreement with observations on rolling cells under flow conditions. Neutrophil activation with PMA induces a bipolar shape change even when cells are held in suspension; PMA-stimulated neutrophils had a bipolar appearance on CD62 bilayers but no spreading was observed (FIG. 8H).

To examine adherence under static conditions, neutrophils were allowed to settle onto the planar membrane, and after 6 min of contact, controlled flow was used to create a detachment force. Binding to CD62 and ICAM-1 was compared, with and without PMA present. This assay highlighted significant differences in patterns of adhesion strengthening between the CD18 and the CD62 pathways.

Figure 9A:
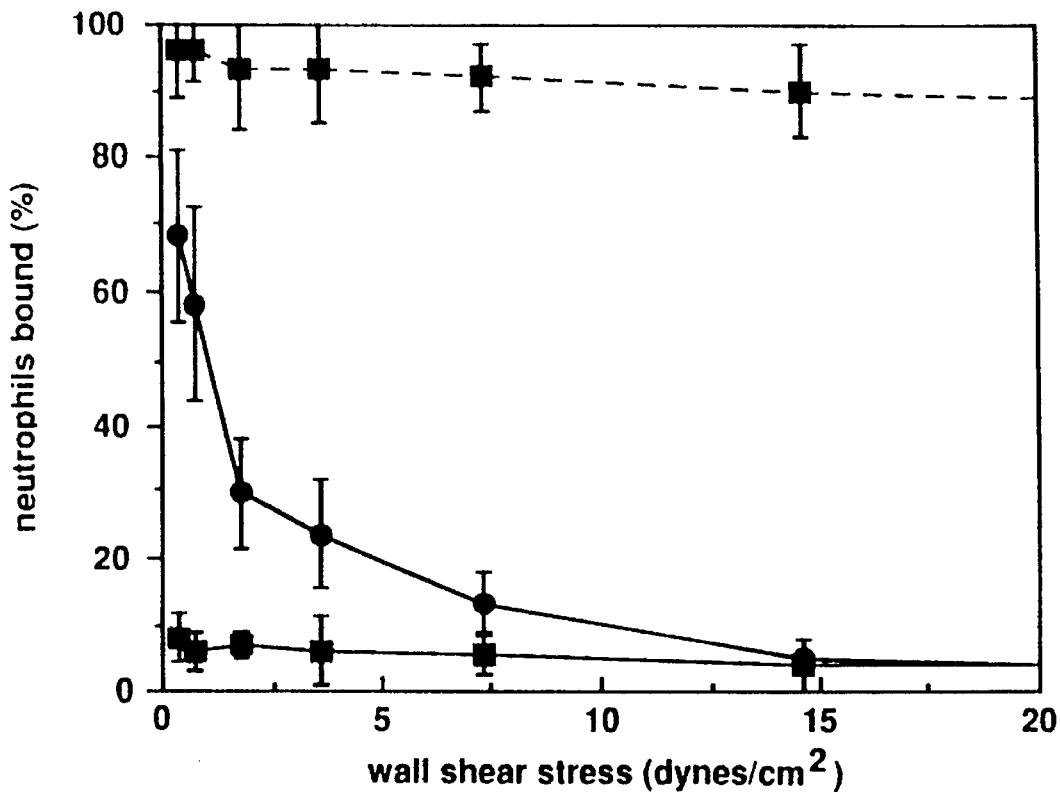

Unstimulated neutrophils did not adhere to artificial bilayers containing ICAM-1 (FIG. 9A). By contrast, PMA-stimulated neutrophils developed strong adhesion to the bilayer during the 6 min contact period. These attachments were dramatically resistant to shear stress; almost all the cells remained attached at wall shear stresses as high as 36 dyn/cm$^2$. The same results were observed after stimulation with 10$^{-7}$M fMLP. These strongly adherent cells could not be induced to roll even at high shear stresses (Table 4). In the same assay, we found that binding was 97% inhibited by a combination of mAbs to the Mac-1 and LFA-1 α subunits, but not by either mAb alone. Thus, adhesion strengthening occurs through both Mac-1 and LFA-1. The differing abilities of ICAM-1 to mediate adhesion of PMA-stimulated neutrophils under flow as compared to static conditions were seen despite use of ICAM-1 at 1,000 sites per μm$^2$ in flow assays and at 250 sites per μm$^2$ in static assays.

The formation of mechanically strong attachments through integrins following PMA or fMLP stimulation contrasted with the pattern observed for CD62. With the same contact time, neutrophils formed very reversible adhesions to CD62 (FIG. 9A). The shear stresses required for detachment of neutrophils from CD62 were roughly comparable to the maximal shear stresses at which attachments could form (FIG. 6, above). More importantly, all the neutrophils rolled along the planar membrane containing CD62, and at the same velocity as observed for neutrophils that adhered under flow conditions (data not shown). Thus, contact time did not result in adherence strengthening through the selectin CD62.

Figure 9B:
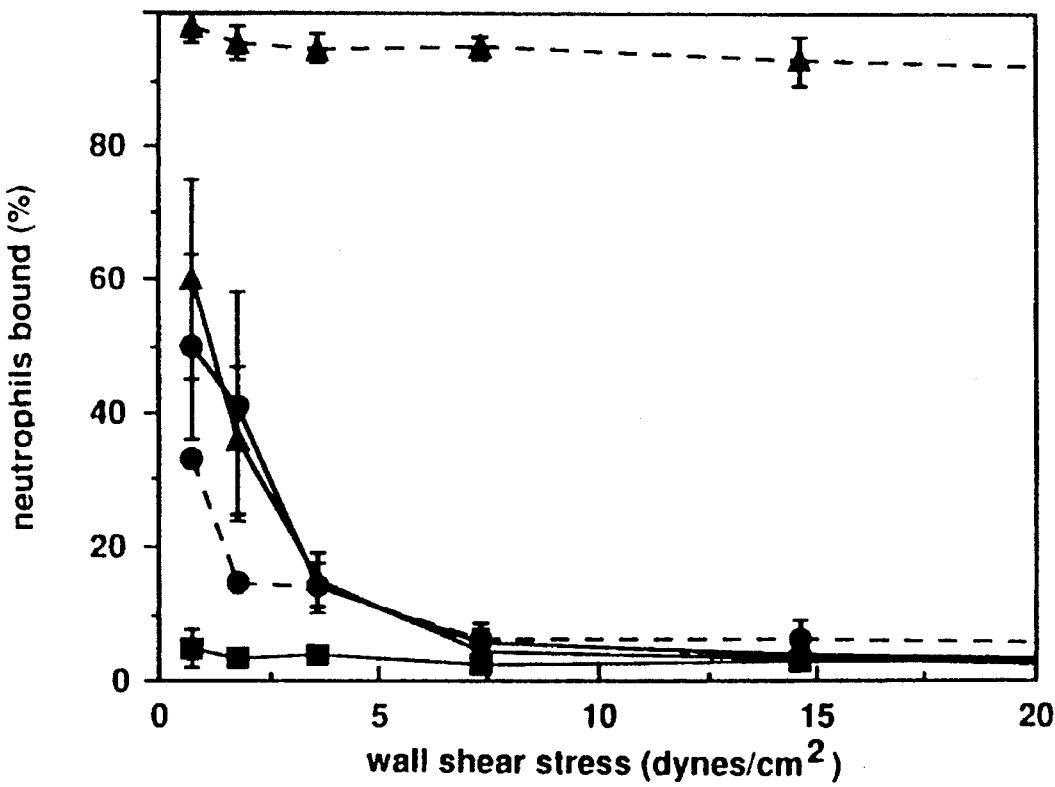

We used bilayers containing both CD62 and ICAM-1 to test for cooperativity in the static binding assay between the selectin and integrin/Ig gene family adhesion systems. No enhancement of resting neutrophil binding was observed on a bilayer containing both CD62 and ICAM-1 compared with CD62 alone (FIG. 9B). The shear sensitivity of binding to both types of planar membranes was equivalent, and rolling occurred as on the CD62 membrane alone. Thus, even under conditions where contact with CD62 and ICAM-1 was maximized, CD62 did not stimulate adhesiveness of neutrophils for ICAM-1. The integrin/Ig and selectin pathways appear to function independently of each other; binding to the ligand for CD62 on neutrophils did not generate a signal that activated integrin avidity.

PMA activation of neutrophils resulted in strong attachments after 6 min of contact with the planar membranes containing both ICAM-1 and CD62 (FIG. 9B). Adherent cells had a morphology indistinguishable from that of PMA-activated neutrophils binding to ICAM-1 alone, and were equally shear resistant. On CD62 alone, PMA did not stimulate development of shear-resistant attachments, but decreased shear resistance relative to unstimulated cells.

6.1.5. Cooperation Between Selectin and Integrin Adhesion Mechanisms

Figure 10A:
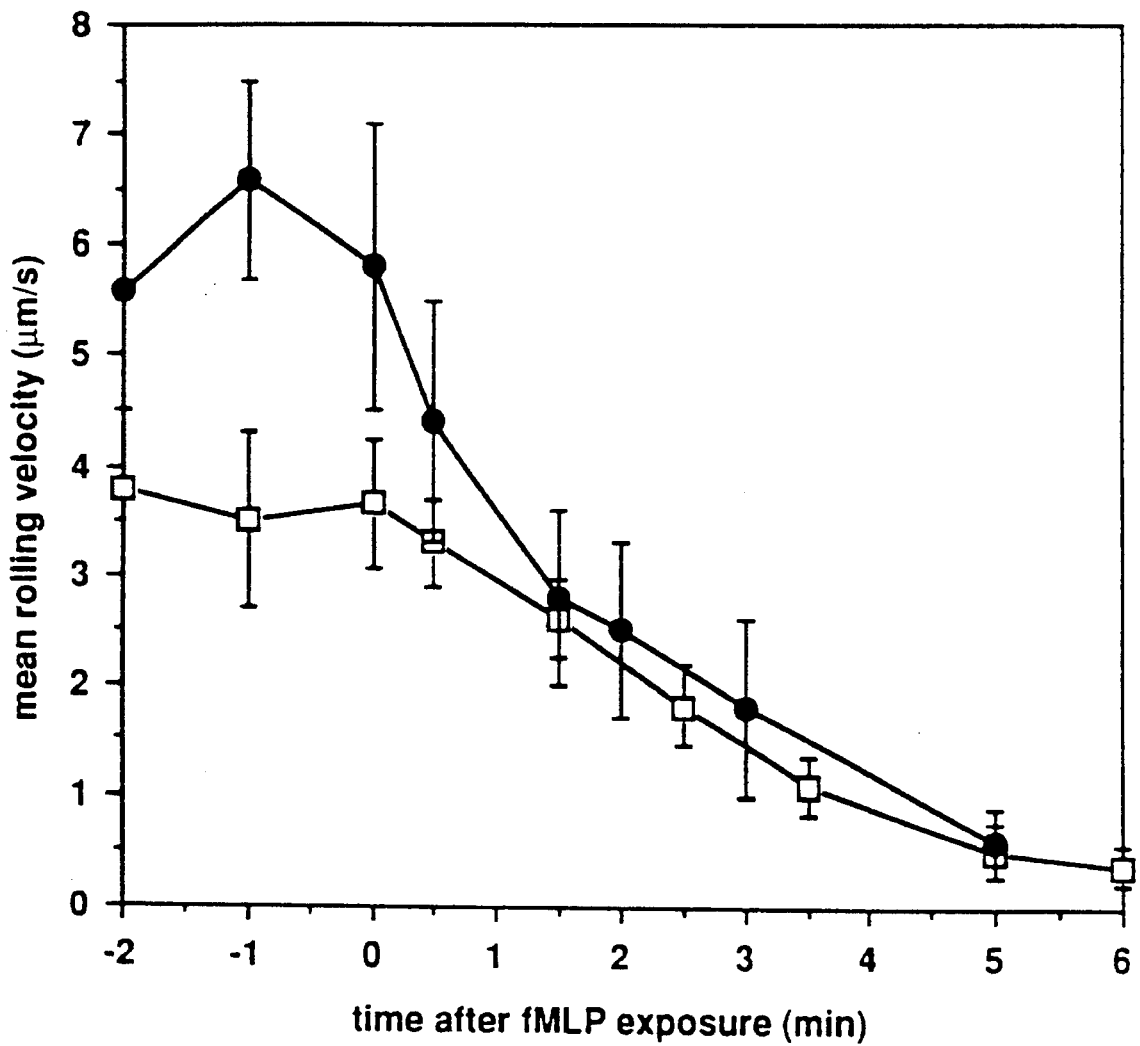
Figure 10B:
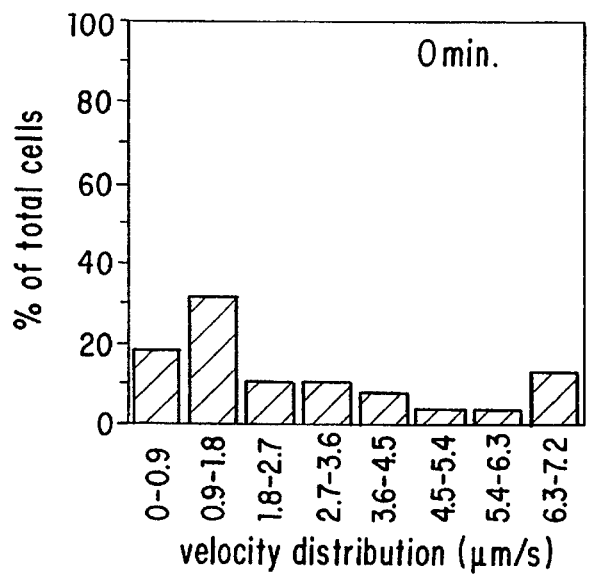
Figure 10B:
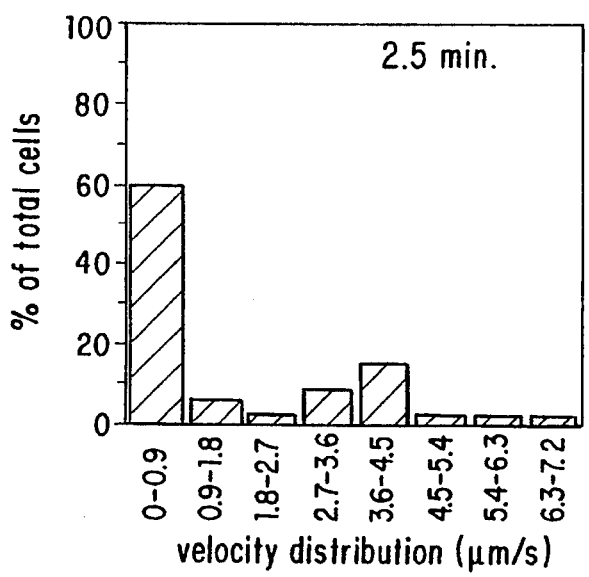
Figure 10B:
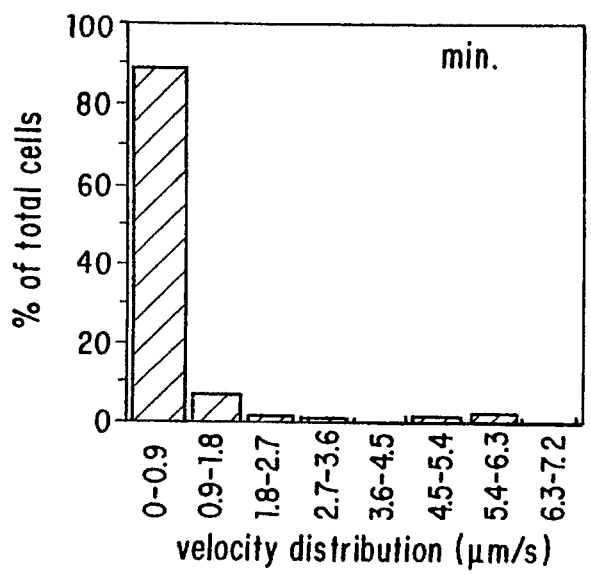
Figure 10C:
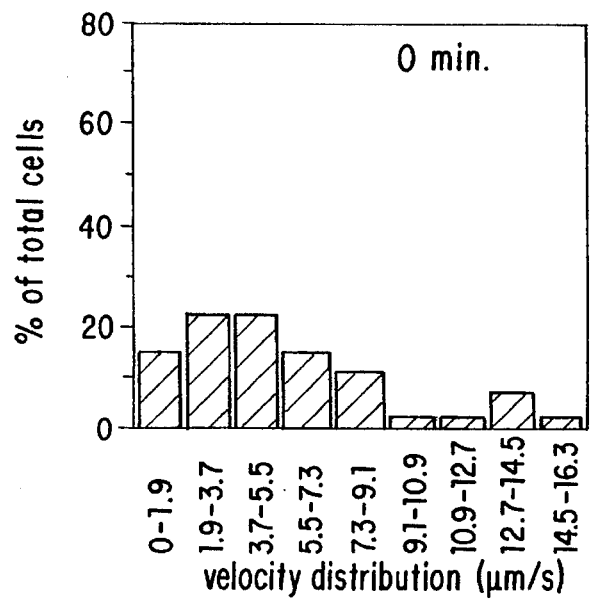
Figure 10C:
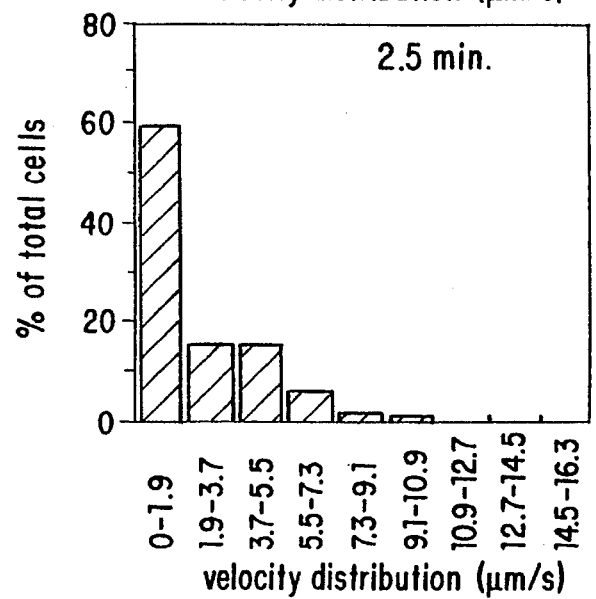
Figure 10C:
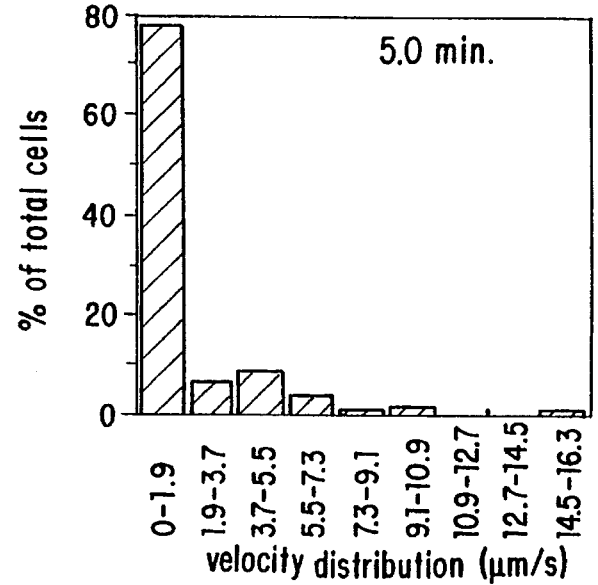
Figure 10D:
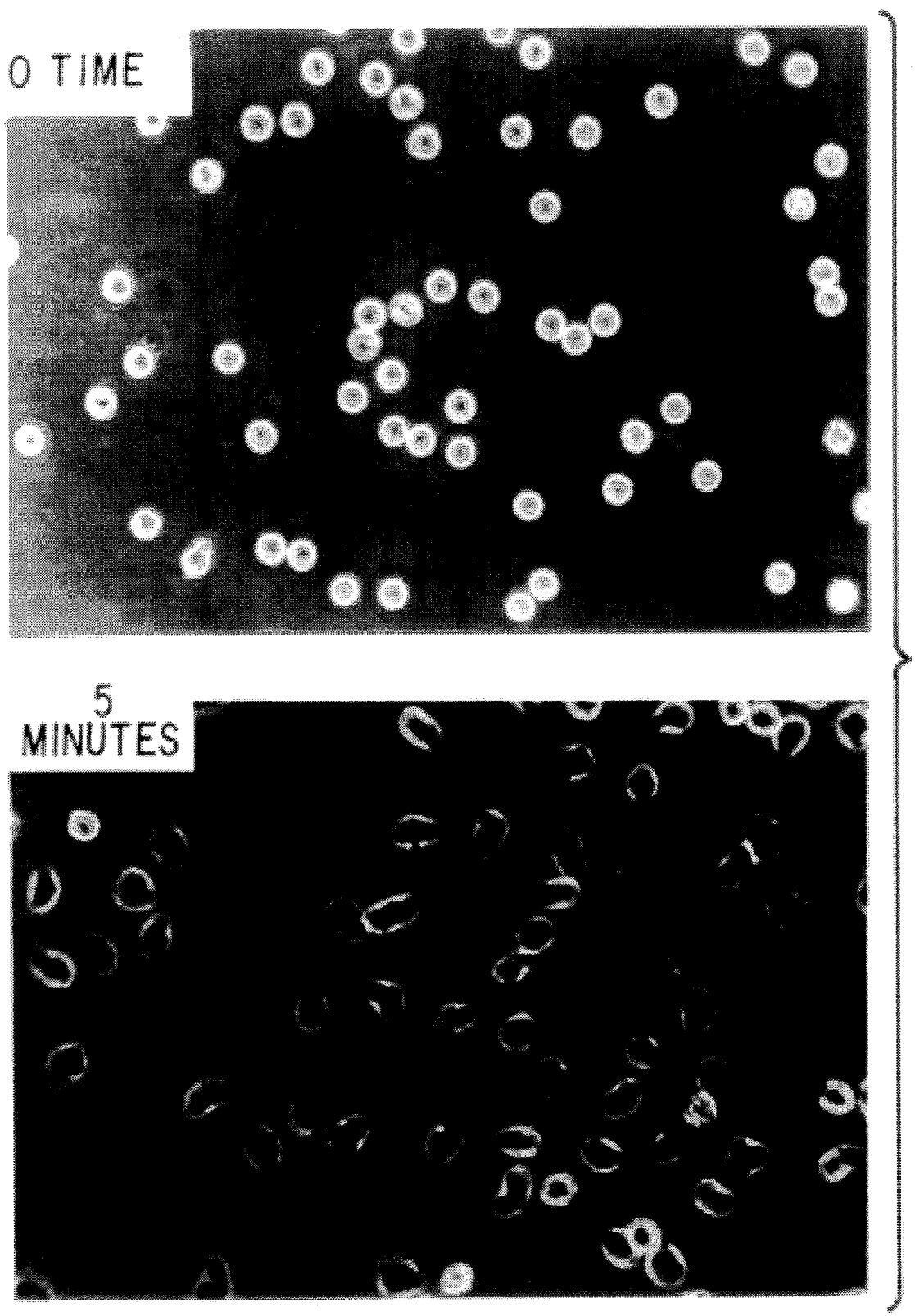
Figure 10E:
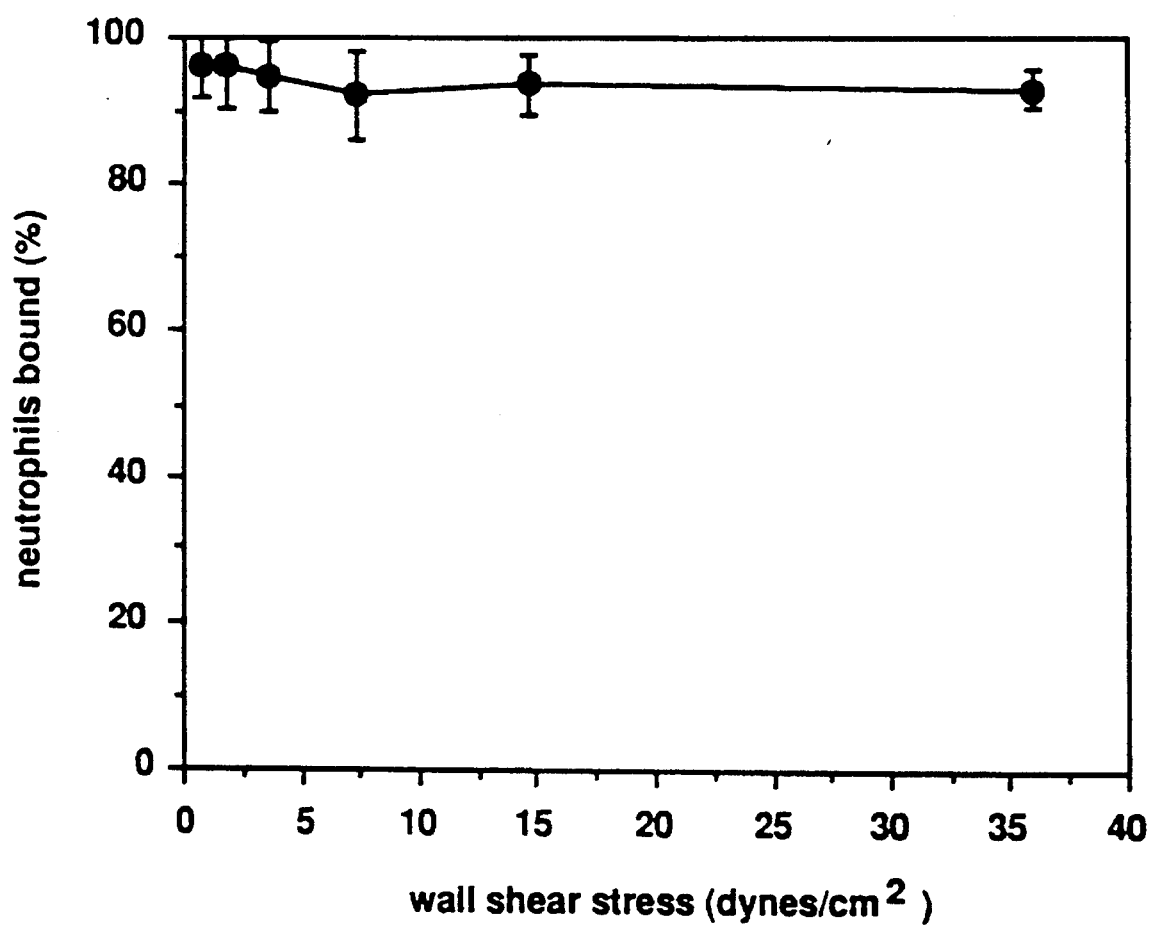

We tested for cooperation between the CD62 rolling and leukocyte integrin adhesion-strengthening mechanisms under conditions that would approximate those at an inflammatory site by addition of fMLP to rolling neutrophils. Neutrophils were infused at two shear stresses in the physiologic range into a flow chamber with an artificial bilayer containing both CD62 and ICAM-1. After a 3 min equilibration period to allow accumulation of rolling neutrophils on the bilayer, 10$^{-9}$M fMLP was added to the infusion medium and reached the rolling neutrophils 12 or 30 s later (0 time, FIG. 10A). Within 30 seconds of exposure, mean rolling velocities had begun to drop at both flow rates (FIG. 10A) and continued to drop for 5 min. After 5 min, essentially all the neutrophils became arrested on the bilayer, as seen both from the average rolling velocity (FIG. 10A) and the velocity distributions (FIGS. 10B and 10C). Arrest of round cells preceded spreading. The round, rolling neutrophils at 0 time had almost completely spread after 5 min (FIG. 10D) and developed shear-resistant adhesion (FIG. 10E). Cells did not become arrested on CD62 alone, because even after contact of activated neutrophils with CD62 bilayers under static conditions, rolling occurred after initiation of flow, and adhesion was not strengthened compared with unstimulated cells (FIG. 9B).

6.2. Discussion

We demonstrate herein that leukocyte rolling, a hallmark of the early stages of an inflammatory response, can be reconstituted in vitro on artificial lipid membranes containing an endothelial cell selectin, CD62. Neutrophils formed reversible rolling attachments to CD62 at physiologically relevant shear stresses. Another endothelial cell adhesion molecule, ICAM-1, did not support rolling adhesions, and was found to be significantly less effective than CD62 as a ligand for neutrophils under flow conditions. However, ICAM-1 was required for subsequent spreading and the development of a shear resistant attachment.

The selectin CD62 was distinctive from integrin and Ig family members both in ability to mediate rolling and to mediate adhesion during flow at physiologic shear stresses. When the avidity of neutrophil integrins for ICAM-1 was stimulated with PMA or fMLP, flowing neutrophils did not bind to ICAM-1 significantly over a range of physiologic shear stresses at which CD62 was highly effective. This was despite the ability of activated neutrophils to form attachments in static assays to 4-fold lower densities of ICAM-1. These attachments to ICAM-1 were greater than 100-fold more shear resistant than attachments to CD62. Integrins on activated T cells also failed to bind to ICAM-1 and fibronectin at physiologic shear stresses. Furthermore, an Ig family-Ig family interaction between CD2 on T lymphocytes and LFA-3 in artificial bilayers failed to occur at physiologic shear stresses. Even when adhesion of neutrophils or lymphocytes to ICAM-1 or lymphocytes to LFA-3 was initiated under static conditions, firm adhesion was unable to be converted to a rolling adhesion when shear flow was applied; cells either remained adherent or were completely dislodged. The shear stress required to dislodge 50% of cells binding through CD2 to the transmembrane isoform of LFA-3 is 1.5 dyn/cm$^2$ (Chan et al., 1991, J. Cell Biol. 115: 245); at a comparable ligand density a shear stress of 1 dyn/cm$^2$ dislodged 50% of neutrophils binding to CD62. The comparability of these shear stresses suggests that rolling is not directly related to binding strength.

We saw significant binding of neutrophils to CD62 at site densities as low as 50 per μm2, which is a physiologically relevant density. CD62 is stored in Weibel-Palade bodies of endothelial cells (Bonfanti et al., 1989, Blood 73: 1109–1112; McEver et al., 1989, J. Clin. Invest. 84: 92–99), which in response to stimuli such as thrombin and histamine fuse with the plasma membrane and thereby upregulate expression of CD62. An increase from 20 to 50 sites per μm$^2$ within 5 min after stimulation and a decline to baseline levels by 30 min is seen for endothelium cultured in vitro (Hattori et al., 1989, J. Biol. Chem. 264: 7768–7771). During passage of endothelial cells in vitro, there is a decline in CD62 and Weibel-Palade body content and therefore densities of CD62 could be higher in vivo.

Our studies demonstrating that CD62 is a receptor that mediates rolling suggest that its upregulation may be an important mechanism for regulating rolling in the inflammatory response. Thrombin stimulation mediates a transient binding of neutrophils that is CD18 independent and likely due to CD62 expression (Zimmerman and Mcintyre, 1988, J. Clin. Invest. 81: 531–537; Geng et al., 1990, Nature 343: 757–760). Neutrophil binding to primary culture endothelial cells at 2.0 dyn/cm$^2$ wall shear stress is stimulated by thrombin and is characterized by the initiation of rolling detectable within less than a 1 min of thrombin exposure, suggesting the involvement of CD62 (M. B. Lawrence and L. V. McIntire, unpublished data). Thus CD62 is an excellent candidate for the initiation of neutrophil rolling during the early stages of an inflammatory response.

Rolling velocities on CD62 were comparable to in vivo rolling velocities. On bilayers containing CD62, velocities ranged from under 2 to over 30 µm/s, depending on site density and the shear stress. Mean rolling velocities in vivo were 10 µm/s in mouse mesentery venules and 20 µm/s in hamster cheek pouch venules (Atherton and Born, 1973, J. Physiol. 233: 157–165). Rolling velocities on CD62 were proportional to the flow rate at low shear stresses, but increases were not proportional at higher shear stresses. Atherton and Born (1973, J. Physiol. 233: 157–165) reported that rolling velocities in vivo were linearly dependent on shear stress (blood flow velocity) up to about 5 dyn/cm$^2$ and plateaued above this point. The in vivo velocities at a given shear stress (Atherton and Born, 1973, J. Physiol. 233: 157–165) were about twice what we find on CD62 at 50 sites per µm$^2$; considering that other selectins may contribute to rolling in vivo and their concentration is unknown, the correspondence between these values is remarkable.

Neutrophils rolled on CD62 at shear stresses comparable to those found in post-capillary venules in vivo. Wall shear stresses at which rolling was observed in the measurements of Atherton and Born (1972, J. Physiol. 222: 447–474; 1973, J. Physiol. 233: 157–165) (assuming cylindrical geometry and a plasma viscosity of 2 centipoise) ranged from 1.5 to 4.0 dyn/cm$^2$. These values are similar to the shear stresses at which neutrophils form rolling attachments to bilayers containing CD62, and also to monolayers of endothelial cells stimulated with cytokines (Lawrence et al., 1990, Blood 75(1): 227–237) or thrombin (M. B. Lawrence and L. V. McIntire, unpublished data).

Other selectins have not been shown to mediate rolling; however, this family of molecules may be specialized to mediate rolling adhesions, and rolling observed in vivo may involve contributions from all three. LECAM-1 contributes to interaction of unactivated neutrophils with cytokine stimulated endothelial cells at physiologic shear stresses (Smith et al., 1991, J. Clin. Invest. 87: 609–618). On the basis of the ability of unactivated neutrophils to adhere under flow conditions, the selectins so far studied appear to be structures that are capable of mediating the initial attachment of neutrophils to the vessel wall.

The structure of selectins and their carbohydrate ligands appears ideally suited for their function in rolling and adhesion at high shear stresses. Kinetic considerations are very important here; a high on-rate for formation of the selectin-ligand complex is required for efficient interactions of rapidly flowing cells with a substrate, and both a rapid on-rate and rapid off-rate are required for rolling. We found no change in the cells or the substrate after prolonged rolling, suggesting that dissociation at the upstream edge of the cell is due to dissociation of the CD62-ligand complex rather than to loss of molecules from the cell or substrate.

Interactions between biological macromolecules are frequently diffusion limited; i.e., the rate at which they can form specific noncovalent interactions is limited by their rates of diffusion. Diffusion of the extracellular ligand binding domain of an adhesion receptor has two components, one due to segmental flexibility of the tether by which it is attached to the membrane and the other due to lateral diffusion in the membrane bilayer of the membrane anchor. With an appropriately high number of segments and high segmental flexibility, the former type of diffusion can occur more rapidly than the latter, since proteins of adhesion receptor size have diffusion coefficients on the order of $10^{-7}$ cm$^2$/s (Tanford, 1961, Physical Chemistry of Macromolecules, New York: John Wiley and Sons, Inc.) whereas bilayer diffusion coefficients are on the order of $10^{-9}$ cm$^2$/s (Jacobson et al., 1987, Ann. Rev. Physiol. 49: 163–175). The volume of solvent above the cell surface in which diffusion can occur and the diffusion rate are related to the length of the membrane tether, its segmental flexibility, and the size of the segments. Molecules composed of short consensus repeats of the type found in selectins have random configurations as revealed by electron microscopy (Weisman et al., 1990, Science 249: 146–151), suggesting a high degree of segmental flexibility. The (sialylated) Lewis x ligand of CD62 is found at the termini of long carbohydrate structures that are predicted to confer flexibility (Fukuda et al., 1984, J. Biol Chem. 259: 10925–10935). The location of the lectin binding domain and the Lewis x determinant at the termini of their respective structures maximizes diffusiveness due to segmental flexibility. The diffusion coefficient is inversely related to size; therefore, sialylated Lewis x, by virtue of its small size (molecular weight 779) relative to protein adhesion ligands, allows a faster rate for diffusion-limited processes.

Adhesiveness through integrins and the selectin CD62 differ drastically in the time scale required for their development. Binding of flowing cells to a substrate places stringent time constraints on adhesive bond formation that appear to prevent leukocyte integrin interactions with ICAM-1, even when neutrophils are activated. CD62 mediates adhesion on a time scale at which the leukocyte integrin interactions are ineffective. Bond formation through CD62 appears so rapid that little adhesion strengthening is apparent when binding under flow and static conditions are compared. Adhesion strengthening through integrins may take time to develop both because the globular putative ligand binding regions are quite large and are attached by two stalks to the membrane (Nermut et al., 1988, EMBO J. 7: 4092–4099), limiting diffusiveness, and because cooperative interactions between multiple integrins or with other molecules such as cytoskeletal components may be required. The latter may be reflected in the spreading that occurs during adhesion strengthening on ICAM-1 but not on CD62.

Inhibition of neutrophil binding to CD62 under flow conditions by prior activation with PMA may reflect an effect of the change to bipolar change rather than of loss of ligand-binding sites. CD62 binds at saturation to 20,000 sites per cell with a similar affinity or avidity of $10^9$ M$^{-1}$ to both resting and PMA-stimulated neutrophils (Moore et al., 1991, J. Cell Biol. 112: 491–499). When we bound PMA-stimulated and resting neutrophils to artificial bilayers containing CD62 at stasis and subjected them to detachment with shear, PMA-stimulated cells bound less efficiently, but the decrease in efficiency compared to untreated cells was much less marked than for binding under conditions of shear. Activated neutrophils with their bipolar, elongated shapes would experience higher transient torques than unstimulated, round cells in contact with a substrate. The shape change may therefore be an important factor that impedes adhesion in shear flow, and may help prevent activated leukocytes, if they fail to emigrate at an inflammatory site, from attaching and emigrating at an uninvolved site downstream.

Our studies demonstrate how a "weak", rolling interaction can develop into what is termed a "firm" adhesion to the vessel wall that neutrophils develop during an inflammatory response (Pober and Cotran, 1990, Transplantation 50: 537–544). Since neutrophils do not migrate on the lumenal side of the vessel wall, rolling allows an unstimulated neutrophil to move to a site where it can undergo diapedesis. Transendothelial cell migration, however, first requires the arrest of the rolling neutrophil. While it has been shown that transendothelial migration requires CD18 (Smith et al., 1988, J. Clin. Invest. 82: 1746–1756), how a neutrophil comes to a stop at an endothelial cell junction has been unknown. We demonstrated here that following activation of leukocyte integrins with a chemoattractant, neutrophils rolling on a bilayer containing CD62 and ICAM-1 rapidly slowed and came to a stop. Activation of LFA-1 and Mac-1 permitted interactions with ICAM-1 which then led to arrest and spreading. The firm adhesion observed in the microcirculation is blocked by in vivo administration of mAb to CD18 (Arfors et al., 1987, Blood 69: 338–340), and therefore appears equivalent to the shear-resistant attachment neutrophils form on ICAM-1 bilayers. At physiologic shear stress, rolling on a selectin was a prerequisite for neutrophil integrin interaction with ICAM-1. The rolling interaction may promote the integrin-ICAM-1 interaction both because it facilitates close physical interaction between integrins and ICAM-1, and because the neutrophil is rolling approximately two orders of magnitude more slowly than a tumbling neutrophil near the wall, which would raise the chance of enough bonds being formed for the rolling adhesion to be converted to a stationary one. Our findings suggest that activated integrins contribute to leukocyte arrest at sites of endothelial cell junctions and contribute to the mechanism for transendothelial migration. The neutrophil interaction with CD62 is highly reversible, and should not impede subsequent migration mediated by leukocyte integrins, since interactions through the leukocyte integrins are much stronger.

The synergism between the selectin and leukocyte integrin/Ig pathways demonstrated in our flow system is qualitatively different from the additivity observed in static adhesion assays. Use of anti-ELAM-1 and anti-CD18 antibodies singly or in combination and anti-LECAM-1 and anti-CD18 antibodies singly or in combination had suggested that the selectin and integrin mechanisms, while distinct, functioned in an additive manner in neutrophil adhesion to cytokine-stimulated endothelial cells (Dobrina et al., 1989, Immunology 67: 502–508; Luscinskas et al., 1989, J. Immunol. 142: 2257–2263; Smith et al., 1991, J. Clin. Invest. 87: 609–618; Hallmann et al., 1991, Biochem. Biophys. Res. Commun. 174: 236–243). Similar studies on the relative contribution of CD62 and CD18 to binding of neutrophils to thrombin-stimulated endothelial cells have not been reported, but it can be inferred from the existence of both a CD18-independent (presumably CD62) and CD18-dependent pathway in static assays (Zimmerman and Mcintyre, 1988, J. Clin. Invest. 81: 531–537) that there would be additive effects of blocking both adhesion mechanisms. Under flow conditions, however, we observed no additivity between CD62- and CD18-mediated mechanisms: no interaction was possible with ICAM-1 unless there was a rolling interaction with CD62. Our model of sequential interactions of rolling on CD62 followed by adhesion strengthening on ICAM-1 predicts that blocking interaction through either integrins or through selectins alone should completely block formation of firm adhesion in vivo, and is in agreement with observations that mAb to either integrins or a selectin (LECAM-1/LAM-1) can largely inhibit accumulation of leukocytes at inflammatory sites in vivo (Lewinsohn et al., 1987, J. Immunol. 138: 4313–4321; Jutila et al., 1989, J. Immunol. 143: 3318–3324; Arfors et al., 1987, Blood 69: 338–340; Price et al., 1987, J. Immunol. 139: 4174–4177).

The sequential steps of rolling on a selectin and adhesion strengthening through integrins elucidated here have important implications for the steps of leukocyte localization at inflammatory sites in vivo. Since rolling precedes firm sticking in vivo, and we have found that rolling is mediated by a selectin and is a prerequisite for subsequent adhesion strengthening through an integrin in vitro, we suggest that in vivo the initial accumulation of rolling leukocytes at an inflamed site must be regulated by selectins and by changes in vessel tone that lower fluid shear stresses to facilitate interactions through selectins. Small changes in vessel diameter and flow rate can result in significant reductions in wall shear stress. Stimulation of endothelial cells can induce expression of CD62 and later ELAM-1, and might also induce on these cells the expression of the ligand for LAM-1/LECAM-1. We found that rolling on CD62 by itself does not activate integrins on the neutrophil, but does permit adhesion strengthening through integrins if the neutrophil is activated. Chemoattractants that activate the avidity of integrins on neutrophils and monocytes are released at inflammatory sites. These include the complement component C5a, N-formylated bacterial peptides, platelet-derived growth factor, IL-8, and leukotriene B4. However, once these small molecules enter the bloodstream they are rapidly diluted and swept downstream, leading to the commonly held opinion that they cannot be responsible for regulating adhesion of leukocytes in postcapillary venules, and may only be effective once a neutrophil has undergone diapedesis. However, rolling in vivo will bring leukocytes into close proximity with chemoattractants that are diffusing from tissue through the junctions between endothelial cells, and to activating stimuli on the endothelial surface such as platelet-activating factor (Zimmerman et al., 1990, J. Cell Biol. 110: 529–540), and rolling will greatly prolong the time period over which leukocytes are exposed to these stimuli. This promotes the activation of integrin avidity on the leukocyte that we have shown slows rolling; activation of LAM-1/LECAM-1 on the leukocyte (Spertini et al., 1991, Nature 349: 691–694) might have a similar effect. The slowed rolling allows even more efficient exposure to chemostimulants and thereby sets in motion a positive feedback loop that results in arrest of the rolling leukocyte and finally spreading, integrin-mediated adhesion strengthening, and transendothelial migration.

In conclusion, we have shown that neutrophil rolling and subsequent arrest and adhesion strengthening at an inflammatory site in vivo can be accurately reproduced in vitro with a small number of purified components: a lipid bilayer, the selectin CD62, the Ig family member ICAM-1, and the chemostimulant fMLP. We predict that other types of selectins, integrin ligands, or chemostimulants will be found able to substitute for CD62, ICAM-1, or fMLP, respectively; nonetheless, the major point is that we have established the minimal molecular requirements for a complex physiological process. The small number of required components on the vessel wall demonstrates the simple elegance of this process and suggests how it may be refined by substitution or addition of other selectins or integrin ligands. Our studies illuminate the mechanisms by which adhesion molecule antibodies or analogues profoundly inhibit inflammatory responses in vivo, and suggest that antagonists of selectin or integrins may have similar biological effects despite distinct mechanisms of action.

6.3. Experimetnal Procedures

6.3.1. Monoclonal Antibodies

Monoclonal antibodies used in these studies as purified IgG were AC1.2 (anti-CD62, IgG1) (Larsen et al., 1989, Cell 59: 305–312), R6.5 (anti-ICAM-1, IgG2a) (Smith et al., 1988, J. Clin. Invest. 82: 1746–1756), and TS1/22 (anti-CD11a, IgG1) (Sanchez-Madrid et al., 1982, Proc. Natl. Acad. Sci. U.S.A. 79: 7489–7493). They were used at 20 µg/ml for inhibition of neutrophil binding. LPM19c (anti-CD11b, IgG2a) (Uciechowski and Schmidt, 1989, in Leucocyte Typing IV: White Cell Differentiation Antigens, W. Knapp, ed., Oxford: Oxford University Press, pp. 543–551) was used as a 1:200 dilution of ascites fluid.

6.3.2. Purification of ICAM-1 and CD62

ICAM-1 was affinity-purified from the Epstein-Barr Virus-transformed B lymphoblastoid JY cell clone 33 (Hollander et al., 1988, J. Immunol. 141: 4283–4290), as previously described (Marlin and Springer, 1987, Cell 51: 813–819). Briefly, a Triton X-100 lysate was passed over a RR1/1 Sepharose column, and the column was eluted with a buffer containing 1% octyl-β-D-glucopyranoside (OG) so that ICAM-1 could be incorporated into liposomes. CD62 was a generous gift of Drs. S. Sajer and B. Furie, and was purified as previously described (Larsen et al., 1989, Cell 59: 305–312).

6.3.3. Preparation of Liposomes

Liposomes were prepared by the method of OG dialysis (Mimms et al., 1981, Biochemistry 20: 833–840) with slight modification. Egg phosphatidylcholine (Avanti, Ala.) was diluted in chloroform and dried under an argon stream and then placed under a vacuum (30 µm Hg) for 2 hr to remove residual chloroform. The lipid film was redissolved at 0.4 µM in 250 µl of 25 µM Tris-HCl (pH 8.0)/150 µM NaCl (TS), 2% (w/v) OG, and was mixed with 250 µl of detergent solution containing approximately 1–18 µg/ml CD62, 6–30 µg/ml ICAM-1, or both in TS, 1% OG, followed by three changes of dialysis against TS at 4° C. over 36 hr. After the removal of OG by dialysis, the liposome suspension was stored at 4° C. under argon to minimize oxidation of lipids.

6.3.4. Preparation of Planar Bilayers

Planar bilayers were formed by incubating drops of liposome suspension on glass coverslips or slides at 22° C. for 30 min. Prior to use, all glass surfaces were boiled in detergent (Linbro 7×solution, Flow Lab, McLean, Va.) for 15 min, rinsed extensively in deionized distilled water for at least 24 hr, and then stored in ethanol. For site number determinations, glass coverslips (5 mm diameter, no. 1 thickness; Bellco, Vineland, N.J.) were attached to the bottom of 96-well microtiter plates (Linbro Titertek, Flow Lab, McLean, Va.) by silicone household glue (General Electric Co., Waterford, N.Y.), and liposome drops (20 µl) were placed on top. For laminar flow assays, glass slides (45×60 mm, no. 2 thickness; Corning Glass Works, Corning, Va.) were placed in 10 cm petri dishes. A liposome drop (20 µl) was placed in a demarcated area (1 cm diameter) and a glass coverslip (1 cm diameter; Bellco, Vineland, N.J.) was then used to spread the liposome droplet. After the planar bilayers were formed, excess liposomes were removed by several changes of binding medium (DMEM, 10% FCS, 25 mM HEPES, [pH 7.4]). Planar bilayers were never exposed to air.

6.3.5. Determination of Site Densities

Liposomes were reconstituted with different quantities of either immunoaffinity-purified ICAM-1 or CD62, and planar membranes were formed as described above. Monoclonal antibodies R6.5 to ICAM-1 (Smith et al., 1988, J. Clin. Invest. 82: 1746–1756) and AC1.2 to CD62 (Larsen et al., 1989, Cell 59: 305–312) were iodinated to a known specific activity of about 70 µCi/µg, and site densities of ICAM-1 and CD62 were determined by saturation binding, as previously described (Dustin and Springer, 1988, J. Cell Biol. 107: 321–331). Site numbers assume binding of one IgG molecule per antigen molecule because saturation binding favors monomeric binding and because transmembrane proteins are immobile on glass-supported bilayers (McConnell et al., 1986, Biochim. Biophys. Acta 864: 95–106) and at the highest density were on average too far apart (32 nm) for bivalent binding. After initial measurements of bilayer incorporation, protein concentrations were adjusted to give round numbers of sites per µm$^2$. The actual site densities were determined twice for each liposome preparation at each density, in triplicate. The round values of sites per µm$^2$ mentioned in results and actual values ±SD compared are as follows: ICAM-1,000: 950 ±95; ICAM-1 250: 272 ± 16; CD62 400: 389 ±62; CD62 200: 207 ±41; CD62 50: 64 ±12; CD62 25: 34 ±7. Incorporation of both CD62 and ICAM-1 did not affect the efficiency of incorporation compared to either alone.

6.3.6. Isolation of Polymorphonuclear Leukocytes

Neutrophils were isolated from citrate anticoagulated whole blood following dextran-sedimentation and density separation over Ficoll-Hypaque (Miller et al., 1987, J. Clin. Invest. 80: 535–544). Following isolation, neutrophils were stored in Hanks' balanced salt solution (HBSS; Gibco Laboratories, Grand Island, N.Y.) supplemented with 10 mM HEPES at pH 7.3 and human serum albumin (0.1%) at room temperature for up to 6 hr. Before use in experiments, the neutrophils were washed into HBSS supplemented with 10 mM HEPES, 1.0 mM Mg$^{2+}$, and 1.2 mM Ca$^{2+}$ at pH 7.3, since CD18 interactions with ICAM-1 require divalent cations (Marlin and Springer, 1987, Cell 51: 813–819), as does the CD62 interaction with its counterstructure (Geng et al., 1990, Nature 343: 757–760).

6.3.7. Laminar Flow Assays

A glass slide containing a planar bilayer was assembled in a parallel-plate laminar flow chamber (260 µm gap thickness) in which a uniform wall shear stress is generated. The flow chamber was mounted on the stage of an inverted phase-contrast microscope (Diaphot-TMD, Nikon Inc., Garden City, N.Y.). For continuous flow assays, neutrophils were resuspended at a concentration of 10$^6$/ml in HBSS supplemented with 10 mM HEPES, 1.2 mM Ca$^{2+}$, and 1.0 mM Mg$^{2+}$) and drawn through the chamber at controlled flow rates with a syringe pump attached to the outlet. The wall shear stress was calculated from a momentum balance on a Newtonian fluid, assuming a viscosity of 1.0 centipoise.

The flow rate was stepped down to allow measurements of cell binding at different shear stresses. Three minutes was allowed for equilibration before the number of cells per unit area was measured. Measurements on different areas of the bilayer were averaged, and no evidence for nonuniformity was found. Attached neutrophils and their motion were observed with phase-contrast objectives and quantitated by analysis of videotaped images. For activation studies, neutrophils were treated with PMA (30 ng/ml, final concentration) for 5 min before perfusing the cell suspension through the flow chamber.

6.3.8. Detachment Assays

For detachment assays, neutrophils ($4\times10^6$/ml) were injected into the chamber through a port and allowed to settle. To determine the effect of CD18 upregulation, PMA was added to the neutrophils 1 minute before injection into the flow chamber. All cells came in contact with the bilayer within 120 s, as indicated by their entry into the same focal plane. Controlled flow was applied following a 6 min incubation period. The initial shear force was 0.5 dyn/cm$^2$; this force was increased every 20 s to a maximum of 36 dyn/cm$^2$. All experiments were recorded on videotapes, and multiple fields of view were examined for each data point.

6.3.9. Analysis of Neutrophil Rolling

Rolling velocities were measured for all cells in two to five fields of view for each experiment at a given shear stress or ligand density. Results are presented as averages from experiments on different days. Velocities on CD62 were comparable whether cells were bound during shear flow or bound at stasis and then subjected to shear flow. Images were recorded on a time-lapse videocassette recorder at real time and played back at six- or nine-fold slower speed. The tape was paused to mark the location of cells and the displacement of the center of individual cells was measured 2 to 4 s later. In experiments in which the effect of chemotactic factors on neutrophil rolling was measured, cells were first allowed to form rolling attachments to the bilayer at the indicated shear stress. Flow at the same rate was continued with medium lacking cells for 3 min, followed by addition of N-formyl methionyl leucyl phenylalanine (fMLP) ($1\times10^{-9}$M, final concentration) to the perfusion media without stopping flow.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. An apparatus comprising (a) a solid phase having at least one surface containing a plurality of one or more substantially purified molecules, said molecules being capable of mediating rolling of a leukocyte on the solid phase surface; (b) a housing enclosing the solid phase, said housing having an inlet end and an outlet end for respectively receiving and removing a sample containing or suspected of containing leukocytes; (c) a means associated with the inlet for introducing said sample into the housing; and (d) a means associated with the outlet for withdrawing said sample from the housing, said apparatus being capable of permitting detection of leukocyte rolling on the solid phase surface.

2. A solid phase having at least one surface containing a plurality of one or more substantially purified molecules, said molecules being capable of mediating rolling of a leukocyte on the solid phase surface, wherein the solid phase has a plurality of zones on said surface, each zone containing a different said molecule.

3. The solid phase of claim 2 wherein said surface also contains a plurality of one or more substantially purified integrin binding partners.

4. An apparatus comprising (a) a solid phase having at least one surface containing a plurality of one or more substantially purified molecules, said molecules being capable of mediating rolling of a leukocyte on the solid phase surface and (b) a housing enclosing the solid phase, said housing having an inlet end and an outlet end for respectively receiving and removing a sample containing or suspected of containing leukocytes wherein the solid phase is a microscope slide.

5. A solid phase having at least one surface containing a plurality of one or more substantially purified molecules, said molecules being capable of mediating rolling of a leukocyte on the solid phase surface, wherein the solid phase is a planar phase comprising glass, and a lipid bilayer is present on said surface, said lipid bilayer containing said molecules.

6. The solid phase of claim 5 in which said surface also contains a plurality of one or more substantially purified integrin binding partners.

7. The solid phase of claim 5 in which said molecules are CD62.

8. A solid phase having at least one surface containing a plurality of one or more substantially purified molecules, said molecules being capable of mediating rolling of a leukocyte on the solid phase surface, wherein said surface also contains a plurality of one or more substantially purified integrin binding partners immobilized on said surface.

9. The solid phase of claim 8 in which the integrin binding partners are selected from the group consisting of ICAM-1, ICAM-2, VCAM-1, and any combination of the foregoing.

10. The solid phase of claim 8 in which the solid phase is plastic.

11. A solid phase having at least one surface containing (a) a plurality of one or more substantially purified molecules, said molecules being capable of mediating rolling of a leukocyte on the solid phase surface; and (b) a plurality of one or more substantially purified integrin binding partners; said solid phase further comprising a plurality of leukocytes adhering to said surface of the solid phase.

12. The solid phase of claim 8 or 6 in which said molecules are CD62, and the integrin binding partners are ICAM-1.

13. An apparatus comprising:
(a) a solid phase having (i) a plurality of one or more substantially purified molecules contained on a surface of the solid phase, said molecules being capable of mediating rolling of a leukocyte on said solid phase surface, and (ii) a plurality of one or more substantially purified integrin binding partners contained on said surface;
(b) inlet means for receiving a fluid sample and for permitting the sample to enter onto the surface of the solid phase; and
(c) outlet means for permitting the fluid sample after it has flowed across at least a portion of the surface of the solid phase to exit said surface.

14. The apparatus of claim 13 which further comprises a means associates with the outlet means, for removing fluid from the outlet means.

15. The apparatus of claim 13 which further comprises a means associated with the inlet means, for introducing the fluid sample into the inlet means, and a means associated with the outlet means, for removing the fluid sample from the outlet means.

16. The apparatus of claim 15 further comprising a housing containing said solid phase, inlet means, and outlet means.

17. The apparatus of claim 16 in which said molecules are CD62, and the integrin binding partners are ICAM-1.

18. The apparatus of claim 16 in which said molecules are selected from the group consisting of CD62, ELAM-1, MECA-79 antigen, and any combination of the foregoing; and the integrin binding partners are selected from the group consisting of ICAM-1, ICAM-2, VCAM-1, and any combination of the foregoing.

19. The apparatus of claim 13 further comprising a housing containing said solid phase, inlet means, and outlet means.

20. The apparatus of claim 19 in which the housing provides a container for fluid flowing past the surface of the solid phase.

21. The apparatus of claim 20 in which physiologic shear stress can be achieved at the surface of the solid phase.

22. The apparatus of claim 21 in which the shear stress is in the range of from about 0.5 to about 4.0 dynes per square centimeter.

23. The apparatus of claim 22 in which said molecules are CD62, and the integrin binding partners are ICAM-1.

24. The apparatus of claim 19 further comprising a video camera or microscope operatively linked for viewing the surface of the solid phase.

25. The apparatus of claim 13 which further comprises a pump associated with the outlet means.

26. The apparatus of claim 13 in which said molecules are CD62.

27. The apparatus of claim 13 in which said molecules are CD62, and the integrin binding partners are ICAM-1.

28. The apparatus of claim 13 in which said molecules are selected from the group consisting of CD62, ELAM-1, and MECA-79 antigen, and any combination of the foregoing; and the integrin binding partners are selected from the group consisting of ICAM-1, ICAM-2, VCAM-1, and any combination of the foregoing.

29. The apparatus of claim 13, 27, or 17 in which the solid phase is a planar phase comprising glass, and a planar lipid bilayer is present on said surface, said lipid bilayer containing said molecules and the integrin binding partners.

30. An apparatus comprising:
   (a) a solid phase having a plurality of one or more substantially purified molecules contained on a surface of the solid phase, said molecules being capable of mediating rolling of a leukocyte on said solid phase surface;
   (b) inlet means for receiving a fluid sample and for permitting the sample to enter onto the surface of the solid phase; and
   (c) outlet means for permitting the fluid sample after it has flowed across at least a portion of the surface of the solid phase to exit said surface;
   (d) a means associated with the inlet means, for introducing the fluid sample into the inlet means;
   (e) a means associated with the outlet means, for removing the fluid sample from the outlet means;
   said apparatus being capable of permitting detection of leukocyte rolling on the solid phase surface.

31. The apparatus of claim 30 further comprising a housing containing said solid phase, inlet means, and outlet means.

32. The apparatus of claim 31 in which the housing provides a container for fluid flowing past the surface of the solid phase.

33. The apparatus of claim 32 in which physiologic shear stress can be achieved at the surface of the solid phase.

34. The apparatus of claim 33 in which the shear stress is in the range of from about 0.5 to about 4.0 dynes per square centimeter.

35. The apparatus of claim 34 in which said molecules are CD62.

36. The apparatus of claim 31 in which said molecules are CD62.

37. The apparatus of claim 36 or 35 in which the solid phase is a planar phase comprising glass, and a planar lipid bilayer is present on said surface, said lipid bilayer containing said molecules.

38. The apparatus of claim 31 in which said molecules are selected from the group consisting of CD62, ELAM-1, MECA-79 antigen, and any combination of the foregoing.

39. The apparatus of claim 30 in which the inlet means is an inlet tube or pipe, and the outlet means is an outlet tube or pipe.

40. The apparatus of claim 1, 4 or 30 in which said molecules are CD62.

41. The apparatus of claim 1, 4 or 30 in which said molecules are selected from the group consisting of CD62, ELAM-1, MECA-79 antigen, and any combination of the forgoing.

42. An apparatus comprising:
   (a) a planar solid phase having a plurality of one or more substantially purified molecules contained on a surface of the solid phase, said molecules being capable of mediating rolling of a leukocyte on said solid phase surface;
   (b) a base having (i) an inlet manifold, (ii) an outlet manifold, and (iii) a recessed lip on its lower surface;
   (c) a deck positioned below the base, having (i) an entrance slot communicating with the inlet manifold, and (ii) an exit slot communicating with the outlet manifold;
   (d) a longitudinal compressible gasket positioned within the recessed lip of the base, its top surface contacting the base, and having an aperture of a size and shape substantially congruent with the deck;
   in which the planar solid phase is positioned on the bottom surface of the gasket, such that the solid phase surface with said molecules is communicating with the aperture of the gasket.

43. The apparatus of claim 42 further comprising a means for applying force whereby the gasket and solid phase are compressed together and their disengagement from the base is prevented.

44. The apparatus of claim 42 further comprising pump connected to the outlet manifold.

45. The apparatus of claim 42 in which the solid phase comprises glass; and a planar lipid bilayer is present on said solid phase surface, said lipid bilayer containing said molecules.

46. The apparatus of claim 45 in which said molecules are CD62.

47. The apparatus of claim 42 in which a plurality of one or more substantially purified integrin binding partners are also contained on said surface of the solid phase.

48. The apparatus of claim 47 in which the solid phase comprises glass; and a planar lipid bilayer is present on said solid phase surface, said lipid bilayer containing said molecules and the integrin binding partners.

49. The apparatus of claim 48 in which said molecules are CD62, and the integrin binding partners are ICAM-1.

50. The apparatus of claim 47 in which said molecules are CD62, and the integrin binding partners are ICAM-1.

51. The apparatus of claim 47 in which said molecules are selected from the group consisting of CD62, ELAM-1, MECA-79 antigen, and any combination of the foregoing; and the integrin binding partners are selected from the group consisting of ICAM-1, ICAM-2, VCAM-1, and any combination of the foregoing.

52. The apparatus of claim 42 in which said molecules are CD62.

53. The apparatus of claim 42, in which said molecules are selected from the group consisting of CD62, ELAM-1, MECA-79 antigen, and any combination of the foregoing.

54. An apparatus comprising:
(a) a solid phase having a plurality of one or more substantially purified molecules contained on a surface of the solid phase, said molecules being capable of mediating rolling of a leukocyte on said solid phase surface;
(b) inlet means for receiving a fluid sample and for permitting the sample to enter onto the surface of the solid phase;
(c) outlet means for permitting the fluid sample after it has flowed across at least a portion of the surface of the solid phase to exit said surface,
(d) a housing containing said solid phase, inlet means, and outlet means; and
(e) a video camera or microscope operatively linked for viewing the surface of the solid phase.

55. An apparatus comprising:
(a) a planar solid phase comprising glass;
(b) a planar lipid bilayer present on a surface of the solid phase, said lipid bilayer containing a plurality of one or more substantially purified molecules, said molecules being capable of mediating rolling of a leukocyte;
(c) inlet means for receiving a fluid sample and for permitting the sample to enter onto the lipid bilayer; and
(d) outlet means for permitting the fluid sample after it has flowed across at least a portion of the lipid bilayer to exit said surface.

56. A method of collecting or purifying leukocytes from a fluid sample comprising:
(a) contacting a surface of a solid phase with a fluid sample containing leukocytes, said surface containing a plurality of one or more substantially purified molecules, said molecules being capable of mediating rolling of a leukocyte on said solid phase surface, in which the contacting is under conditions that provide relative movement between the solid phase and the leukocytes in the sample, thereby allowing a plurality of leukocytes in the sample which express a binding partner to said molecules to roll on the surface of the solid phase; and
(b) recovering the leukocytes that roll on the surface.

57. The method according to claim 56 in which the relative movement between the solid phase and the leukocytes is such that physiologic shear stress is achieved at the surface of the solid phase.

58. The method according to claim 56 in which the leukocytes are recovered by recovering the solid phase and removing the leukocytes from the solid phase.

59. A method of collecting or purifying leukocytes from a fluid sample comprising:
(a) contacting a surface of a solid phase with a fluid sample containing leukocytes, said surface containing a plurality of one or more substantially purified molecules, said molecules being capable of mediating rolling of a leukocyte on said solid phase surface, in which the contacting is under conditions that provide relative movement between the solid phase and the leukocytes in the sample such that bulk flow is induced and shear stresses at the surface of the solid phase are in the range of from about 0.5 to about 4.0 dynes per square centimeter, thereby allowing a plurality of leukocytes in the sample which express a binding partner to said molecules to roll on the surface of the solid phase; and
(b) recovering the leukocytes that roll on the surface.

60. The method according to claim 59 in which the solid phase is comprised of glass fibers, said molecules are CD62, and a planar lipid bilayer containing CD62 is present on the surface of the solid phase.

61. The method according to claim 56 or 59 in which said molecules are selected from the group consisting of CD62, ELAM-1, MECA-79 antigen, and any combination of the foregoing.

62. A method for collecting or purifying leukocytes comprising:
(a) contacting a surface of a solid phase with a fluid sample containing a chemoattractant and containing leukocytes, said surface containing a plurality of one or more substantially purified molecules and a plurality of one or more substantially purified integrin binding partners, said molecules being capable of mediating rolling of a leukocyte on said solid phase surface, in which said contacting is under conditions that provide relative movement between the solid phase and the leukocytes in the sample, thereby allowing a plurality of leukocytes which express (i) a binding partner to said molecules, (ii) a receptor for the chemoattractant, and (iii) an integrin recognizing the integrin binding partners, to become arrested on the surface of the solid phase; and
(b) recovering the arrested leukocytes from the solid phase.

63. The method according to claim 62 in which the relative movement between the solid phase and the leukocytes is such that bulk flow is induced and shear stresses at the surface of the solid phase are in the range of from about 0.5 to about 4.0 dynes per square centimeter.

64. The method according to claim 62 in which said molecules are selected from the group consisting of CD62, ELAM-1, MECA-79 antigen, and any combination of the foregoing; and the integrin binding partners are selected from the group consisting of ICAM-1, ICAM-2, VCAM-1, and any combination of the foregoing.

65. The method according to claim 63 in which the solid phase is comprised of glass, said molecules are CD62, said integrin binding partners are ICAM-1, said chemoattractant is N-formyl methionyl leucyl phenylalanine, and a planar lipid bilayer containing CD62 and ICAM-1 is present on the surface of the solid phase.

66. A method for analysis of a fluid sample containing leukocytes, comprising (a) contacting a surface of a solid phase with a fluid sample containing leukocytes, said surface containing a plurality of one or more substantially purified molecules, said molecules being capable of mediating rolling of a leukocyte on said solid phase surface, in which said contacting is under conditions that provide relative movement between the solid phase and the leukocytes in the sample, thereby allowing a plurality of leukocytes which express a binding partner to said molecules to roll along the surface of the solid phase; and (b) detecting or quantifying the leukocytes that roll along the surface.

67. The method according to claim 66 in which the relative movement between the solid phase and the leukocytes is such that physiologic shear stress is achieved at the surface of the solid phase.

68. A method for analysis of a fluid sample containing leukocytes, comprising:

(a) contacting a surface of a solid phase with a fluid sample containing leukocytes, said solid phase containing a plurality of one or more substantially purified molecules, said molecules being capable of mediating rolling of a leukocyte on said solid phase surface, in which said contacting is under conditions that provide relative movement between the solid phase and the leukocytes in the sample such that bulk flow is induced and shear stresses at the surface of the solid phase are in the range of from about 0.5 to about 4.0 dynes per square centimeter, thereby allowing a plurality of leukocytes which express a binding partner to said molecules to roll along the surface of the solid phase; and (b) detecting or quantifying the leukocytes that roll along the surface.

69. The method according to claim 68 in which the solid phase is comprised of glass, said molecules are CD62, and a planar lipid bilayer containing CD62 is present on the surface of the solid phase.

70. The method according to claim 66 or 68 in which said molecules are selected from the group consisting of CD62, ELAM-1, MECA-79 antigen, and any combination of the foregoing.

71. A method for analysis of a fluid sample containing leukocytes, comprising:

(a) contacting a surface of a solid phase with a fluid sample containing a chemoattractant and containing leukocytes, said surface containing a plurality of one or more substantially purified molecules and a plurality of one or more substantially purified integrin binding partners, said molecules being capable of mediating rolling of a leukocyte on said solid phase surface, in which said contacting is under conditions that provide relative movement between the solid phase and the leukocytes in the sample, thereby allowing a plurality of leukocytes which express (i) a binding partner to said molecules, (ii) a receptor for the chemoattractant, and (iii) an integrin recognizing the integrin binding partners, to become arrested on the surface of the solid phase; and (b) detecting or quantifying the leukocytes arrested on the solid phase.

72. The method according to claim 71 in which the relative movement between the solid phase and the leukocytes is such that physiologic shear stress is achieved at the surface of the solid phase.

73. The method according to claim 71 in which said molecules are selected from the group consisting of CD62, ELAM-1, MECA-79 antigen, and any combination of the foregoing; and the integrin binding partners are selected from the group consisting of ICAM-1, ICAM-2, VCAM-1, and any combination of the foregoing.

74. A method for diagnosing a disease or disorder in a subject, comprising (a) contacting a surface of a solid phase with a fluid sample derived from a subject and containing leukocytes, said surface containing a plurality of one or more substantially purified molecules, said molecules being capable of mediating rolling of a leukocyte on said solid phase surface, in which said contacting is under conditions that provide relative movement between the solid phase and the leukocytes in the sample, thereby allowing a plurality of leukocytes which express a binding partner to said molecules to roll along the surface of the solid phase; and (b) measuring the number or percentage of the leukocytes or a subset thereof that roll on the surface of the solid phase; in which an increase or decrease in said number or percentage relative to the number or percentage of leukocytes or the subset thereof that roll on the surface from an equivalent fluid sample from a healthy individual, indicates the presence of the disease or disorder in the subject.

75. The method according to claim 74 in which the relative movement between the solid phase and the leukocytes is such that physiologic shear stress is achieved at the surface of the solid phase.

76. The method according to claim 75 in which the solid phase is comprised of glass, said molecules are CD62, and a planar lipid bilayer containing CD62 is present on the surface of the solid phase.

77. The method according to claim 74 in which said molecules are selected from the group consisting of CD62, ELAM-1, MECA-79 antigen, and any combination of the foregoing.

78. The method according to claim 74 in which the disease or disorder is a leukemia and the number or percentage of rolling leukocytes or a subset thereof in the sample derived from the subject is increased.

79. The method according to claim 74 in which the disease or disorder is a neutropenia and the number or percentage of rolling leukocytes or a subset thereof in the sample derived from the subject is decreased.

80. A method for diagnosing a disease or disorder in a subject comprising (a) contacting a surface of a solid phase with a fluid sample containing a chemoattractant and containing leukocytes, and said leukocytes obtained from a subject, said surface containing a plurality of one or more substantially purified molecules and a plurality of one or more substantially purified integrin binding partners, said molecules being capable of mediating rolling of a leukocyte on said solid phase surface, in which said contacting is under conditions that provide relative movement between the solid phase and the leukocytes in the sample, thereby allowing a plurality of leukocytes which express (i) a binding partner to said molecules, (ii) a receptor for the chemoattractant, and (iii) an integrin recognizing the integrin binding partners, to become arrested on the surface of the solid phase; and (b) measuring the number or percentage of the leukocytes or a subset thereof that are arrested on the surface of the solid phase; in which an increase or decrease in said number or percentage, relative to the number or percentage of leukocytes or the subset thereof that are arrested on the surface from an equivalent fluid sample containing leukocytes from a healthy individual, indicates the presence of the disease or disorder in the subject.

81. The method according to claim 80 in which the relative movement between the solid phase and the leukocytes is such that physiologic shear stress is achieved at the surface of the solid phase.

82. The method according to claim 80 in which said molecules are selected from the group consisting of CD62, ELAM-1, MECA-79 antigen, and any combination of the foregoing; and the integrin binding partners are selected from the group consisting of ICAM-1, ICAM-2, VCAM-1, and any combination of the foregoing.

83. A method for identifying a candidate compound capable of inhibiting a component of the inflammatory response, comprising (a) contacting a surface of a solid phase with a fluid sample containing leukocytes and containing a test compound, said surface containing a plurality of one or more substantially purified molecules, said molecules being capable of mediating rolling of a leukocyte on said solid phase surface, in which said contacting is under conditions that provide relative movement between the solid phase and the leukocytes in the sample, thereby allowing a plurality of leukocytes which express a binding partner to said molecules to roll on the surface of the solid phase; and (b) determining the number or percentage of leukocytes or a subset thereof rolling on the surface of the solid phase, in which a decrease in said number or percentage relative to the number or percentage of leukocytes or the subset thereof which roll in the absence of the test compound indicates that the test compound is capable of inhibiting the inflammatory response.

84. The method according to claim 83 in which the relative movement between the solid phase and the leukocytes is such that physiologic shear stress is achieved at the surface of the solid phase.

85. The method according to claim 84 in which said molecules are CD62.

86. The method according to claim 83 or 85 in which the solid phase is comprised of glass, and a planar lipid bilayer in which contains said molecules is present on the surface of the solid phase.

87. The method according to claim 84 in which said molecules are selected from the group consisting of CD62, ELAM-1, MECCA-79, and any combination of the foregoing.

88. A method for identifying a candidate compound capable of inhibiting a component of the inflammatory response, comprising (a) contacting a surface of a solid phase with a fluid sample containing (i) leukocytes, (ii) a chemoattractant, and (iii) a test compound; said surface containing a plurality of one or more substantially purified molecules and a plurality of one or more substantially purified integrin binding partners, said molecules being capable of mediating rolling of a leukocyte on said solid phase surface; in which said contacting is under conditions that provide relative movement between the solid phase and the leukocytes in the sample, thereby allowing a plurality of leukocytes in the sample which express (i) a binding partner to said molecules, (ii) a receptor for the chemoattractant, and (iii) an integrin recognizing the integrin binding partners, to become arrested on the surface of the solid phase; and (b) determining the number or percentage of arrested leukocytes, or a subset thereof, in which a decrease in such number or percentage relative to the number or percentage of leukocytes or the subset thereof which are arrested in the absence of the test compound indicates that the test compound is capable of inhibiting the inflammatory response.

89. The method according to claim 88 in which the relative movement between the solid phase and the leukocytes is such that physiologic shear stress is achieved at the surface of the solid phase.

90. The method according to claim 88 in which said molecules are CD62 and the integrin binding partners are ICAM-1.

91. The method according to claim 88 in which the solid phase is comprised of glass, and a planar lipid bilayer which contains said molecules is present on the surface of the solid phase.

92. A method for identifying a candidate compound capable of promoting a component of the inflammatory response, comprising:

(a) contacting a surface of a solid phase with a fluid sample containing leukocytes and containing a test compound, said surface containing a plurality of one or more substantially purified molecules, said molecules being capable of mediating rolling of a leukocyte on said solid phase surface, in which said contacting is under conditions that provide relative movement between the solid phase and the leukocytes in the sample, thereby allowing a plurality of leukocytes which express a binding partner to said molecules to roll on the surface of the solid phase; and (b) determining the number or percentage of leukocytes or a subset thereof rolling on the surface of the solid phase, in which an increase in said number or percentage relative to the number or percentage of leukocytes or the subset thereof which roll in the absence of the test compound indicates that the test compound is capable of promoting the inflammatory response.

93. A method for identifying a candidate compound capable of promoting a component of the inflammatory response, comprising:

(a) contacting a surface of a solid phase with a fluid sample containing (i) leukocytes, (ii) a chemoattractant, and (iii) a test compound; said surface containing a plurality of one or more substantially purified molecules and a plurality of one or more substantially purified integrin binding partners; said molecules being capable of mediating rolling of a leukocyte on said solid phase surface, in which said contacting is under conditions that provide relative movement between the solid phase and the leukocytes in the sample, thereby allowing a plurality of leukocytes in the sample which express (i) a binding partner to said molecules, (ii) a receptor for the chemoattractant; and (iii) an integrin recognizing the integrin binding partners, to become arrested on the surface of the solid phase; and (b) determining the number or percentage of arrested leukocytes or a subset thereof, in which a increase in such number or percentage relative to the number or percentage of leukocytes or the subset thereof which are arrested in the absence of the test compound indicates that the test compound is capable of promoting the inflammatory response.

94. The method according to claim 92 or 93 in which the relative movement between the solid phase and the leukocytes is such that physiologic shear stress is achieved at the surface of the solid phase.

95. A method for identifying a molecule capable of mediating rolling of a leukocyte on a solid phase surface containing said molecule, comprising:
   (a) contacting a surface of a solid phase with a fluid sample containing leukocytes, said surface containing a plurality of a substantially purified test molecule, in which said contacting is under conditions that provide relative movement between the solid phase and the leukocytes in the sample; and
   (b) detecting any leukocytes that roll on the surface, in which rolling of leukocytes on the surface indicates that the test molecule is capable of mediating rolling of a leukocyte on a solid phase surface containing the test molecule.

96. The method according to claim 95 in which the solid phase is comprised of glass, and a planar lipid bilayer which contains the test molecules is present on the surface of the solid phase.

97. A method for identifying a leukocyte chemoattractant, comprising:
   (a) contacting a surface of a solid phase with a fluid sample containing leukocytes and containing a test compound, said surface containing a plurality of one or more substantially purified molecules and a plurality of one or more substantially purified integrin binding partners, said molecules being capable of mediating rolling of a leukocyte on said solid phase surface, in which said contacting is under conditions that provide relative movement between the solid phase and the leukocytes in the sample; and
   (b) detecting any leukocytes that are arrested on the surface, in which arrest of leukocytes on the surface indicates that the test compound is a leukocyte chemoattractant.

98. The method according to claim 97 in which the solid phase is comprised of glass, said molecules are CD62, said integrin binding partners are ICAM-1, and a planar lipid bilayer containing CD62 and ICAM-1 is present on the surface of the solid phase.

99. A method for identifying an integrin binding partner, comprising:
   (a) contacting a surface of a solid phase with a fluid sample containing a chemoattractant and containing leukocytes, said surface containing a plurality of one or more substantially purified molecules and a plurality of a substantially purified test compound, said molecules being capable of mediating rolling of a leukocyte on said solid phase surface, in which said contacting is under conditions that provide relative movement between the solid phase and the leukocytes in the sample; and
   (b) detecting any leukocytes that are arrested on the surface, in which arrest of leukocytes on the surface indicates that the test compound is an integrin binding partner.

100. The method according to claim 99 in which the solid phase is comprised of glass, said molecules are CD62, and a planar lipid bilayer containing CD62 and the test compounds is present on the surface of the solid phase.

101. The method according to claim 95, 97, or 99 in which the relative movement between the solid phase and the leukocytes is such that physiologic shear stress is achieved at the surface of the solid phase.

* * * * *